United States Patent
Gardner et al.

(10) Patent No.: US 8,501,782 B2
(45) Date of Patent: Aug. 6, 2013

(54) PIPERIDINYL DERIVATIVES AS MODULATORS OF CHEMOKINE RECEPTOR ACTIVITY

(75) Inventors: Daniel S. Gardner, Furlong, PA (US); John V. Duncia, Newtown, PA (US); John Hynes, Washington Crossing, PA (US); T.G. Murali Dhar, Newtown, PA (US); Percy H. Carter, Princeton, NJ (US); Joseph B. Santella, Springfield, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 718 days.

(21) Appl. No.: 12/670,016

(22) PCT Filed: Jul. 23, 2008

(86) PCT No.: PCT/US2008/070801
§ 371 (c)(1),
(2), (4) Date: Jan. 21, 2010

(87) PCT Pub. No.: WO2009/015164
PCT Pub. Date: Jan. 29, 2009

(65) Prior Publication Data
US 2010/0204274 A1    Aug. 12, 2010

Related U.S. Application Data

(60) Provisional application No. 60/951,479, filed on Jul. 24, 2007, provisional application No. 61/081,521, filed on Jul. 17, 2008.

(51) Int. Cl.
| | |
|---|---|
| A61K 31/4545 | (2006.01) |
| A61K 31/454 | (2006.01) |
| A61K 31/4525 | (2006.01) |
| A61K 31/451 | (2006.01) |
| C07D 405/12 | (2006.01) |
| C07D 401/12 | (2006.01) |
| C07D 401/04 | (2006.01) |
| C07D 211/52 | (2006.01) |

(52) U.S. Cl.
USPC ........... 514/327; 514/326; 514/318; 514/328; 546/210; 546/217; 546/194; 546/214; 546/208; 546/211; 546/220

(58) Field of Classification Search
USPC .................. 514/326, 327, 318, 328; 546/210, 546/217, 194, 214, 208, 211, 220
See application file for complete search history.

(56) References Cited

U.S. PATENT DOCUMENTS

| | | | |
|---|---|---|---|
| 7,601,844 B2 | 10/2009 | Carter et al. | |
| 7,615,556 B2 | 11/2009 | Carter et al. | |
| 7,985,861 B2 * | 7/2011 | Carter et al. | 546/226 |
| 2007/0208056 A1 * | 9/2007 | Carter et al. | 514/317 |

FOREIGN PATENT DOCUMENTS

| | | |
|---|---|---|
| WO | WO 2004/043965 | 5/2004 |
| WO | WO 2005/054227 | 6/2005 |
| WO | WO 2006/004741 | 1/2006 |
| WO | WO 2006137465 A1 * | 12/2006 |
| WO | WO 2007/092681 | 8/2007 |

OTHER PUBLICATIONS

Machine translation of WO 2006/137465 A1 by Masui et al. obtained from http://patentscope.wipo.int/search/en/search.jsf on Nov. 13, 2012.*

* cited by examiner

*Primary Examiner* — Joseph Kosack
*Assistant Examiner* — Matthew Coughlin
(74) *Attorney, Agent, or Firm* — Terence J. Bogie

(57) ABSTRACT

The present application describes modulators of MIP-1α of formula (I) or stereoisomers or prodrugs or pharmaceutically acceptable salts thereof, wherein m, Q, T, W, Z, $R_1$, $R_3$, $R_4$, $R_5$, $R_{5a}$ and $R_{5b}$, are as defined herein. In addition, methods of treating and preventing inflammatory diseases such as asthma and allergic diseases, as well as autoimmune pathologies such as rheumatoid arthritis and atherosclerosis using the modulators of formula (I) are disclosed.

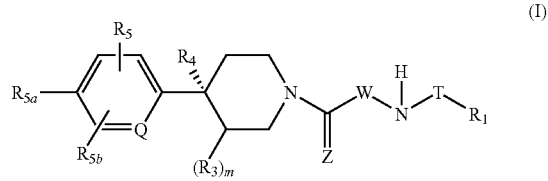

(I)

11 Claims, No Drawings

PIPERIDINYL DERIVATIVES AS MODULATORS OF CHEMOKINE RECEPTOR ACTIVITY

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik et al., *Immunity* 2000, 12, 121): CCR-1 (or "CKR-1" or "CC-CKR-1") [MIP-1α, MCP-3, MCP-4, RANTES] (Ben-Barruch et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Samson et al., *Biochemistry* 1996, 35, 3362-3367); CCR-6 (or "CKR-6" or "CC-CKR-6") [LARC] (Baba et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [1-309] (Napolitano et al., *J. Immunol.*, 1996, 157, 2759-2763); CCR-10 (or "CKR-10" or "CC-CKR-10") [MCP-1, MCP-3] (Bonini et al., *DNA and Cell Biol.* 1997, 16, 1249-1256); and CCR-11 [MCP-1, MCP-2, and MCP-4] (Schweickart, et al., *J. Biol. Chem.* 2000, 275, 9550).

In addition to the mammalian chemokine receptors, mammalian cytomegaloviruses, herpesviruses and poxviruses have been shown to express, in infected cells, proteins with the binding properties of chemokine receptors (reviewed in: Wells et al., *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Carter, P. H., *Current Opinion in Chemical Biology* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., *J. Immun.* 2000, 164, 3392-3401).

Demonstration of the importance of the MIP-1α/CCR-1 interaction has been provided by experiments with genetically modified mice. MIP-1α−/− mice had normal numbers of leukocytes, but were unable to recruit monocytes into sites of viral inflammation after immune challenge (Cook, D. et al., *Science* 1995, 269, 1583-1585). Recently, MIP-1α−/− mice were shown to be resistant to collagen antibody induced arthritis (Chintalacharuvu, S. R., *Immun. Lett.* 2005, 202-204). Likewise, CCR-1−/− mice were unable to recruit neutrophils when challenged with MIP-1α in vivo; moreover, the peripheral blood neutrophils of CCR-1 null mice did not migrate in response to MIP-1α (Gao, B. et al., *J. Exp. Med.* 1997, 185, 1959-1968), thereby demonstrating the specificity of the MIP-1α/CCR-1 interaction. The viability and generally normal health of the MIP-1α−/− and CCR-1−/− animals is noteworthy, in that disruption of the MIP-1α/CCR-1 interaction does not induce physiological crisis. Taken together, these data lead one to the conclusion that molecules that block the actions of MIP-1α would be useful in treating a number of inflammatory and autoimmune disorders. This hypothesis has now been validated in a number of different animal disease models, as described below.

It is known that MIP-1α is elevated in the synovial fluid and blood of patients with rheumatoid arthritis (Koch, A. et al., *J. Clin. Invest.* 1994, 93, 921-928). Moreover, several studies have demonstrated the potential therapeutic value of antagonism of the MIP-1α/CCR1 interaction in treating rheumatoid arthritis (Pease, J. E. et al., *Expert Opin. Invest. Drugs* 2005, 14, 785-796).

An antibody to MIP-1α was shown to ameliorate experimental autoimmune encepahlomytis (EAE), a model of multiple sclerosis, in mice (Karpus, W. J. et al., *J. Immun.* 1995, 5003-5010). Likewise, inflammatory disease symptoms could be controlled via direct administration of antibodies for MIP-1α to mice with collagen-induced arthritis (Lukacs, N. W. et al., *J. Clin. Invest.* 1995, 95, 2868-2876).

It should also be noted that CCR-1 is also the receptor for the chemokines RANTES, MCP-3, HCC-1, Lkn-1/HCC-2, HCC-4, and MPIF-1 (Carter, P. H., *Curr. Opin Chem. Bio.* 2002, 6, 510-525). Since it is presumed that the new compounds of formula (I) described herein antagonize MIP-1α by binding to the CCR-1 receptor, it may be that these compounds of formula (I) are also effective antagonists of the actions of the aforementioned ligand that are mediated by CCR-1. Accordingly, when reference is made herein to "antagonism of MIP-1α," it is to be assumed that this is equivalent to "antagonism of chemokine stimulation of CCR-1."

For example, demonstration of the chemotactic properties of RANTES in humans has been provided experimentally. Human subjects, when injected intradermally with RANTES, experienced an influx of eosinophils to the site of injection (Beck, L. A. et al., *J. Immun.* 1997, 159, 2962-2972). Likewise, a RANTES antibody has demonstrated the ability to ameliorate the symptoms of disease in the rat Adjuvant induced arthritis (AIA) model (Barnes, D. A. et al., *J. Clin Invest.* 1998, 101, 2910-2919). Similar results were obtained when using a peptide derived antagonist of the RANTES/CCR-1 interaction in both the rat AIA (Shahrara, S. et al., *Arthritis & Rheum.* 2005, 52, 1907-1919) and the mouse CIA (Plater-Zyberk, C. et al., *Imm. Lett.* 1997, 57, 117-120) disease models of joint inflammation.

Recently, a number of groups have described the development of small molecule antagonists of MIP-1α (reviewed in: Carson, K. G. et al., *Ann. Reports Med. Chem.* 2004, 39, 149-158).

SUMMARY OF THE INVENTION

Accordingly, the present invention provides novel antagonists or partial agonists/antagonists of MIP-1α or CCR-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis and transplant rejection, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel acyclic derivatives for use in therapy.

The present invention provides the use of novel acyclic derivatives for the manufacture of a medicament for the treatment of inflammatory diseases.

These and other features of the invention, which will become apparent during the following detailed description, have been achieved by the inventors' discovery that compounds of formula (I):

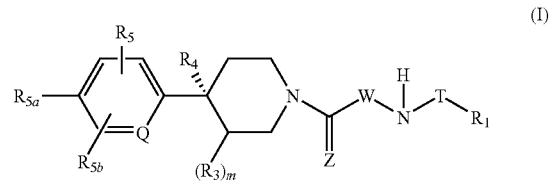

or stereoisomers or prodrugs or pharmaceutically acceptable salts thereof, wherein m, Q, T, W, Z, $R_1$, $R_3$, $R_4$, $R_5$, $R_{5a}$ and $R_{5b}$, are defined below, are effective modulators of MIP-1α and chemokine activity.

DETAILED DESCRIPTION OF THE PRESENT INVENTION

In one embodiment, the present invention provides novel compounds of formula (I):

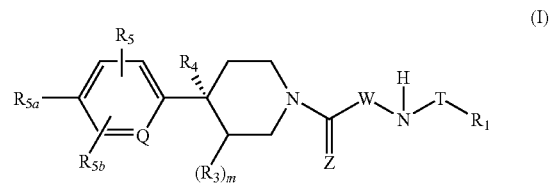

or a stereoisomer or pharmaceutically acceptable salt from thereof, wherein:
Q is CH or N;
Z is O or S;
W is —$CR_{3a}R_{3a}CR_{3b}R_{3b}$—;
T is a bond,

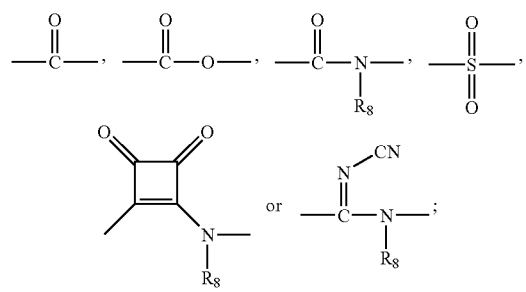

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O$(CR_8R_8)_rR_{10}$, —O$(CF_2)_rCF_3$, —O$(CR_8R_8)_rR_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —(CR$_8$R$_8$)$_r$OH, —(CR$_8$R$_8$)$_r$CN, —(CR$_8$R$_8$)$_r$OR$_6$, —(CR$_8$R$_8$)$_r$C(=O)R$_6$, —(CR$_8$R$_8$)$_r$OC(=O)NH$_2$, —(CR$_8$R$_8$)$_r$OC(=O)NHR$_6$, —(CR$_8$R$_8$)$_r$OC(=O)NR$_6$R$_6$, —(CR$_8$R$_8$)$_r$NH$_2$, —(CR$_8$R$_8$)$_r$NHR$_6$, —(CR$_8$R$_8$)$_r$NR$_6$R$_6$, —(CR$_8$R$_8$)$_r$NHC(=O)R$_6$, —(CR$_8$R$_8$)$_r$NHC(=O)NH$_2$, —(CR$_8$R$_8$)$_r$NHC(=O)NHR$_6$, —(CR$_8$R$_8$)$_r$NHC(=O)NR$_6$R$_6$, —(CR$_8$R$_8$)$_r$NHC(=O)OR$_6$, —(CR$_8$R$_8$)$_r$C(=O)NH$_2$, —(CR$_8$R$_8$)$_r$C(=O)NHR$_6$, —(CR$_8$R$_8$)$_r$C(=O)NR$_6$R$_6$ or —NHS(=O)$_2$R$_6$, wherein the alkyl may be optionally substituted with 0-3 fluorine atoms per carbon atom; provided that both R$_{3a}$'s can not be simultaneously attached via a heteroatom;

R$_{3b}$, at each occurrence, is independently hydrogen, alkyl, cycloalkyl, alkenyl, alkynyl, cycloalkylalkyl, silylalkyl, aryl, heteroaryl, arylalkyl or heteroarylalkyl, wherein the alkyl, cycloalkyl, alkenyl, alkynyl, cycloalkylalkyl, silylalkyl, aryl, heteroaryl, arylalkyl or heteroarylalkyl may be optionally substituted with 0-3 fluorine atoms per carbon atom, —OH, —CN, —OR$_6$, —OC(=O)R$_6$, —OC(=O)NH$_2$, —OC(=O)NHR$_6$, —OC(=O)NR$_6$R$_6$, —NH$_2$, —NHR$_6$, —NR$_6$R$_6$, —NHC(=O)R$_6$, —NHC(=O)NH$_2$, —NHC(=O)NHR$_6$, —NHC(=O)NR$_6$R$_6$, or —NHS(=O)$_2$R$_6$;

or the two R$_{3a}$'s or R$_{3b}$'s may be taken together with the carbon atom to which they are attached to form a 3- to 6-membered ring, wherein the carbon atoms of said ring may be optionally replaced with a heteroatom selected from N(R$_7$), O, and S;

R$_4$ is hydrogen, F, OH, CN or —NH$_2$;

R$_5$ is hydrogen, halo, alkyl, —CN or —Oalkyl;

R$_{5a}$ is hydrogen, halo, —CN or alkynyl;

R$_{5b}$ is hydrogen, halo, —CN, —Oalkyl or —C(=O)O(CR$_8$R$_8$)$_r$R$_{10}$;

R$_6$, at each occurrence, is independently alkyl, cycloalkyl, cycloalkylalkyl, aryl, arylalkyl, heteroaryl or heteroarylalkyl;

R$_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_9$R$_9$, —S(O)$_2$NR$_9$R$_9$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$ (CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$ NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and
r is 0-5;
provided that:
1) the compound is not a compound of the formula:

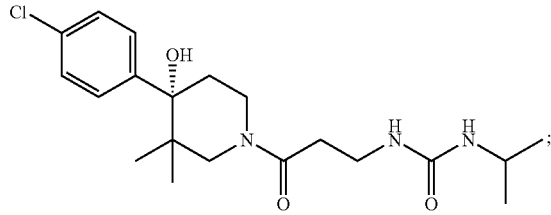 [SMILES: CC(C)NC(=O)NCCC(=O)N1CC[C@](O)(c2ccc(Cl)cc2)C(C)(C)C1]

2) m is not 0 or 1 when R$_1$ is not a nitrogenated aromatic monocyclic group or nitrogenated aromatic fused-ring group which has at least one hydroxyl and/or amino; and 3) R$_4$ is not hydrogen or CN when both R$_{3a}$'s and R$_{3b}$'s are hydrogen and R$_1$ is benzyl or phenylcyclopropyl.

In yet another embodiment, compounds of the present invention, or a stereoisomer or pharmaceutically acceptable salt from thereof, are those in which Q is CH.

In yet another embodiment, compounds of the present invention, or a stereoisomer or pharmaceutically acceptable salt from thereof, are those in which R$_{3b}$, at each occurrence, is independently alkyl, cycloalkyl, alkenyl, alkynyl, cycloalkylalkyl, silylalkyl, aryl, heteroaryl, arylalkyl or heteroarylalkyl, wherein the alkyl, cycloalkyl, alkenyl, alkynyl, cycloalkylalkyl, silylalkyl, aryl, heteroaryl, arylalkyl or heteroarylalkyl may be optionally substituted with 0-3 fluorine atoms per carbon atom, —OH, —CN, —OR$_6$, —OC(=O)R$_6$, —OC(=O)NH$_2$, —OC(=O)NHR$_6$, —OC(=O)NR$_6$R$_6$, —NH$_2$, —NHR$_6$, —NR$_6$R$_6$, —NHC(=O)R$_6$, —NHC(=O)NH$_2$, —NHC(=O)NHR$_6$, —NHC(=O)NR$_6$R$_6$, or —NHS(=O)$_2$R$_6$.

In another embodiment, compounds of the present invention, or a stereoisomer or pharmaceutically acceptable salt from thereof, are those in which the compound is a compound of formula (Ia):

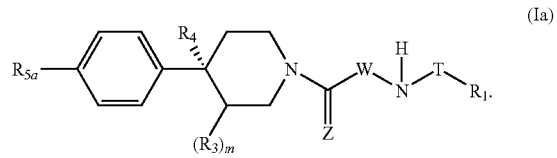

(Ia)

In yet another embodiment, compounds of the present invention, or a stereoisomer or pharmaceutically acceptable salt from thereof, are those in which:

Z is O or S;
W is —CR$_{3a}$R$_{3a}$CR$_{3b}$R$_{3b}$—;
T is a bond,

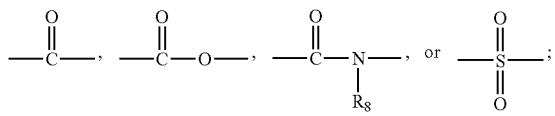

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —$(CR_8R_8)_r$OH, —$(CR_8R_8)_r$CN, —$(CR_8R_8)_r$OR$_6$, —$(CR_8R_8)_r$C(=O)R$_6$, —$(CR_8R_8)_r$OC(=O)NH$_2$, —$(CR_8R_8)_r$OC(=O)NHR$_6$, —$(CR_8R_8)_r$OC(=O)NR$_6$R$_6$, —$(CR_8R_8)_r$NH$_2$, —$(CR_8R_8)_r$NHR$_6$, —$(CR_8R_8)_r$NR$_6$R$_6$, —$(CR_8R_8)_r$NHC(=O)R$_6$, —$(CR_8R_8)_r$NHC(=O)NH$_2$, —$(CR_8R_8)_r$NHC(=O)NHR$_6$, —$(CR_8R_8)_r$NHC(=O)NR$_6$R$_6$, —$(CR_8R_8)_r$NHC(=O)OR$_6$, —$(CR_8R_8)_r$C(=O)NH$_2$, —$(CR_8R_8)_r$C(=O)NHR$_6$, or —$(CR_8R_8)_r$C(=O)NR$_6$R$_6$, wherein the alkyl may be optionally substituted with 0-3 fluorine atoms per carbon atom; provided that both $R_{3a}$'s can not be simultaneously attached via a heteroatom;

$R_{3b}$, at each occurrence, is independently hydrogen, alkyl, cycloalkyl, alkenyl, alkynyl, cycloalkylalkyl, silylalkyl, aryl or arylalkyl, wherein the alkyl, cycloalkyl, alkenyl, alkynyl, cycloalkylalkyl, silylalkyl, aryl or arylalkyl, may be optionally substituted with 0-3 fluorine atoms per carbon atom, —OH, —CN, —OR$_6$, —OC(=O)R$_6$, —OC(=O)NH$_2$, —OC(=O)NHR$_6$, —OC(=O)NR$_6$R$_6$, —NH$_2$, —NHR$_6$, —NR$_6$R$_6$, —NHC(=O)R$_6$, —NHC(=O)NH$_2$, —NHC(=O)NHR$_6$, —NHC(=O)NR$_6$R$_6$, or —NHS(=O)$_2$R$_6$;

or the two $R_{3a}$'s or $R_{3b}$'s may be taken together with the carbon atom to which they are attached to form a 3- to 6-membered ring, wherein the carbon atoms of said ring may be optionally replaced with a heteroatom selected from N(R$_7$), O, and S;

$R_4$ is F, OH, CN or —NH$_2$;

$R_5$ is hydrogen, alkyl, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_9$R$_9$, —S(O)$_2$NR$_9$R$_9$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 0-2; and r is 0-4.

In yet another embodiment, compounds of the present invention, or a stereoisomer or pharmaceutically acceptable salt from thereof, are those in which:

Z is O or S;

W is —CR$_{3a}$R$_{3a}$CR$_{3b}$R$_{3b}$—;

T is a bond,

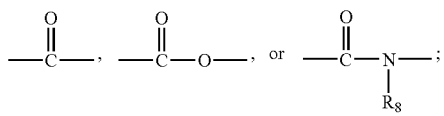

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O (CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O (CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_3$, at each occurrence, is independently OH or alkyl; or two R$_3$'s together with the carbon atom to which they are attached may form a 3- to 6-membered ring;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —(CR$_8$R$_8$)$_r$OH, —(CR$_8$R$_8$)$_r$CN, —(CR$_8$R$_8$)$_r$OR$_6$, —(CR$_8$R$_8$)$_r$OC(=O)R$_6$, —(CR$_8$R$_8$)$_r$OC(=O)NH$_2$, —(CR$_8$R$_8$)$_r$OC(=O)NHR$_6$, —(CR$_8$R$_8$)$_r$OC(=O)NR$_6$R$_6$, —(CR$_8$R$_8$)$_r$NH$_2$, —(CR$_8$R$_8$)$_r$NHR$_6$, —(CR$_8$R$_8$)$_r$NR$_6$R$_6$, —(CR$_8$R$_8$)$_r$NHC(=O)R$_6$, —(CR$_8$R$_8$)$_r$NHC(=O)NH$_2$, —(CR$_8$R$_8$)$_r$NHC(=O)NHR$_6$, —(CR$_8$R$_8$)$_r$C(=O)NH$_2$ or —(CR$_8$R$_8$)$_r$C(=O)NHR$_6$, wherein the alkyl may be optionally substituted with 0-3 fluorine atoms per carbon atom; provided that both R$_{3a}$'s can not be simultaneously attached via a heteroatom;

$R_{3b}$, at each occurrence, is independently hydrogen, alkyl, cycloalkyl, alkenyl, cycloalkylalkyl, silylalkyl or arylalkyl, wherein the alkyl, cycloalkyl, alkenyl, cycloalkylalkyl, silylalkyl or arylalkyl may be optionally substituted with 0-3 fluorine atoms per carbon atom, OH, —CN, —OR$_6$, —OC(=O)R$_6$, —OC(=O)NH$_2$, —OC(=O)NHR$_6$, —OC(=O)NR$_6$R$_6$, —NH$_2$, —NHR$_6$, —NR$_6$R$_6$, —NHC(=O)R$_6$, —NHC(=O)NH$_2$, —NHC(=O)NHR$_6$, —NHC(=O)NR$_6$R$_6$, or —NHS(=O)$_2$R$_6$;

or the two R$_{3a}$'s or R$_{3b}$'s may be taken together with the carbon atom to which they are attached to form a 3- to 6-membered ring, wherein the carbon atoms of said ring may be optionally replaced with a heteroatom selected from N(R$_7$), O, and S;

$R_4$ is F, OH or —NH$_2$;

$R_5$ is hydrogen, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_9$R$_9$, —S(O)$_2$NR$_9$R$_9$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$ or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with 0-3 R$_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O (CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O (CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 0-2; and r is 0-3.

In still yet another embodiment, compounds of the present invention, or a stereoisomer or pharmaceutically acceptable salt from thereof, are those in which:

Z is O;

W is —CR$_{3a}$R$_{3a}$CR$_{3b}$R$_{3b}$—;

T is

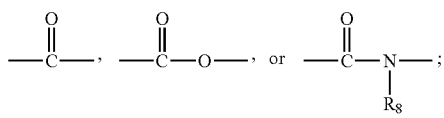

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —(CR$_8$R$_8$)$_r$OH, —(CR$_8$R$_8$)$_r$CN, —(CR$_8$R$_8$)$_r$OR$_6$, —(CR$_8$R$_8$)$_r$OC(=O)R$_6$, —(CR$_8$R$_8$)$_r$OC(=O)NH$_2$, —(CR$_8$R$_8$)$_r$OC(=O)NHR$_6$, —(CR$_8$R$_8$)$_r$OC(=O)NR$_6$R$_6$, —(CR$_8$R$_8$)$_r$NH$_2$, —(CR$_8$R$_8$)$_r$NHR$_6$, —(CR$_8$R$_8$)$_r$NR$_6$R$_6$, —(CR$_8$R$_8$)$_r$NHC(=O)R$_6$, —(CR$_8$R$_8$)$_r$NHC(=O)NH$_2$ or —(CR$_8$R$_8$)$_r$C(=O)NH$_2$, wherein the alkyl may be optionally substituted with 0-3 fluorine atoms per carbon atom; provided that both $R_{3a}$'s can not be simultaneously attached via a heteroatom;

$R_{3b}$, at each occurrence, is independently hydrogen, alkyl, cycloalkyl, alkenyl, cycloalkylalkyl or arylalkyl, wherein the alkyl, cycloalkyl, alkenyl, cycloalkylalkyl or arylalkyl may be optionally substituted with 0-3 fluorine atoms per carbon atom, OH, —CN, —OR$_6$, —OC(=O)R$_6$, —OC(=O)NH$_2$, —OC(=O)NHR$_6$, —OC(=O)NR$_6$R$_6$, —NH$_2$, —NHR$_6$, —NR$_6$R$_6$, —NHC(=O)R$_6$, —NHC(=O)NH$_2$, —NHC(=O)NHR$_6$, —NHC(=O)NR$_6$R$_6$, or —NHS(=O)$_2$R$_6$;

or the two $R_{3a}$'s or $R_{3b}$'s may be taken together with the carbon atom to which they are attached to form a 3- to 6-membered ring, wherein the carbon atoms of said ring may be optionally replaced with a heteroatom selected from N(R$_7$), O, and S;

$R_4$ is F, OH, or —NH$_2$;

$R_5$ is hydrogen, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_9$R$_9$, —S(O)$_2$NR$_9$R$_9$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)

$(CR_8R_8)_rR_{10}$, —$S(O)_2(CR_8R_8)_rR_{10}$, —$NR_9C(=O)OR_6$, —$NR_9S(O_2)R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —$C(=O)O(CR_8R_8)_rR_{10}$, —OH, —SH, —$C(=O)NR_{14}R_{14}$, —$S(O)_2NR_{14}R_{14}$, —$C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —$C(=O)(CR_8R_8)_rR_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —$C(=O)OH$, —$C(=O)O(CR_8R_8)_rR_{14}$, —$O(CF_2)_rCF_3$, —$O(CR_8R_8)_rR_{14}$, —OH, —SH, —$S(CR_8R_8)_rR_{14}$, —$S(O)_3H$, —$C(=O)NR_{14}R_{14}$, —$NR_{14}R_{14}$, —$S(O)_2NR_{14}R_{14}$, —$NR_{14}S(O)_2(CF_2)_rCF_3$, —$C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —$C(=O)(CR_8R_8)_rR_{14}$, —$NR_{14}C(=O)H$, —$NR_{14}C(=O)(CR_8R_8)_rR_{14}$, —$OC(=O)(CR_8R_8)_rR_{14}$, —$S(=O)(CR_8R_8)_rR_{14}$, —$S(O)_2(CR_8R_8)_rR_{14}$, —$NR_{14}C(=O)OR_6$, —$NR_{14}S(O_2)R_6$, —$OC(=O)NR_{14}R_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —$C(=O)OH$, —$C(=O)O(CR_8R_8)_rR_{14}$, —$O(CF_2)_rCF_3$, —$O(CR_8R_8)_rR_{14}$, —OH, —SH, —$S(CR_8R_8)_rR_{14}$, —$S(O)_3H$, —$C(=O)NR_{14}R_{14}$, —$NR_{14}R_{14}$, —$S(O)_2NR_{14}R_{14}$, —$NR_{14}S(O)_2(CF_2)_rCF_3$, —$C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —$C(=O)(CR_8R_8)_rR_{14}$, —$NR_{14}C(=O)H$, —$NR_{14}C(=O)(CR_8R_8)_rR_{14}$, —$OC(=O)(CR_8R_8)_rR_{14}$, —$S(=O)(CR_8R_8)_rR_{14}$, —$S(O)_2(CR_8R_8)_rR_{14}$, —$NR_{14}C(=O)OR_6$, —$NR_{14}S(O_2)R_6$, —$OC(=O)NR_{14}R_{14}$, aryloxy or arylalkyl;

$R_{14}$, at each occurrence, is independently selected from hydrogen, alkyl, cycloalkyl or phenyl;

m is 0-2; and r is 0-2.

In one embodiment, compounds of the present invention, or a stereoisomer or pharmaceutically acceptable salt from thereof, are those in which:

Z is O;

W is —$CR_{3a}R_{3a}CR_{3b}R_{3b}$—;

T is $$-\overset{O}{\underset{\|}{C}}-,\quad -\overset{O}{\underset{\|}{C}}-O-,\quad \text{or}\quad -\overset{O}{\underset{\|}{C}}-\underset{\underset{R_8}{|}}{N}-;$$

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —$C(=O)OH$, —$C(=O)O(CR_8R_8)_rR_{10}$, —$O(CF_2)_rCF_3$, —$O(CR_8R_8)_rR_{10}$, —OH, —SH, —$S(CR_8R_8)_rR_{10}$, —$C(=O)NR_9R_9$, —$NR_9R_9$, —$S(O)_2NR_9R_9$, —$NR_9S(O)_2(CF_2)_rCF_3$, —$C(=O)NR_9S(O)_2R_6$, —$S(O)_2NR_9C(=O)OR_6$, —$S(O)_2NR_9C(=O)NR_9R_9$, —$C(=O)NR_9S(O)_2(CF_2)_rCF_3$, —$C(=O)(CR_8R_8)_rR_{10}$, —$NR_9C(=O)H$, —$NR_9C(=O)(CR_8R_8)_rR_{10}$, —$OC(=O)(CR_8R_8)_rR_{10}$, —$S(=O)(CR_8R_8)_rR_{10}$, —$S(O)_2(CR_8R_8)_rR_{10}$, —$NR_9C(=O)OR_6$, —$NR_9S(O_2)R_6$, =O, —$OC(=O)NR_9R_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —$C(=O)O(CR_8R_8)_rR_{10}$, —OH, —SH, —$C(=O)NR_{14}R_{14}$, —$S(O)_2NR_{14}R_{14}$, —$C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —$C(=O)(CR_8R_8)_rR_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —$C(=O)OH$, —$C(=O)O(CR_8R_8)_rR_{10}$, —$O(CF_2)_rCF_3$, —$O(CR_8R_8)_rR_{10}$, —OH, —SH, —$S(CR_8R_8)_rR_{10}$, —$C(=O)NR_9R_9$, —$NR_9R_9$, —$S(O)_2NR_9R_9$, —$NR_9S(O)_2(CF_2)_rCF_3$, —$C(=O)NR_9S(O)_2R_6$, —$S(O)_2NR_9C(=O)OR_6$, —$S(O)_2NR_9C(=O)NR_9R_9$, —$C(=O)NR_9S(O)_2(CF_2)_rCF_3$, —$C(=O)(CR_8R_8)_rR_{10}$, —$NR_9C(=O)H$, —$NR_9C(=O)(CR_8R_8)_rR_{10}$, —$OC(=O)(CR_8R_8)_rR_{10}$, —$S(=O)(CR_8R_8)_rR_{10}$, —$S(O)_2(CR_8R_8)_rR_{10}$, —$NR_9C(=O)OR_6$, —$NR_9S(O_2)R_6$, aryloxy, arylalkyl or arylalkyloxyalkyl;

$R_3$, at each occurrence, is independently OH or alkyl;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —$(CR_8R_8)_rOH$, —$(CR_8R_8)_rCN$, —$(CR_8R_8)_rOR_6$, —$(CR_8R_8)_rC(=O)R_6$, —$(CR_8R_8)_rOC(=O)NH_2$, —$(CR_8R_8)_rOC(=O)NHR_6$, —$(CR_8R_8)_rOC(=O)NR_6R_6$, —$(CR_8R_8)_rNH_2$, —$(CR_8R_8)_rNHR_6$, —$(CR_8R_8)_rNR_6R_6$ or —$(CR_8R_8)_rC(=O)NH_2$, wherein the alkyl may be optionally substituted with 0-3 fluorine atoms per carbon atom; provided that both $R_{3a}$'s can not be simultaneously attached via heteroatom;

$R_{3b}$, at each occurrence, is independently hydrogen, alkyl, cycloalkyl, alkenyl or arylalkyl, wherein the alkyl, cycloalkyl, alkenyl or arylalkyl may be optionally substituted with 0-3 fluorine atoms per carbon atom, OH, CN, —$OR_6$, —$OC(=O)R_6$, —$OC(=O)NH_2$, —$OC(=O)NHR_6$, —OC (=O)NR$_6$R$_6$, —NH$_2$, —NHR$_6$, —NR$_6$R$_6$, —NHC(=O)R$_6$, —NHC(=O)NH$_2$, —NHC(=O)NHR$_6$ or —NHC(=O)NR$_6$R$_6$;

or the two R$_{3a}$'s or R$_{3b}$'s may be taken together with the carbon atom to which they are attached to form a 3- to 6-membered ring, wherein the carbon atoms of said ring may be optionally replaced with a heteroatom selected from N(R$_7$), O, and S;

R$_4$ is F, OH or —NH$_2$;

R$_5$ is hydrogen, halo or —CN;

R$_{5a}$ is halo or —CN;

R$_{5b}$ is hydrogen, halo or —CN;

R$_6$, at each occurrence, is independently alkyl, cycloalkyl, cycloalkylalkyl, aryl, arylalkyl, heteroaryl or heteroarylalkyl;

R$_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_9$R$_9$, —S(O)$_2$NR$_9$R$_9$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-2.

In another embodiment, compounds of the present invention, or a stereoisomer or pharmaceutically acceptable salt form thereof, are those in which:

Z is O;

W is —CR$_{3a}$R$_{3a}$CR$_{3b}$R$_{3b}$—;

T is

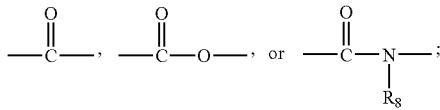

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)

$OR_6$, $-S(O)_2NR_{14}C(=O)NR_{14}R_{14}$, $-C(=O)NR_{14}S(O)_2$ $(CF_2)_rCF_3$, $-C(=O)(CR_8R_8)_rR_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-CN$, $-NO_2$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-S(=O)(CR_8R_8)_rR_{10}$, $-S(O)_2(CR_8R_8)_rR_{10}$, $-NR_9C(=O)OR_6$, $-NR_9S(O_2)R_6$, aryloxy, arylalkyl or arylalkyloxyalkyl;

$R_3$, at each occurrence, is independently OH or alkyl;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, $-(CR_8R_8)_rOH$, $-(CR_8R_8)_rCN$, $-(CR_8R_8)_rOR_6$, $-(CR_8R_8)_rC(=O)R_6$, $-(CR_8R_8)_rOC(=O)NH_2$, $-(CR_8R_8)_rOC(=O)NHR_6$, $-(CR_8R_8)_rOC(=O)NR_6R_6$ or $-(CR_8R_8)_rNH_2$, wherein the alkyl may be optionally substituted with 0-3 fluorine atoms per carbon atom; provided that both $R_{3a}$'s can not be simultaneously attached via a heteroatom;

$R_{3b}$, at each occurrence, is independently hydrogen, alkyl, cycloalkyl or alkenyl, wherein the alkyl, cycloalkyl or alkenyl, may be optionally substituted with 0-3 fluorine atoms per carbon atom, $-OH$, $-CN$, $-OR_6$, $-OC(=O)R_6$, $-OC(=O)NH_2$, $-OC(=O)NHR_6$, $-OC(=O)NR_6R_6$, $-NH_2$, $-NHR_6$, $-NR_6R_6$, $-NHC(=O)R_6$, or $-NHC(=O)NH_2$;

or the two $R_{3a}$'s or $R_{3b}$'s may be taken together with the carbon atom to which they are attached to form a 3- to 6-membered ring, wherein the carbon atoms of said ring may be optionally replaced with a heteroatom selected from $N(R_7)$, O, and S;

$R_4$ is F or OH;

$R_5$ is hydrogen, halo or $-CN$;

$R_{5a}$ is halo or $-CN$;

$R_{5b}$ is hydrogen, halo or $-CN$;

$R_6$, at each occurrence, is independently alkyl, cycloalkyl, cycloalkylalkyl, aryl, arylalkyl, heteroaryl or heteroarylalkyl;

$R_7$ is hydrogen, alkyl, haloalkyl, aryl, alkenyl, alkynyl, cycloalkyl, cycloalkylalkyl, heteroaryl, heteroarylalkyl, heterocyclyl heterocyclylalkyl, $-C(=O)O(CR_8R_8)_rR_{10}$, $-OH$, $-SH$, $-C(=O)NR_9R_9$, $-S(O)_2NR_9R_9$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-CN$, $-NO_2$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-S(=O)(CR_8R_8)_rR_{10}$, $-S(O)_2(CR_8R_8)_rR_{10}$, $-NR_9C(=O)OR_6$, $-NR_9S(O_2)R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, $-C(=O)O(CR_8R_8)_rR_{10}$, $-OH$, $-SH$, $-C(=O)NR_{14}R_{14}$, $-S(O)_2NR_{14}R_{14}$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-CN$, $-NO_2$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-S(=O)(CR_8R_8)_rR_{14}$, $-S(O)_2(CR_8R_8)_rR_{14}$, $-NR_{14}C(=O)OR_6$, $-NR_{14}S(O_2)R_6$, $-OC(=O)NR_{14}R_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-CN$, $-NO_2$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-S(=O)(CR_8R_8)_rR_{14}$, $-S(O)_2(CR_8R_8)_rR_{14}$, $-NR_{14}C(=O)OR_6$, $-NR_{14}S(O_2)R_6$, $-OC(=O)NR_{14}R_{14}$, aryloxy or arylalkyl;

$R_{14}$, at each occurrence, is independently selected from hydrogen, alkyl, cycloalkyl or phenyl;

m is 0-2; and r is 0-2.

In yet another embodiment, compounds of the present invention, or a stereoisomer or pharmaceutically acceptable salt from thereof, are those in which:

Z is O;

W is $-CR_{3a}R_{3a}CR_{3b}R_{3b}-$;

T is $$-\overset{O}{\underset{\|}{C}}-, \quad -\overset{O}{\underset{\|}{C}}-O-, \quad \text{or} \quad -\overset{O}{\underset{\|}{C}}-\underset{R_8}{N}-;$$

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

$R_3$, at each occurrence, is independently OH or alkyl;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —(CR$_8$R$_8$)$_r$OH, —(CR$_8$R$_8$)$_r$CN, —(CR$_8$R$_8$)$_r$OR$_6$, —(CR$_8$R$_8$)$_r$OC(=O)R$_6$, —(CR$_8$R$_8$)$_r$OC(=O)NH$_2$, or —(CR$_8$R$_8$)$_r$C(=O)NHR$_6$, wherein the alkyl may be optionally substituted with 0-3 fluorine atoms per carbon atom; provided that both $R_{3a}$'s can not be simultaneously attached via a heteroatom;

$R_{3b}$, at each occurrence, is independently hydrogen, alkyl or cycloalkyl, wherein the alkyl or cycloalkyl may be optionally substituted with 0-3 fluorine atoms per carbon atom, —OH, —CN, —OR$_6$, —OC(=O)R$_6$, —OC(=O)NH$_2$, —OC(=O)NHR$_6$, —OC(=O)NR$_6$R$_6$, —NH$_2$, —NHR$_6$, —NR$_6$R$_6$, —NHC(=O)R$_6$, or —NHC(=O)NH$_2$;

$R_4$ is F or OH;

$R_5$ is hydrogen, halo or —CN;

$R_{5a}$ is halo or —CN;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 0-2; and r is 0-2.

In still yet another embodiment, compounds of the present invention, or a stereoisomer or pharmaceutically acceptable salt from thereof, are those in which:

Z is O;

W is —CR$_{3a}$R$_{3a}$CR$_{3b}$R$_{3b}$—;

T is $$-\overset{O}{\underset{\|}{C}}-, \quad -\overset{O}{\underset{\|}{C}}-O-, \quad \text{or} \quad -\overset{O}{\underset{\|}{C}}-\underset{R_8}{N}-;$$

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, cycloalkyl, cycloalkylalkyl, heteroaryl, heteroarylalkyl, heterocyclyl heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$;

$R_{1b}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_3$, at each occurrence, is independently OH or alkyl;

$R_{3a}$, at each occurrence, is independently hydrogen, alkyl, cycloalkyl, alkenyl, cycloalkylalkyl, silylalkyl, aryl, arylalkyl, heteroaryl, heteroarylalkyl, OH, —OR$_6$ or —OC(=O)R$_6$, wherein the alkyl may be optionally substituted with 0-3 fluorine atoms per carbon atom;

$R_{3b}$, at each occurrence, is independently hydrogen, alkyl or cycloalkyl, wherein the alkyl or cycloalkyl may be optionally substituted with 0-3 fluorine atoms per carbon atom, —OH, —CN, —OR$_6$, —OC(=O)R$_6$, —OC(=O)NH$_2$, —OC(=O)NHR$_6$, —OC(=O)NR$_6$R$_6$, or —NH$_2$;

$R_4$ is OH;

$R_5$ is hydrogen or halo;

$R_{5a}$ is halo or —CN;

$R_{5b}$ is hydrogen or halo;

$R_6$, at each occurrence, is independently alkyl, cycloalkyl, aryl or heteroaryl;

$R_8$, at each occurrence, is independently hydrogen or alkyl;

$R_9$, at each occurrence, is independently hydrogen, alkyl, cycloalkyl, aryl, heteroaryl or heterocyclyl, wherein the aryl, heteroaryl or heterocyclyl may be optionally substituted with 0-5 $R_{9a}$, and the heteroaryl or heterocyclyl contain 1-4 heteroatoms selected from N, O, and S;

$R_{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{10}$, at each occurrence, is independently selected from alkyl, aryl or heterocyclyl, wherein the aryl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 0-2; and r is 0-2.

In one embodiment, compounds of the present invention, or a stereoisomer or pharmaceutically acceptable salt from thereof, are those in which:

Z is O;

W is —CR$_{3a}$R$_{3a}$CR$_{3b}$R$_{3b}$—;

T is $$-\overset{O}{\underset{\|}{C}}-, \quad -\overset{O}{\underset{\|}{C}}-O-, \quad \text{or} \quad -\overset{O}{\underset{\|}{C}}-\underset{R_8}{N}-;$$

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, or aryloxy, wherein the alkyl, aryl, cycloalkyl, heteroaryl, heterocyclyl and aryloxy may be optionally substituted with 0-3 $R_{1b}$;

$R_{1b}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, or aryloxy;

$R_3$, at each occurrence, is independently OH or alkyl;

$R_{3a}$, at each occurrence, is independently hydrogen, alkyl, cycloalkyl, alkenyl, cycloalkylalkyl, silylalkyl, aryl, arylalkyl, heteroaryl or heteroarylalkyl, wherein the alkyl may be optionally substituted with 0-3 fluorine atoms per carbon atom;

$R_{3b}$, at each occurrence, is independently hydrogen, alkyl or cycloalkyl, wherein the alkyl or cycloalkyl may be optionally substituted with 0-3 fluorine atoms per carbon atom, —OH, —CN, —OR$_6$, —OC(=O)R$_6$, —OC(=O)NH$_2$, or —OC(=O)NHR$_6$;

$R_4$ is OH;

$R_5$ is hydrogen or halo;

$R_{5a}$ is halo;

$R_{5b}$ is hydrogen or halo;

$R_6$, at each occurrence, is independently alkyl, cycloalkyl, aryl or heteroaryl;

$R_8$, at each occurrence, is independently hydrogen or alkyl;

$R_9$, at each occurrence, is independently hydrogen, alkyl, cycloalkyl, aryl, heteroaryl or heterocyclyl, wherein the aryl, heteroaryl or heterocyclyl may be optionally substituted with 0-5 $R_{9a}$, and the heteroaryl or heterocyclyl contain 1-4 heteroatoms selected from N, O, and S;

$R_{9a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, or aryloxy;

$R_{10}$, at each occurrence, is independently selected from alkyl, aryl or heterocyclyl, wherein the aryl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, or aryloxy;

$R_{14}$, at each occurrence, is independently selected from hydrogen, alkyl, cycloalkyl or phenyl;

m is 0-2; and r is 0-2.

In another embodiment, compounds of the present invention, or a stereoisomer or pharmaceutically acceptable salt from thereof, are those in which:

Z is O;

W is —CR$_{3a}$R$_{3a}$CR$_{3b}$R$_{3b}$—;

T is

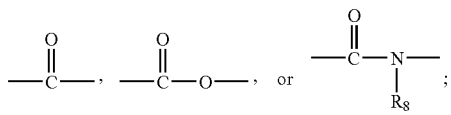

$R_1$ is alkyl, cycloalkyl, aryl or heteroaryl, all of which may be optionally substituted with 0-5 $R_{1a}$;

$R_{1a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, —OC(=O)NR$_9$R$_9$, or aryloxy, wherein the alkyl, aryl, cycloalkyl, heteroaryl, heterocyclyl and aryloxy may be optionally substituted with 0-3 $R_{1b}$;

$R_{1b}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, or aryloxy;

$R_3$, at each occurrence, is independently OH or alkyl;

$R_{3a}$, at each occurrence, is independently hydrogen, alkyl, cycloalkyl or alkenyl, wherein the alkyl may be optionally substituted with 0-3 fluorine atoms per carbon atom;

$R_{3b}$, at each occurrence, is independently hydrogen or alkyl, wherein the alkyl may be optionally substituted with 0-3 fluorine atoms per carbon atom, OH, —CN or —OR$_6$;

$R_4$ is OH;

$R_5$ is hydrogen or halo;

$R_{5a}$ is chloro;

$R_{5b}$ is hydrogen or halo;

$R_6$, at each occurrence, is independently alkyl, cycloalkyl, aryl or heteroaryl;

$R_8$, at each occurrence, is independently hydrogen or alkyl;

$R_9$, at each occurrence, is independently hydrogen, alkyl, cycloalkyl, aryl, heteroaryl or heterocyclyl, wherein the aryl, heteroaryl or heterocyclyl may be optionally substituted with 0-5 $R_{9a}$, and the heteroaryl or heterocyclyl contain 1-4 heteroatoms selected from N, O, and S;

$R_{9a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, or aryloxy;

$R_{10}$, at each occurrence, is independently selected from alkyl, aryl or heterocyclyl, wherein the aryl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, or aryloxy;

$R_{14}$, at each occurrence, is independently selected from hydrogen, alkyl, cycloalkyl or phenyl;

m is 0-2; and r is 0-2.

In another embodiment, compounds of the present invention, or a stereoisomer or pharmaceutically acceptable salt from thereof, are those in which:

Z is O;

W is —CR$_{3a}$R$_{3a}$CR$_{3b}$R$_{3b}$—;

T is

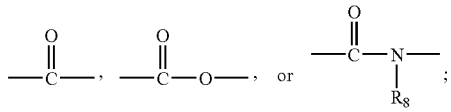

R₁ is alkyl, aryl or heteroaryl, all of which may be optionally substituted with 0-5 $R_{1a}$;

$R_{1a}$, at each occurrence, is independently selected from alkyl, haloalkyl, aryl, cycloalkyl, heteroaryl, heterocyclyl, halo, —CN, —NO₂, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —S(=O)(CR₈R₈)ᵣR₁₀, —S(O)₂(CR₈R₈)ᵣR₁₀, —NR₉C(=O)OR₆, —NR₉S(O₂)R₆, or —OC(=O)NR₉R₉, wherein the alkyl, aryl, cycloalkyl, heteroaryl and heterocyclyl may be optionally substituted with 0-3 $R_{1b}$;

$R_{1b}$, at each occurrence, is independently selected from alkyl, haloalkyl, aryl, cycloalkyl, heteroaryl, heterocyclyl, halo, —CN, —NO₂, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —S(=O)(CR₈R₈)ᵣR₁₀, —S(O)₂(CR₈R₈)ᵣR₁₀, —NR₉C(=O)OR₆, or —NR₉S(O₂)R₆;

$R_3$, at each occurrence, is alkyl;

$R_{3a}$, at each occurrence, is independently hydrogen or alkyl, wherein the alkyl may be optionally substituted with 0-3 fluorine atoms per carbon atom;

$R_{3b}$, at each occurrence, is independently hydrogen or alkyl, wherein the alkyl may be optionally substituted with 0-3 fluorine atoms per carbon atom;

$R_4$ is OH;

$R_5$ is hydrogen or halo;

$R_{5a}$ is chloro;

$R_{5b}$ is hydrogen or halo;

$R_6$, at each occurrence, is independently alkyl, cycloalkyl, aryl or heteroaryl;

$R_8$, at each occurrence, is independently hydrogen or alkyl;

$R_9$, at each occurrence, is independently hydrogen, alkyl, cycloalkyl, aryl, heteroaryl or heterocyclyl, wherein the aryl, heteroaryl or heterocyclyl may be optionally substituted with 0-5 $R_{9a}$, and the heteroaryl or heterocyclyl contain 1-4 heteroatoms selected from N, O, and S;

$R_{9a}$, at each occurrence, is independently selected from alkyl, haloalkyl, aryl, cycloalkyl, heteroaryl, heterocyclyl, halo, —CN, —NO₂, —C(=O)O(CR₈R₈)ᵣR₁₄, —O(CF₂)ᵣCF₃, —O(CR₈R₈)ᵣR₁₄, —OH, —SH, —S(CR₈R₈)ᵣR₁₄, —C(=O)NR₁₄R₁₄, —NR₁₄R₁₄, —S(O)₂NR₁₄R₁₄, —NR₁₄S(O)₂(CF₂)ᵣCF₃, —C(=O)NR₁₄S(O)₂R₆, —S(O)₂NR₁₄C(=O)OR₆, —S(O)₂NR₁₄C(=O)NR₁₄R₁₄, —C(=O)NR₁₄S(O)₂(CF₂)ᵣCF₃, —C(=O)(CR₈R₈)ᵣR₁₄, —NR₁₄C(=O)H, —NR₁₄C(=O)(CR₈R₈)ᵣR₁₄, —OC(=O)(CR₈R₈)ᵣR₁₄, —S(=O)(CR₈R₈)ᵣR₁₄, —S(O)₂(CR₈R₈)ᵣR₁₄, —NR₁₄C(=O)OR₆, —NR₁₄S(O₂)R₆, or —OC(=O)NR₁₄R₁₄;

$R_{10}$, at each occurrence, is independently selected from alkyl, aryl or heterocyclyl, wherein the aryl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, heteroaryl, heterocyclyl, halo, —CN, —NO₂, —C(=O)O(CR₈R₈)ᵣR₁₄, —O(CF₂)ᵣCF₃, —O(CR₈R₈)ᵣR₁₄, —OH, —SH, —S(CR₈R₈)ᵣR₁₄, —C(=O)NR₁₄R₁₄, —NR₁₄R₁₄, —S(O)₂NR₁₄R₁₄, —NR₁₄S(O)₂(CF₂)ᵣCF₃, —C(=O)NR₁₄S(O)₂R₆, —S(O)₂NR₁₄C(=O)OR₆, —S(O)₂NR₁₄C(=O)NR₁₄R₁₄, —C(=O)NR₁₄S(O)₂(CF₂)ᵣCF₃, —C(=O)(CR₈R₈)ᵣR₁₄, —NR₁₄C(=O)H, —NR₁₄C(=O)(CR₈R₈)ᵣR₁₄, —OC(=O)(CR₈R₈)ᵣR₁₄, —S(=O)(CR₈R₈)ᵣR₁₄, —S(O)₂(CR₈R₈)ᵣR₁₄, —NR₁₄C(=O)OR₆, —NR₁₄S(O₂)R₆, or —OC(=O)NR₁₄R₁₄;

$R_{14}$, at each occurrence, is independently selected from hydrogen, alkyl, cycloalkyl or phenyl;

m is 0-2; and r is 0-2.

In one embodiment, compounds of the present invention, or a stereoisomer or pharmaceutically acceptable salt from thereof, are those in which:

Z is O;

W is —CR₃ₐR₃ₐCR₃ᵦR₃ᵦ—;

T is

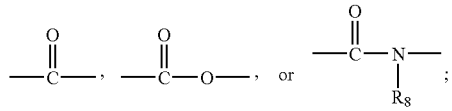

R₁ is alkyl or phenyl, both of which may be optionally substituted with 0-5 $R_{1a}$;

$R_{1a}$, at each occurrence, is independently selected from alkyl, haloalkyl, aryl, cycloalkyl, heteroaryl, heterocyclyl, halo, —NH₂, —CN, —NO₂, —C(=O)OH, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —C(=NR₁₄)NR₉R₉, —NHC(=NR₁₄)NR₁₄R₁₄, —S(=O)(CR₈R₈)ᵣR₁₀, —S(O)₂(CR₈R₈)ᵣR₁₀, —NR₉C(=O)OR₈, —NR₉S(O₂)R₈ or aryloxy, wherein the alkyl, aryl, cycloalkyl, heteroaryl, heterocyclyl or aryloxy may be optionally substituted with 0-3 $R_{1b}$;

$R_{1b}$, at each occurrence, is independently selected from alkyl, haloalkyl, aryl, cycloalkyl, heteroaryl, heterocyclyl, halo, —NH₂, —CN, —NO₂, —C(=O)OH, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —C(=NR₁₄)NR₉R₉, —NHC(=NR₁₄)NR₁₄R₁₄, —S(=O)(CR₈R₈)ᵣR₁₀, —S(O)₂(CR₈R₈)ᵣR₁₀, —NR₉C(=O)OR₈, —NR₉S(O₂)R₈, or aryloxy;

$R_3$ is methyl;

$R_{3a}$, at each occurrence, is independently hydrogen or alkyl, wherein the alkyl may be optionally substituted with 0-3 fluorine atoms per carbon atom;

$R_{3b}$, at each occurrence, is independently hydrogen or alkyl, wherein the alkyl may be optionally substituted with 0-3 fluorine atoms per carbon atom;

$R_4$ is OH;

$R_5$ is hydrogen or halo;

$R_{5a}$ is chloro;

$R_{5b}$ is hydrogen or halo;

$R_6$, at each occurrence, is independently alkyl, cycloalkyl, aryl or heteroaryl;

$R_8$, at each occurrence, is independently hydrogen or alkyl;

$R_9$, at each occurrence, is independently hydrogen, alkyl, cycloalkyl, aryl, heteroaryl or heterocyclyl, wherein the aryl, heteroaryl or heterocyclyl may be optionally substituted with 0-5 $R_{9a}$, and the heteroaryl or heterocyclyl contain 1-4 heteroatoms selected from N, O, and S;

$R_{9a}$, at each occurrence, is independently selected from alkyl, haloalkyl, aryl, cycloalkyl, heteroaryl, heterocyclyl, halo, —NH$_2$, —CN, —NO$_2$, —C(═O)OH, —C(═O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(═O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(═O)NR$_{14}$S(O)$_2$R$_6$, —S(O)$_2$NR$_{14}$C(═O)OR$_6$, —S(O)$_2$NR$_{14}$C(═O)NR$_{14}$R$_{14}$, —C(═O)NR$_{14}$S(O)$_2$(CF$_2$)$_r$CF$_3$, —C(═O)(CR$_8$R$_8$)$_r$R$_{14}$, —NR$_{14}$C(═O)H, —NR$_{14}$C(═O)(CR$_8$R$_8$)$_r$R$_{14}$, —OC(═O)(CR$_8$R$_8$)$_r$R$_{14}$, —C(═NR$_{14}$)NR$_{14}$R$_{14}$, —NHC(═NR$_{14}$)NR$_{14}$R$_{14}$, —S(═O)(CR$_8$R$_8$)$_r$R$_{14}$, —S(O)$_2$(CR$_8$R$_8$)$_r$R$_{14}$, —NR$_{14}$C(═O)OR$_8$, —NR$_{14}$S(O$_2$)R$_8$, or aryloxy;

$R_{10}$, at each occurrence, is independently selected from alkyl, aryl or heterocyclyl, wherein the aryl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, heteroaryl, heterocyclyl, halo, —NH$_2$, —CN, —NO$_2$, —C(═O)OH, —C(═O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(═O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(═O)NR$_{14}$S(O)$_2$R$_6$, —S(O)$_2$NR$_{14}$C(═O)OR$_6$, —S(O)$_2$NR$_{14}$C(═O)NR$_{14}$R$_{14}$, —C(═O)NR$_{14}$S(O)$_2$(CF$_2$)$_r$CF$_3$, —C(═O)(CR$_8$R$_8$)$_r$R$_{14}$, —NR$_{14}$C(═O)H, —NR$_{14}$C(═O)(CR$_8$R$_8$)$_r$R$_{14}$, —OC(═O)(CR$_8$R$_8$)$_r$R$_{14}$, —C(═NR$_{14}$)NR$_{14}$R$_{14}$, —NHC(═NR$_{14}$)NR$_{14}$R$_{14}$, —S(═O)(CR$_8$R$_8$)$_r$R$_{14}$, —S(O)$_2$(CR$_8$R$_8$)$_r$R$_{14}$, —NR$_{14}$C(═O)OR$_8$, —NR$_{14}$S(O$_2$)R$_8$ or aryloxy;

$R_{14}$, at each occurrence, is independently selected from hydrogen, alkyl, cycloalkyl or phenyl;

m is 2; and r is 0-2.

In one embodiment, compounds of Formula (I), or a stereoisomer or pharmaceutically acceptable salt from thereof, are those compounds exemplified in the examples.

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-1 receptor activity comprising administering to a patient in need thereof a therapeutically effective amount of a compound of the present invention.

In another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of the present invention.

In another embodiment, the present invention is directed to a method for treating inflammatory bowel disease, comprising administering to a patient in need thereof a therapeutically effective amount of a compound of the present invention.

In another embodiment, the present invention is directed to a method for treating Crohn's disease, comprising administering to a patient in need thereof a therapeutically effective amount of a compound of the present invention.

In another embodiment, the present invention is directed to a method for treating psoriasis, comprising administering to a patient in need thereof a therapeutically effective amount of a compound of the present invention.

In another embodiment, the present invention is directed to a method for treating systemic lupus erythematosus, comprising administering to a patient in need thereof a therapeutically effective amount of a compound of the present invention.

In another embodiment, the present invention is directed to a method for treating multiple sclerosis, comprising administering to a patient in need thereof a therapeutically effective amount of a compound of the present invention.

In another embodiment, the present invention is directed to a method for treating rheumatoid arthritis, comprising administering to a patient in need thereof a therapeutically effective amount of a compound of the present invention.

In another embodiment, the present invention is directed to a method for treating psoriatic arthritis, comprising administering to a patient in need thereof a therapeutically effective amount of a compound of the present invention.

In another embodiment, the present invention is directed to a method for treating multiple myeloma, comprising administering to a patient in need thereof a therapeutically effective amount of a compound of the present invention.

In another embodiment, the present invention is directed to a method for treating allergies, for example, skin and mast cell degranulation in eye conjunctiva, comprising administering to a patient in need thereof a therapeutically effective amount of a compound of the present invention.

In another embodiment, the present invention is directed to a method for treating hepatocellular carcinoma, comprising administering to a patient in need thereof a therapeutically effective amount of a compound of the present invention.

In another embodiment, the present invention is directed to a method for treating osteoporosis, comprising administering to a patient in need thereof a therapeutically effective amount of a compound of the present invention.

In another embodiment, the present invention is directed to a method for treating renal fibrosis, comprising administering to a patient in need thereof a therapeutically effective amount of a compound of the present invention.

In another embodiment, the present invention is directed to a method for treating inflammatory diseases, for example, inflammatory diseases which are at least partially mediated by CCR-1, comprising administering to a patient in need thereof a therapeutically effective amount of a compound of the present invention.

In another embodiment, the present invention is directed to a method for modulation of CCR1 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-1 receptor activity comprising administering to a patient in need thereof a therapeutically effective amount of a pharmaceutical composition comprised of a compound of the present invention and one or more active ingredients.

In yet another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-1, comprising administering to a patient in need thereof a therapeutically effective amount of a pharmaceutical composition comprised of a compound of present invention and one or more active ingredients.

In another embodiment, the present invention is directed to a method for modulation of CCR-1 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent as known to one of ordinary skill in the art.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., ═O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

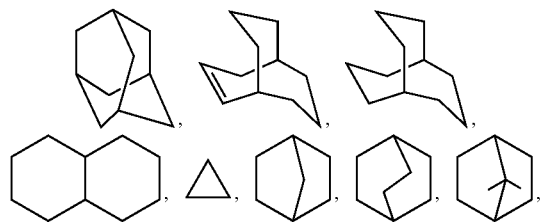

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example CF$_3$, having the specified number of carbon atoms, substituted with 1 or more halogen (for example —C$_v$F$_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings, for example:

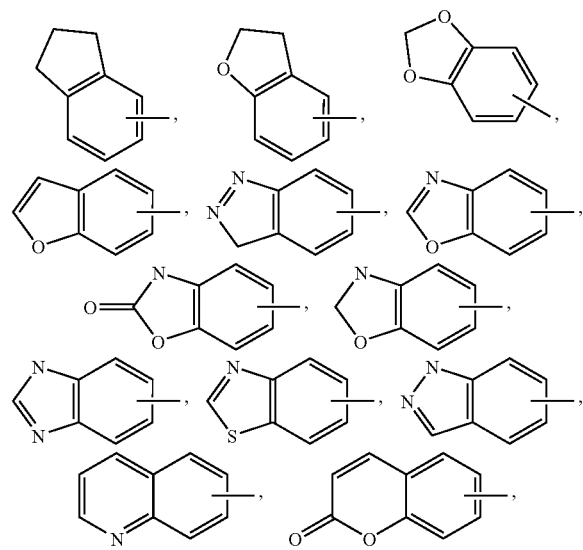

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the R$^1$ groups or substituents for R$^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —$NO_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., p. 1418 (Mack Publishing Company, Easton, Pa., 1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31, (Academic Press, 1996);

b) *Design of Prodrugs*, edited by H. Bundgaard, (Elsevier, 1985);

c) *A Textbook of Drug Design and Development*, P. Krogs-gaard-Larsen and H. Bundgaard, eds. Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).
Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Third Edition (Wiley and Sons, 1999)).

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

Chemokine receptor antagonists of the present invention can be prepared from the protected beta-amino acid derivative 1.1 by coupling with a piperidine 1.2 (see synthesis disclosed in WO 04/043965) under standard amide bond forming conditions to yield 1.3 as shown in Scheme 1. Deprotection of the nitrogen can provide an amine 1.4 which can be reacted further with derivatizing reagents to provide (I).

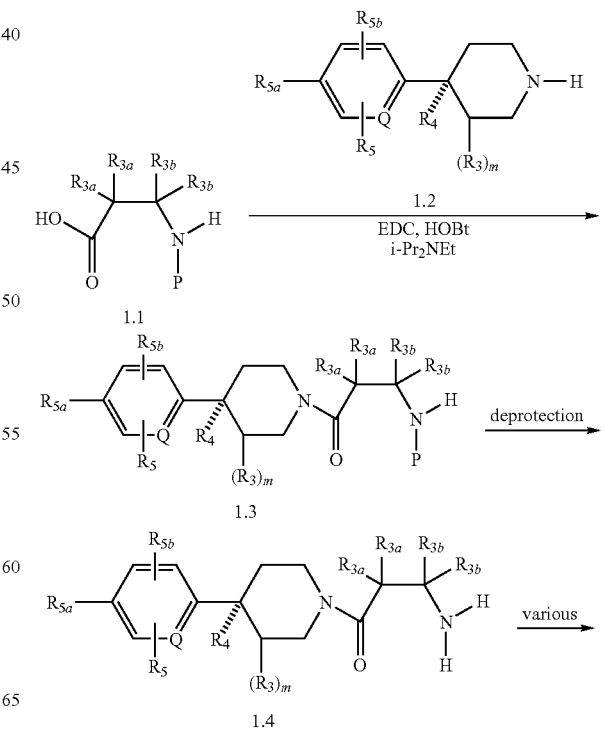

Scheme 1

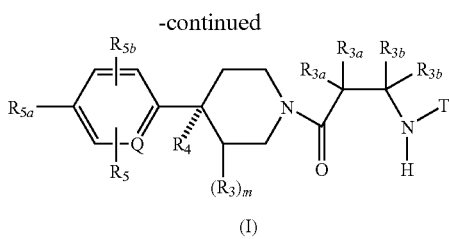

Alternatively, compounds of the present invention can be synthesized as shown in Scheme 2. Coupling of the functionalized beta-amino acid derivative 2.1 with piperidine 1.2 under standard amide bond forming conditions can provide compound I.

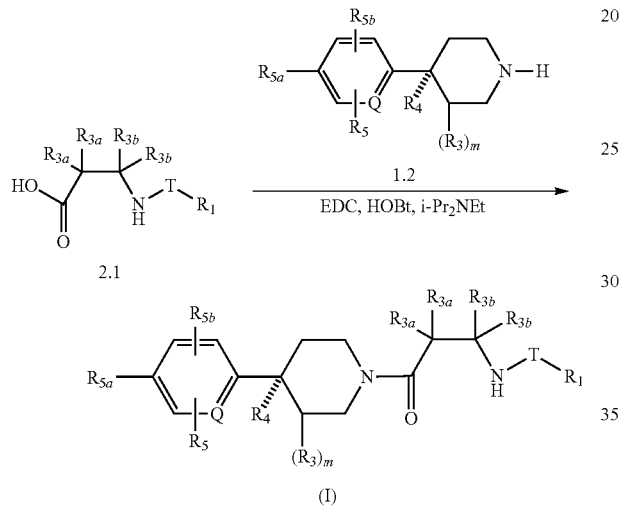

The linkers represented by —(C═Z)—W—NH— in the scope of this application are essentially beta-amino acids and their derivatives. They are available commercially or can be synthesized by the following methods. For example, Davies, et al., have found that one can perform lithium N-benzyl-N-α-methylbenzylamide additions to substituted acrylate esters to obtain diastereomeric mixtures of substituted beta-amino acid derivatives in which one of the diastereomers is usually favored as shown in Scheme 3a (Davies, S. G. et al., *J. Chem. Soc. Perkin Trans. I*, 1994, 1129-1139; Davies, S. G. et al., *J. Chem. Soc. Perkin Trans. I*, 1994, 1141-1147; Bunnage, M. E. et al., *J. Chem. Soc. Perkin Tran. I*, 1994, 2373-2384; Burke, A. J. et al., *Synlett* 1996, 621-622; and references therein). The intermediate enolate after the lithium amide addition can be quenched by a proton or by a variety of electrophiles, such as alkyl iodides, chiral campholsulfonyloxaziridines (Davis Reagents: Davis, F. A. et al., *J. Org. Chem.* 1992, 57, 7274-7285) to introduce hydroxyl, trisylazide to introduce $N_3$, and the like. to yield 3a.2 and 3a.5. These intermediates can in turn be converted to their beta-amino acid derivatives 3a.3 and 3a.6 by methods familiar to one skilled in the art which can in turn be used to synthesize the compounds in the scope of this application. In addition, one may envision deprotonating esters of 3a.3 and reprotonating them to obtain mixtures of diastereomers which can be chromatographically separated. Alternatively, Davies has found that one can alkylate 3a.2a with electrophiles such as alkyl halides to yield the beta-amino acid 3a.3a, where the diastereomer shown is the predominant one (Scheme 3b) (Davies, op. cit.). It is to be understood that one can perform the chirality transfer in Schemes 3a and 3b with the opposite enantiomeric starting material to yield the enantiomers of the compounds drawn.

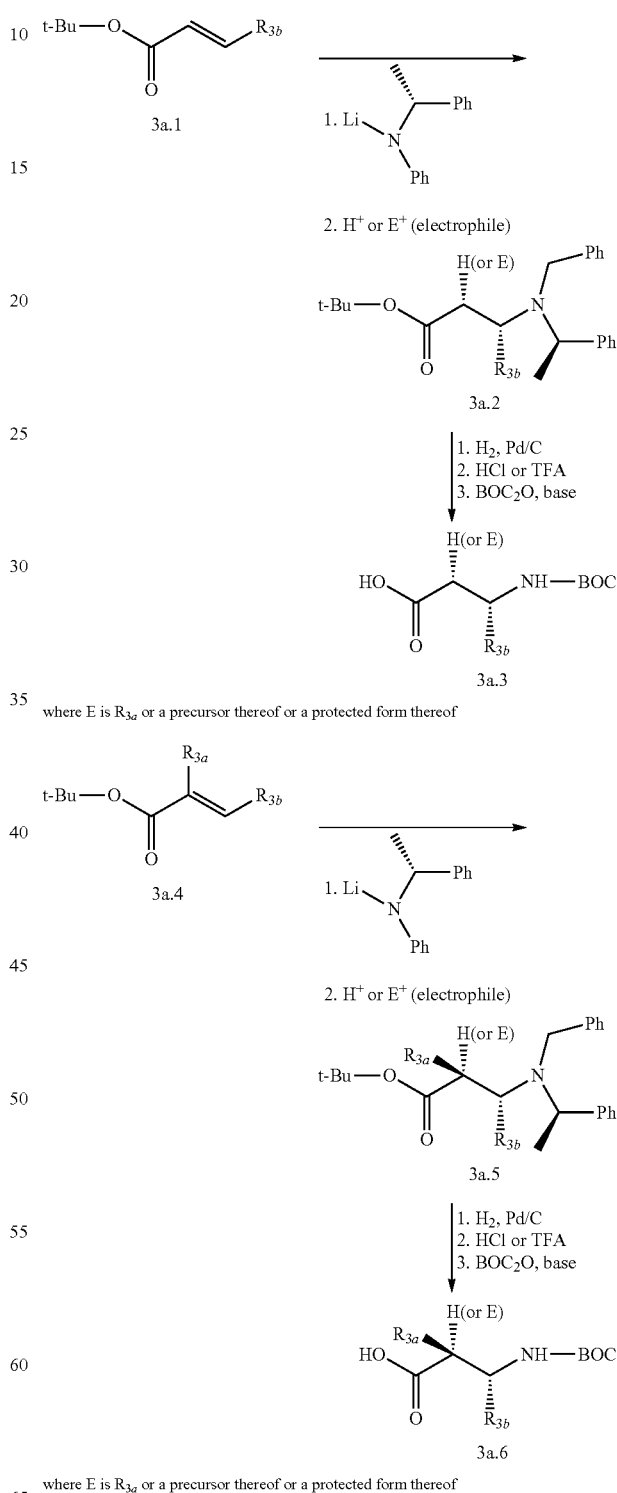

Scheme 3b

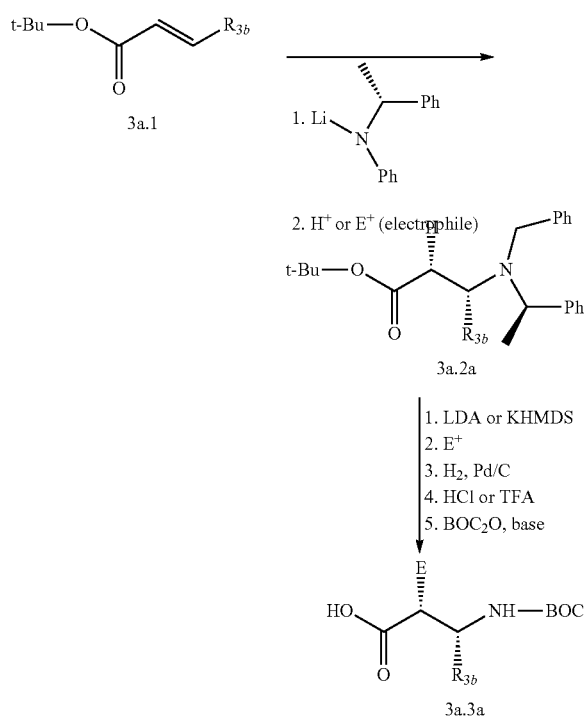

where E is $R_{3a}$ or a precursor thereof or a protected form thereof

Another chiral synthesis (not shown) of 3a.3 (E=H) involves the application of the Arndt-Eistert homologation to α-amino acids (Penke, B. et al., *Helv. Chim. Acta* 1970, 53, 1057; Podlech, J. et al., *Liebigs Ann.,* 1995, 1217; Juaristi, E., *Enantioselective Synthesis of β-Amino Acids* (Wiley-VCH, New York, 1997); Matthews, J. L. et al., ibid., pp. 105-126) (for a safer amino acid one carbon homologation procedure which does not use diazomethane, see Gray, D. et al., *J. Org. Chem.* 2004, 69, 4849-4851). The methyl ester of 3a.3 can in turn be doubly lithiated and quenched with electrophiles to synthesize the methyl ester of 3a.3a (not shown). These reactions depending on the solvent conditions can lead to a preference of one diastereomer over the other or to a mixture of diastereomers which can be chromatographically separated (Seebach, D. et al., *Helv. Chim. Acta* 1998, 81, 932-982 and references therein). Thus not only are the syn-diastereomers obtained, but also the anti in good enantiomeric purity.

To synthesize spiro-fused rings at the $R_{3b}$ position in W (two $R_{3b}$s taken together to form a ring), one may employ the syntheses shown in Scheme 3c. It is to be understood that the cyclopropyl ring in 3c.3 can be larger and can contain heteroatoms. (see GB 1,415,338, GB 1,419,256, and Mertin, A. et al., *Synlett,* 1991, 87-89.)

To synthesize spiro-fused rings at the $R_{3a}$ position in W (two $R_{3a}$s taken together to form a ring), one may employ the syntheses shown in Scheme 3d. It is to be understood that the cyclopropyl ring in 3d.2, 3d.3, and 3d.4 can be larger and can contain heteroatoms (Ohno, M. et al., *Synlett* 1991, 919-920).

Scheme 3c

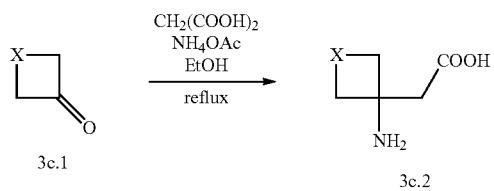

X = methylene(s) one of which can be replaced with a heteroatom

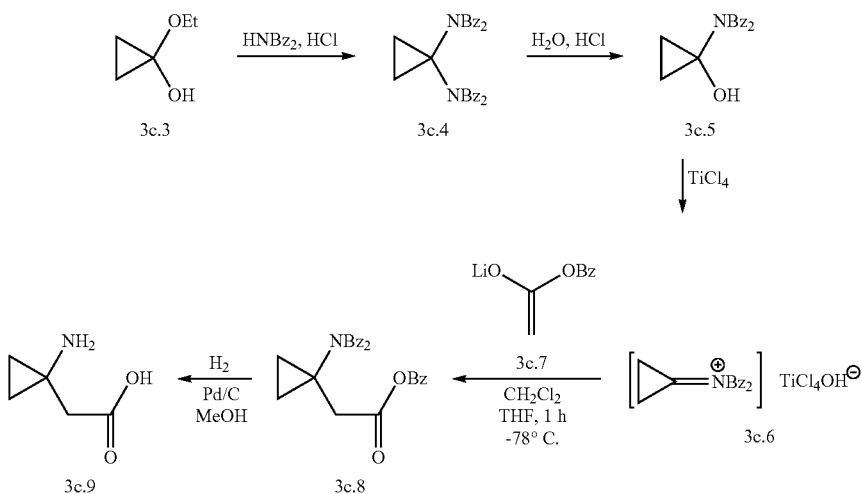

-continued
Scheme 3d

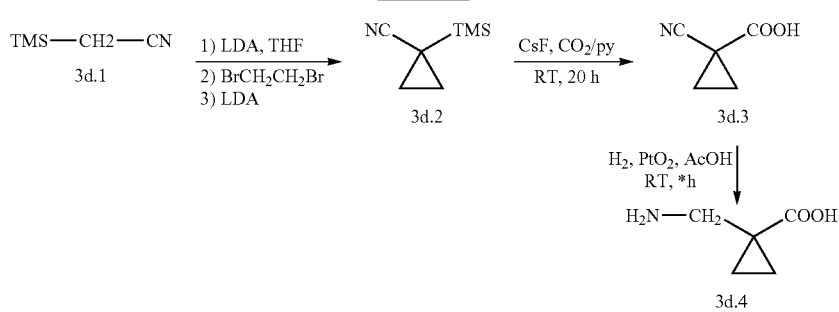

In a similar manner, bis-alkylation of methyl cyanoacetate with alkyldibromides yields after hydrolysis 3d.4 wherein the spiro-fused cyclopropyl ring is replaced with a larger ring which can optionally contain heteroatoms substituted within the carbon ring itself (not shown) (Gilmore, J. et al., *Bioorg. Med. Chem. Lett.* 2006, 16, 2699-2704.

Scheme 3e shows the synthesis of beta-amino acid linkers wherein there is only a single substitution at the $R_{3a}$ position. The racemic beta-amino acids 3e.4 can be separated into their enantiomers via crystallization or via chiral phase chromatography, methods familiar to one skilled in the art (Hellmann, H. et al., *Chem. Ber.* 1957, 90, 1357-1363).

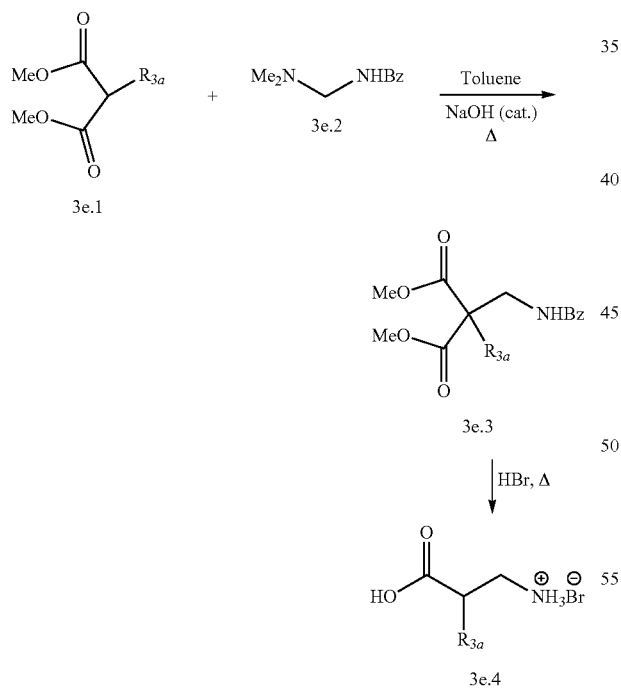

A chiral synthesis of compounds 3e.4 has been developed (Evans, D. A. et al., *J. Am. Chem. Soc.* 1990, 112, 8215; Seebach, D. et al., *Helv. Chim. Acta* 1998, 81, 932-982) which is shown in Scheme 3f. Note that the opposite enantiomer of 3f.3 can easily be obtained via the other enantiomeric oxazolidinone of 3f.1.

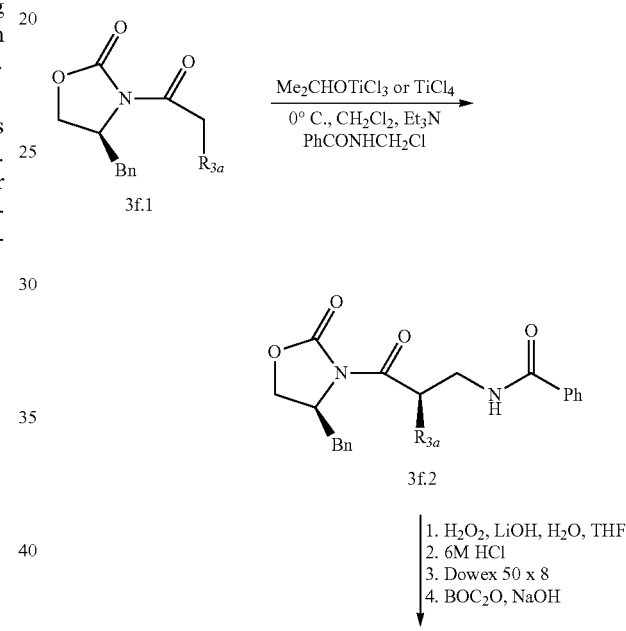

Another synthesis of $R_{3b}$ substituted beta-amino acid derivatives 3a.3 or 3a.3a where E=H starting from aspartic acid is shown in Scheme 3g. Aspartic acid derivative 3g.1 is reduced to alcohol 3g.2. Subsequent mesylation and displacement by iodide anion yields 3g.4. This iodide may be hydrogenated and subsequently saponified to yield compound 3g.6 wherein $R_{3b}$=Me. Iodide 3g.4 may likewise undergo displacement reactions by a wide variety of nucleophiles familiar to one skilled in the art to yield 3g.7. Subsequent saponification yields 3g.8 wherein $R_{3b}$=CH$_2$-Nu wherein Nu represents the nucleophile used in the displacement reaction and can be any substituent within the scope of this invention or a precursor/protected form thereof.

Scheme 3g

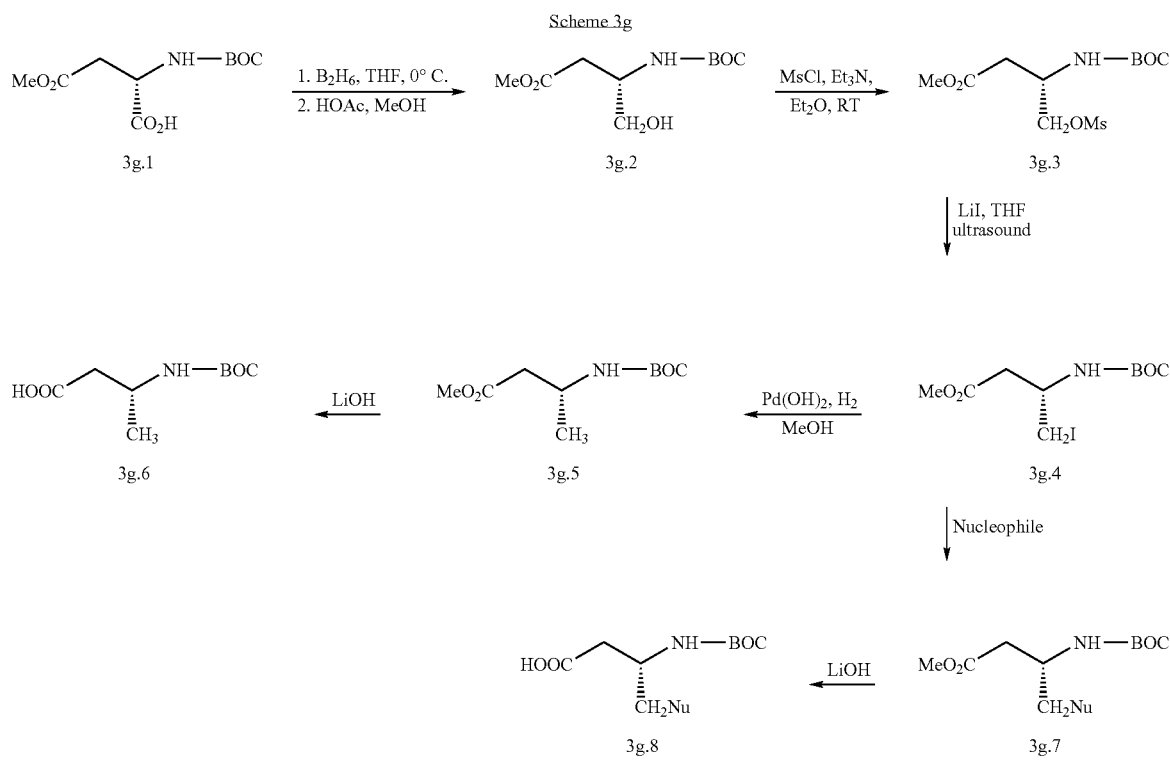

A resin supported synthesis can also be employed using the reactions outlined in Scheme 4. Coupling of an amine ester to a properly functionalized resin can give 4.1 which upon amine functionalization can form 4.2. Standard saponification can yield the pendant acid derivatized resin 4.3. Amide bond formation with amine 1.2 can furnish analog 4.4. Removal from the resin using acid can furnish the piperidine (I) from 4.4.

Scheme 4

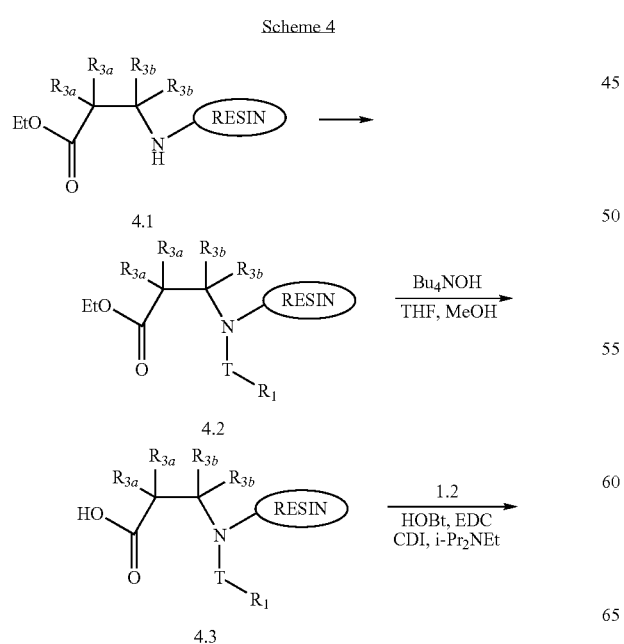

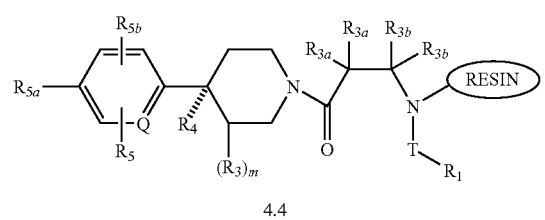

Compounds of the invention can also be prepared according to the methods outlined in Scheme 5. An appropriately functionalized amine 1.4 can be reacted with an isothiocyanate followed by alkylation in the presence of a base with iodomethane to furnish 5.1. Compound 5.1 can be further reacted with, for example a hydrazine or a hydroxylamine derivative, to furnish the substituted triazole or the oxadiazole of the present invention.

Scheme 5

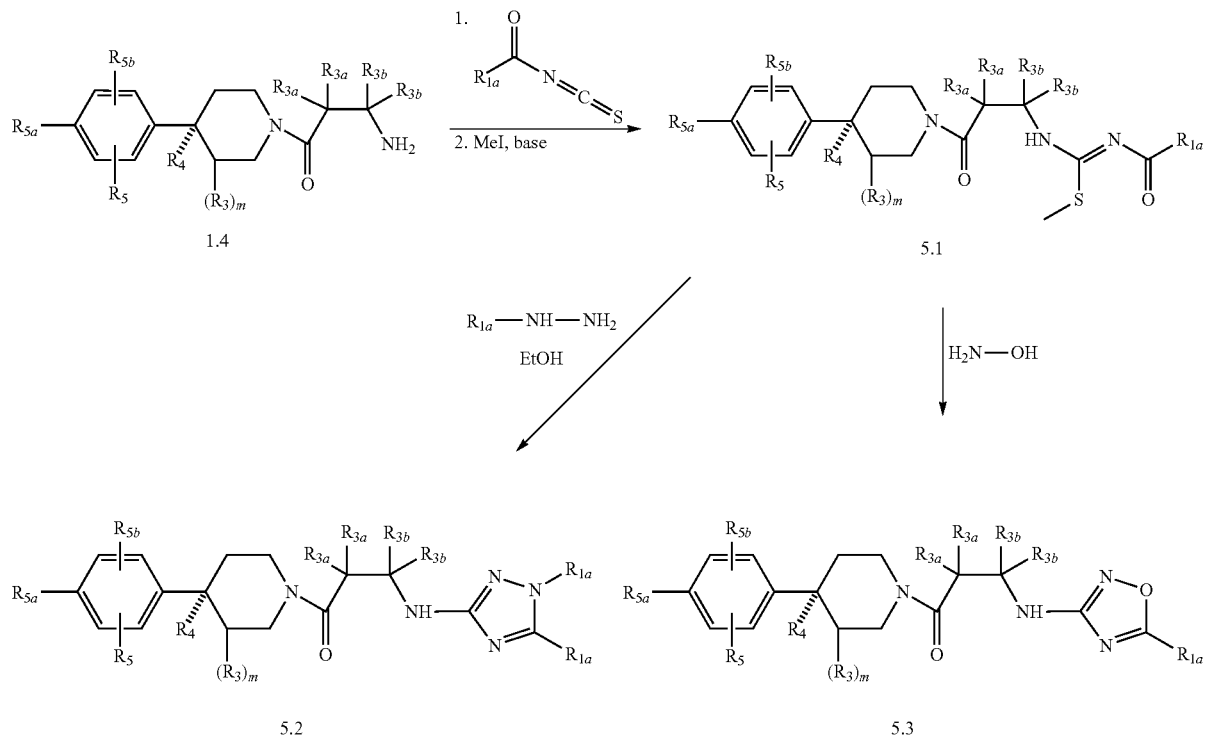

Furthermore, compounds of the present invention can be prepared by reaction of amine 1.4 with an appropriate boronic acid-containing aryl or heteroaryl group in the presence of a copper catalyst to yield coupled product 6.2 (Scheme 6) (for a review of the Chan-Lam Reaction, see Chan, D. M. T. et al., "Recent Advances in Copper-Promoted C-Heteroatom Bond Cross-Coupling Reactions with Boronic Acids and Derivatives" in *Boronic Acids*, Hall, D. G., ed., Wiley-VCH Verlag GmbH & Co., Weinheim, 2005. ISBN 3-527-30991-8). Other N-arylation or N-heteroarylation methods include reaction of an amine and an aryl iodide (or bromide) or a heteroaryl iodide (or bromide) in the presence of a palladium catalyst (see Charles, M. D. et al., *Org. Lett*. 2005, 7(18), 3965-3968; Jiang, L. et al., "Palladium-catalyzed aromatic carbon-nitrogen bond formation" in *Metal-Catalyzed Cross-Coupling Reactions* (2nd Edition) 2004, 2, 699-760; Anderson, K. W. et al., "Palladium-Catalyzed Amination of Aryl Nonaflates", *J. Org. Chem*. 2003, 68(25), 9563-9573; Kwong, F. Y. et al., *Org. Lett*. 2002, 5(6), 793-796; Wolfe, J. et al., *J. Org. Chem*. 1997, 62, 6066-6078; Wolfe, J. et al., *J. Am. Chem. Soc.,* 1996, 118, 7215-7216, and references therein). Activated halogens on aryl rings and on heterocycles can be displaced by amine 1.4 to yield the N-arylated/heteroarylated products 6.2 and 6.3, respectively. For example, fluorophenyls with ortho- or para-nitro groups or other electron-withdrawing groups undergo the nucleophilic aromatic substitution reaction in polar solvents such as DMF or DMSO. Heterocyclic halogens substituted on carbon atoms located alpha to neighboring heteroatoms can often be displaced by amines in a polar solvent with heating or in a microwave reactor. For a review of these aryl/heteroaryl nucleophilic displacement reactions, see Dimethyl Sulfoxide (DMSO) Technical Bulletin, Crown Zellerbach Corporation, Chemical Products Division.

Scheme 6

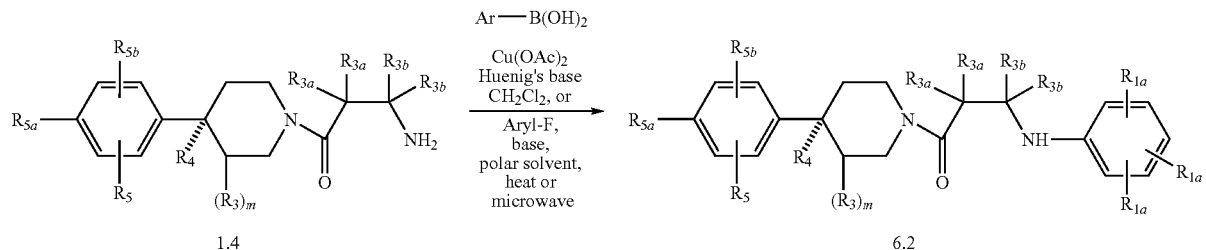

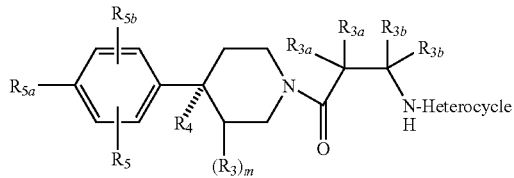

6.3

Alternatively, compounds of the present invention can be synthesized as shown in Scheme 7. Reacting a properly functionalized analog of compounds of the present invention under a variety of conditions known to those skilled in the art can provide additional compounds of the present invention. It is to be assumed that the examples shown in Scheme 7 are merely representative of a variety of transformations and interconversions of functionality that are possible with the knowledge of one skilled in the art of organic synthesis. For example, it is to be understood that phenylboronic acids or phenyltrialkyltin can be replaced with heteroaryl or protected heteroaryl and possibly other moieties and that the phenyl is only used as an example.

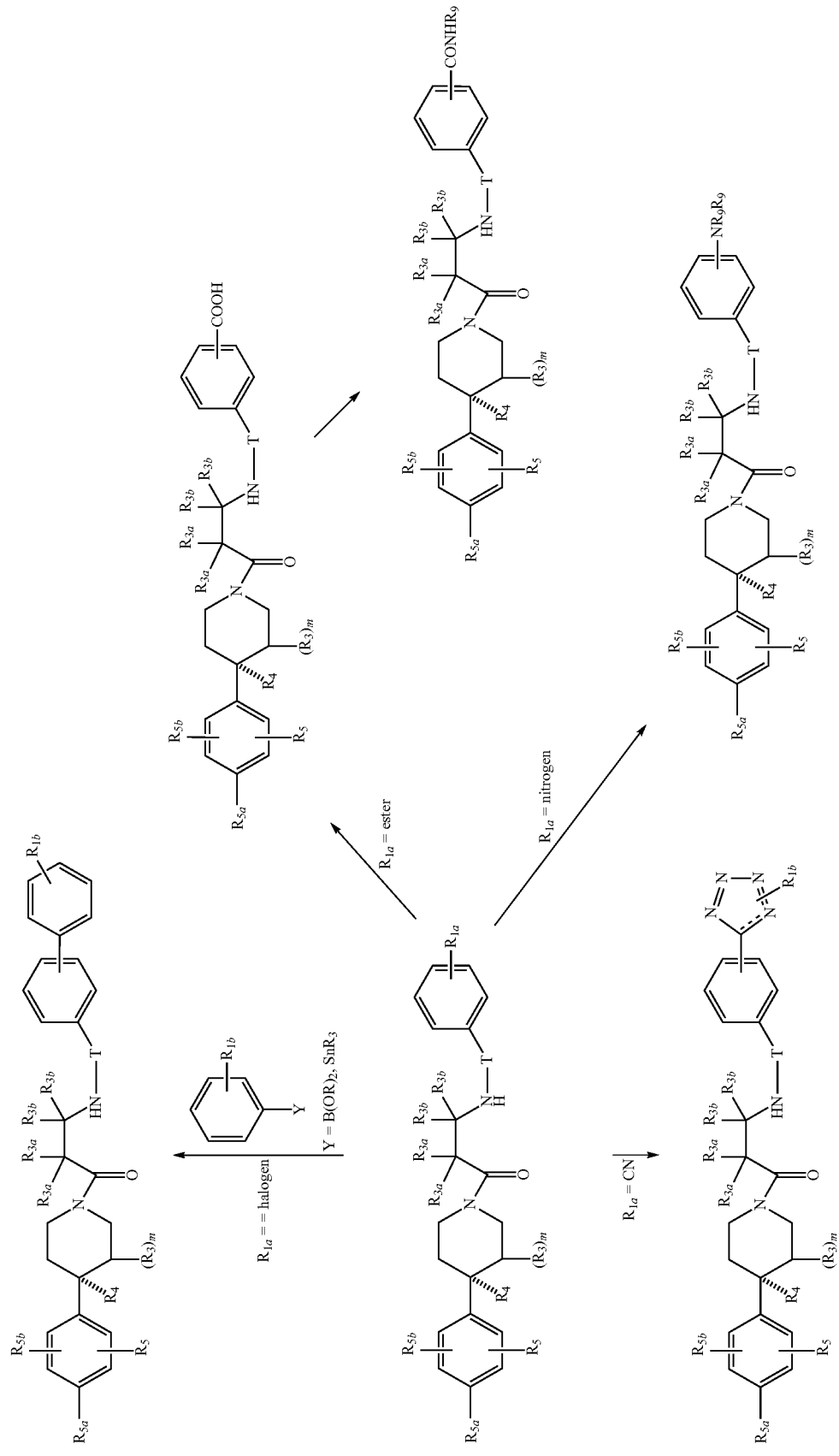

Furthermore, compound 1.4 could be reacted with an anhydride or an acid chloride to provide the amide 8.1. It can also be reacted with a sulfonyl chloride to yield sulfonamide 8.2 (Scheme 8). Likewise, 1.4 can be reacted with a haloacetyl halide, such as chloroacetyl chloride, followed by a nucleophile, such as a heterocyclic anion or a basic heterocycle, to give the substituted amide 8.3. Other non-heterocyclic nucleophiles which can also be reacted and are familiar to one skilled in the art include but are not limited to azide, cyano, $R_1$—$S^-$, $R_1$-amino, etc. Some of these can be further elaborated into other functionality within the scope of this application by methods familiar to one skilled in the art.

solvent to yield carbamate 9.1. If this carbamate is a phenyl carbamate or a 4-nitrophenylcarbamate or a pentafluorophenylcarbamate or any other phenylcarbamate with an electron withdrawing group(s), then the phenoxy of the carbamate may be displaced by an amine at RT to reflux temperature of the inert solvent to yield urea 9.2. Likewise, amine 1.4 may be reacted in an inert solvent with an isocyanate to yield 9.2 where $R_8$=H, or may be reacted in an inert solvent in the presence of a base such as triethylamine or Hunig's base with a carbamoyl chloride to yield 9.2 where $R_8 \neq H$. Furthermore, cyanoguanidines (T=—(C=N—CN)$NR_8$—) can be synthesized by the method of K. S. Atwal et al. and references contained therein (*J. Med. Chem.* 1998, 41, 217-275) (not shown). Squaric acid-type isosteres can be synthesized by the method of Poindexter, G. S. et al. (*Bioorg. Med. Chem.* 2004, 12, 507-521) (not shown).

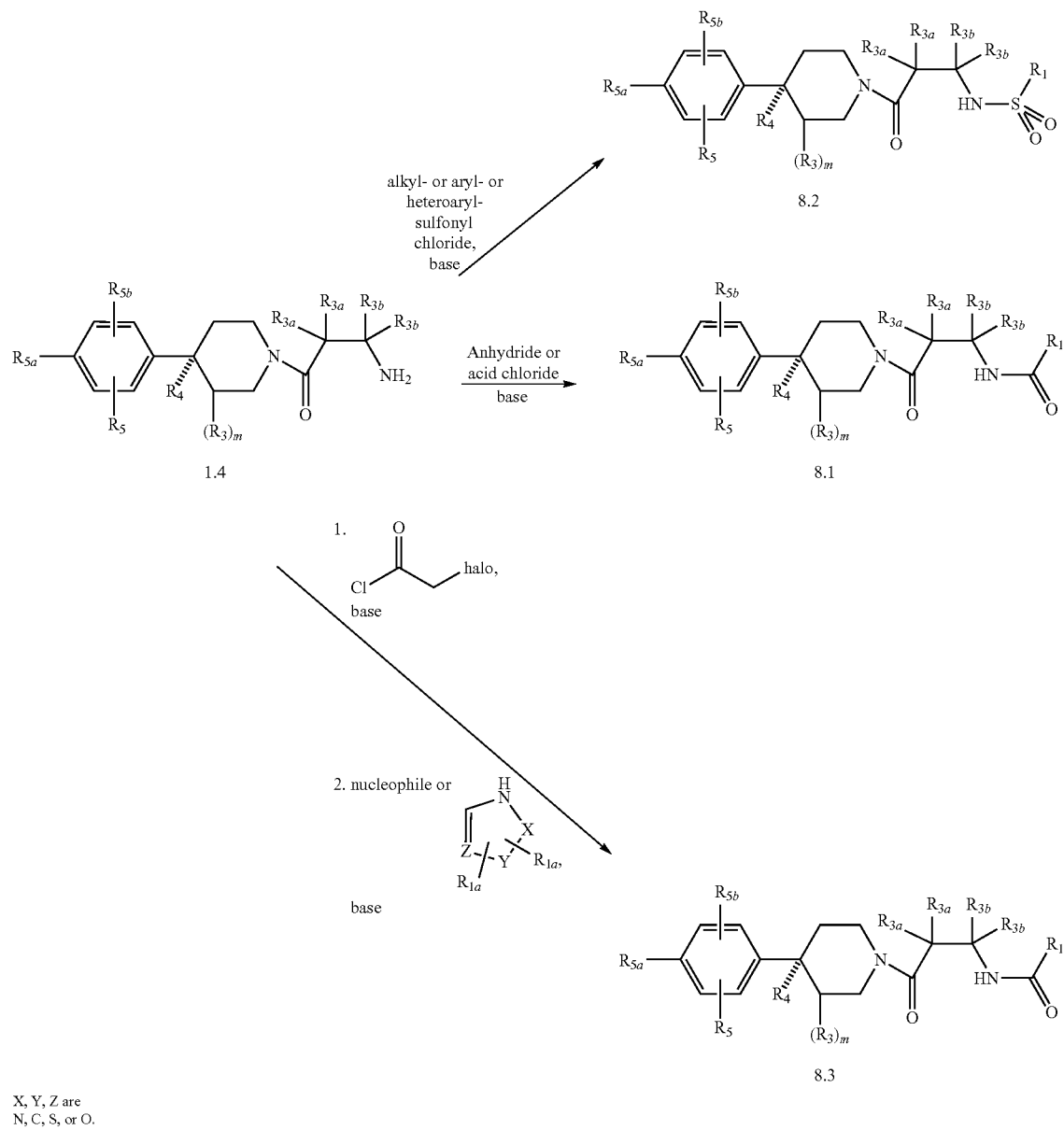

Scheme 8

X, Y, Z are
N, C, S, or O.

Scheme 9 outlines methods to synthesize T=—CO—O— (carbamates) and —CO—$NR^8$— (ureas). For example, amine 1.4 can be reacted with a chloroformate in the presence of a base such as triethylamine or Hunig's base in an aprotic Scheme 9

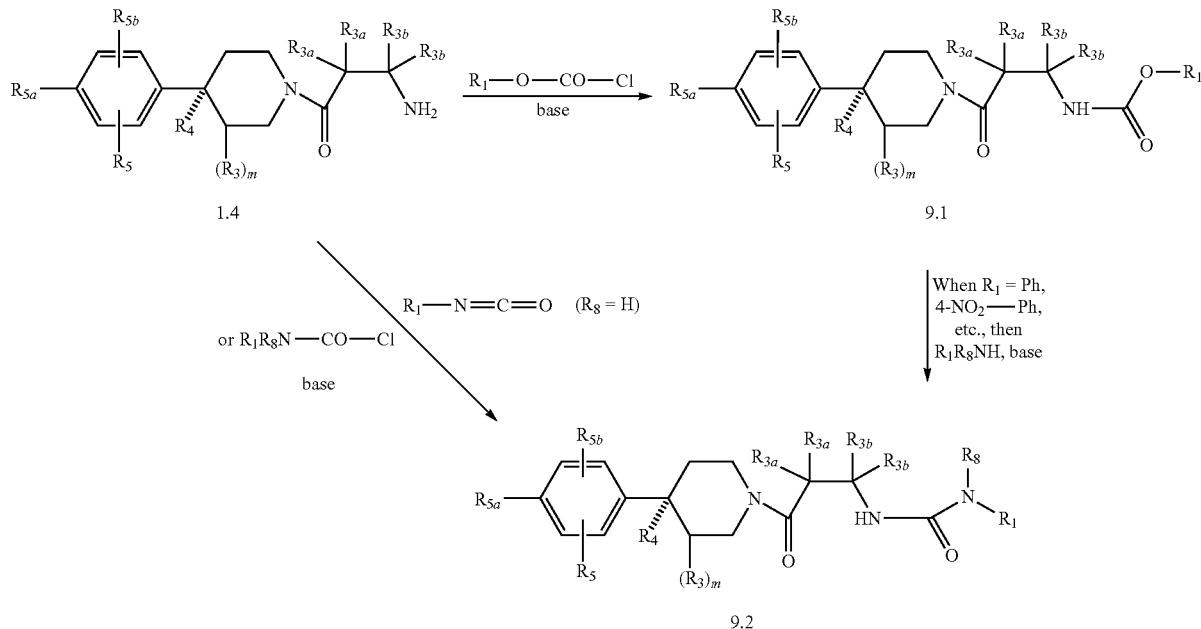

EXAMPLES

Abbreviations used in the Examples are defined as follows: "3×" for thrice, "4×" for four times, "5×" for five times, "Boc" for tert-butyloxycarbonyl, "° C." for degrees Celsius, "DMF" for N,N-dimethylformamide, "EDC" for N-(3-dimethylaminopropyl)-N-ethylcarbodiimide hydrochloride, "g" for gram or grams, "HOBt" for 1-hydroxybenzotriazole, "LC" for liquid chromatography, "HPLC" for high performance liquid chromatography, "mg" for milligram or milligrams, "mL" for milliliter or milliliters, "μL" for microliter or microliters, "h" for hour or hours, "mmol" for millimolar, "M" for molar, "N" for normal, "NaOH" for sodium hydroxide, "HCl" for hydrochloric acid, "MeOH" for methanol, "min" for minute or minutes, "MS" for mass spectroscopy, "rt." for room temperature, "TFA" for trifluoroacetic acid, "THF" for tetrahydrofuran, and "v/v" for volume to volume ratio. "D", "L", "R" and "S" are stereochemical designations familiar to those skilled in the art. Chemical names were derived using ChemDraw Ultra, version 8.0.8. When this program failed to provide a name for the exact structure in question, an appropriate name was assigned using the same methodology utilized by the program.

Example 1

(S)-3-(2-(Benzyloxymethyl)-2H-tetrazol-5-yl)-N-(4-(4-(4-chlorophenyl)-4-hydroxy-3,3-dimethylpiperidin-1-yl)-2-methyl-4-oxobutan-2-yl)benzamide

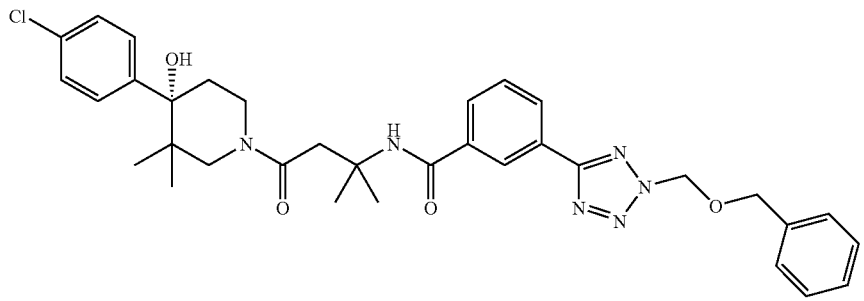 [SMILES: CC(C)(CC(=O)N1CC[C@](O)(c2ccc(Cl)cc2)C(C)(C)C1)NC(=O)c1cccc(-c2nnn(COCc3ccccc3)n2)c1]

Step 1:
3-(tert-Butoxycarbonylamino)-3-methylbutanoic acid

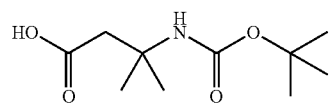

A solution of 3-amino-3-methylbutanoic acid (0.59 g, 5.04 mmol) and BOC-anhydride (1.228 mL, 5.29 mmol) in dioxane (10 mL) was treated with 1 M potassium hydroxide (5.04 mL, 5.04 mmol), and the mixture was stirred for about 16 h at rt. The dioxane was removed from the solution under reduced pressure, and the remaining cloudy aqueous solution was diluted with water (20 mL) and treated with lithium hydroxide to adjust the pH to 13. The mixture was washed 3× with diethyl ether, then the pH was adjusted to 3 with 2 N HCl. The cloudy solution was extracted 4× with ethyl acetate, then the combined ethyl acetate phases were washed with a small amount of brine, dried over sodium sulfate, and concentrated in vacuo to yield the title compound (860 mg, 3.96 mmol, 79% yield) as a crystalline solid.

Step 2: (S)-tert-Butyl 4-(4-(4-chlorophenyl)-4-hydroxy-3,3-dimethylpiperidin-1-yl)-2-methyl-4-oxobutan-2-ylcarbamate

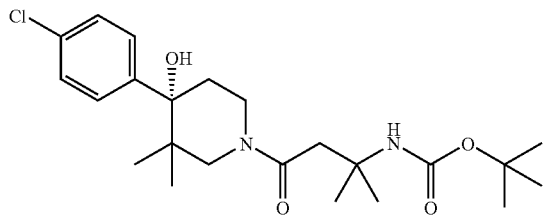 [SMILES: CC(C)(CC(=O)N1CC[C@](O)(c2ccc(Cl)cc2)C(C)(C)C1)NC(=O)OC(C)(C)C]

A mixture of (S)-4-(4-chlorophenyl)-3,3-dimethylpiperidin-4-ol (prepared in a similar manner as described in International Patent Application No. WO 04/043965, 0.949 g, 3.96 mmol), 3-(tert-butoxycarbonylamino)-3-methylbutanoic acid (0.86 g, 3.96 mmol), HOBt (1.334 g, 8.71 mmol), and Hunig's base (2.074 mL, 11.88 mmol) in methylene chloride (20 mL) was treated with EDC (1.669 g, 8.71 mmol), and the reaction was allowed to stir for about 16 h at room temperature. The mixture was concentrated in vacuo, and the residue was taken up in ethyl acetate. The organic phase was washed 3× with 1M NaOH, 3× with 1M HCl, once with water, and once with brine, dried over sodium sulfate, and concentrated in vacuo to yield an amber solid which was used as-is in the next step.

Step 3: (S)-3-Amino-1-(4-(4-chlorophenyl)-4-hydroxy-3,3-dimethylpiperidin-1-yl)-3-methylbutan-1-one, HCl

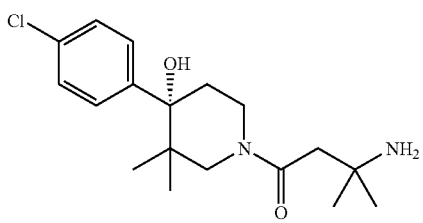 [SMILES: CC(C)(N)CC(=O)N1CC[C@](O)(c2ccc(Cl)cc2)C(C)(C)C1]

A solution of (S)-tert-butyl 4-(4-(4-chlorophenyl)-4-hydroxy-3,3-dimethylpiperidin-1-yl)-2-methyl-4-oxobutan-2-ylcarbamate (1.6 g, 3.64 mmol) in 4 M HCl in dioxane (10 mL, 40.0 mmol) was stirred at room temperature for 3 hours. The mixture was concentrated in vacuo, and evaporated 3× from methylene chloride to remove residual HCl and dioxane, to yield the title compound as a colorless foam. MS (ESI⁺)=339.1 (M+H)⁺.

Step 4: 2-(Benzyloxymethyl)-2H-tetrazole

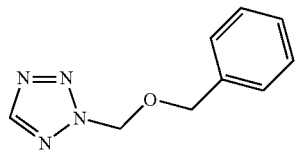 [SMILES: c1ccc(COCn2ncnn2)cc1]

A suspension of 1-H-tetrazole (2.0 g, 28.5 mmol) and potassium carbonate (5.9 g, 42.7 mmol) in DMF (30 mL) was treated with benzyl chloromethyl ether (5.36 g, 34.2 mmol), and the mixture was stirred for 4 hours. Analysis by LC/MS indicated that the reaction was not complete, so the reaction was treated with benzyl chloromethyl ether (0.5 g, 3.19 mmol) and stirred for about 16 h. After this time, the mixture was filtered, and the filtrate was concentrated in vacuo to yield a residue. The residue was diluted with diethyl ether (200 mL), washed 5× with water (50 mL), once with brine, dried over sodium sulfate, and concentrated in vacuo to yield a residue. The residue was purified over a 6×20 mm silica gel column, eluting with 20% then 30% ethyl acetate/hexanes to yield the title compound (2.39 g, 44% yield), and 1-(benzyloxymethyl)-2H-tetrazole (2.56 g, 47% yield).

Step 5: 2-(Benzyloxymethyl)-5-(tributylstannyl)-2H-tetrazole

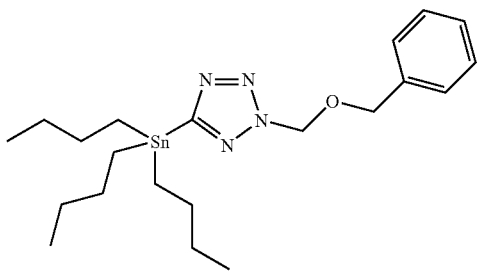 [SMILES: CCC[CH2][Sn]([CH2]CCC)([CH2]CCC)[c]1nnn(COCc2ccccc2)n1]

In a flame-dried three-neck flask, a solution of 2-(benzyloxymethyl)-2H-tetrazole (2.01 g, 10.57 mmol) and tetramethylethylenediamine (3.16 mL, 21.4 mmol) in diethyl ether (30 mL) was cooled to −78° C. and then treated with the dropwise addition of n-butyllithium (1.6 M in hexanes, 7.3 mL, 11.62 mmol), causing the color of the solution to turn dark red. Upon completion of addition, the mixture was stirred for 10 minutes, then transferred via cannula to a solution of tributyltin chloride (2.9 mL, 10.57 mmol) in diethyl ether (20 mL) which had been pre-cooled to −78° C. The resulting reaction was stirred for 45 min, then quenched with a saturated ammonium chloride solution. The reaction mixture was allowed to come to room temperature, and the layers were separated. The aqueous phase was extracted 3× with ethyl acetate, and the combined organic phases were washed with brine, dried over sodium sulfate, and concentrated in vacuo to yield a residue. The residue was purified over silica gel, eluting with 1% then 5% then 10% ethyl acetate/hexanes to yield the title compound (3.0 g, 60% yield) as a colorless oil.

Step 6: 3-(2-(Benzyloxymethyl)-2H-tetrazol-5-yl)benzoate

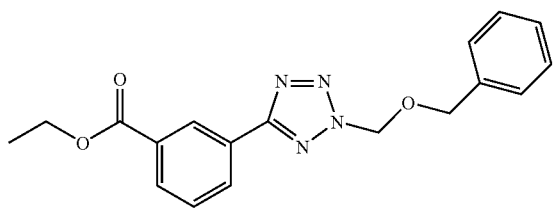 [SMILES: CCOC(=O)c1cccc(-c2nnn(COCc3ccccc3)n2)c1]

A solution of ethyl-3-bromobenzoate (0.47 g, 2.05 mmol) and 2-(benzyloxymethyl)-5-(tributylstannyl)-2H-tetrazole in toluene (20 mL) was degassed under vacuum and argon. To this solution was added copper (I) iodide (20 mg, 0.20 mmol) and tetrakis(triphenylphosphine)palladium(0) (115 mg, 0.10 mmol). The reaction mixture was again degassed under vacuum and argon. The flask and condenser were covered in foil to exclude light, and the reaction mixture was heated at reflux temperature for 3 hours. After cooling to room temperature, the reaction mixture was filtered and the filtrate was concentrated in vacuo. The resulting residue was purified over a 3.5×12 cm silica gel column, eluting with 5% then 10% then 15% ethyl acetate/hexanes to yield the title compound as a colorless oil, which contained 5% of a tributyltin impurity. MS (ESI$^+$)=339.22, (M+H)$^+$. The oil was used as-is in the next step.

Step 7: 3-(2-(Benzyloxymethyl)-2H-tetrazol-5-yl)benzoic acid

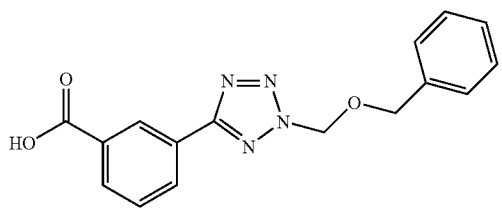 [SMILES: O=C(O)c1cccc(-c2nnn(COCc3ccccc3)n2)c1]

A solution of ethyl 3-(2-(benzyloxymethyl)-2H-tetrazol-5-yl)benzoate (653 mg, 1.93 mmol) in THF (10 mL) was treated with a 0.5 M aqueous lithium hydroxide solution (5.8 mL, 2.9 mmol), and the reaction mixture was stirred for about 16 h. Analysis by LC/MS indicated that the reaction had not gone to completion, so the mixture was treated with a 0.5 M aqueous lithium hydroxide solution (1 mL, 0.5 mmol), and the reaction mixture was stirred for an additional 6 hours. The THF was removed under reduced pressure, and the aqueous solution was treated with 1 N HCl (3.5 mL, 3.5 mmol). The resulting mixture was extracted 3× with ethyl acetate, and the combined organic phases were dried over sodium sulfate and concentrated in vacuo to yield the title compound as a colorless powder which was used as-is in the next step.

Step 8: Example 1

A mixture of (S)-3-amino-1-(4-(4-chlorophenyl)-4-hydroxy-3,3-dimethylpiperidin-1-yl)-3-methylbutan-1-one, HCl (90 mg, 0.266 mmol), 3-(2-(benzyloxymethyl)-2H-tetrazol-5-yl)benzoic acid (91 mg, 0.292 mmol), HOBt (89 mg, 0.584 mmol), and Hunig's Base (0.232 mL, 1.328 mmol) in methylene chloride (1 mL) was treated with EDC (112 mg, 0.584 mmol), and the mixture was stirred for about 16 h at room temperature. The mixture was concentrated in vacuo, and the resulting residue was taken up in ethyl acetate. The organic phase was washed 3× with saturated sodium carbonate, 3× with 1N HCl, once with water, and once with brine, dried over sodium sulfate, and concentrated in vacuo. The residue was purified over a 12 g silica gel column, eluting at 30 mL/min with an ethyl acetate/hexanes gradient to yield Example 1 (130 mg, 0.206 mmol, 78% yield) as a colorless glass. $^1$H NMR (CDCl$_3$, 400 MHz) δ ppm 8.50-8.75 (1 H, m), 8.31 (1 H, t, J=9.15 Hz), 7.95 (1 H, dd, J=19.95, 7.51 Hz), 7.55-7.75 (1 H, m), 7.44 (0 H, d, J=1.46 Hz), 7.13-7.41 (8 H, m), 6.06 (2 H, d, J=1.46 Hz), 4.64-4.81 (0.3 H, m, rotamer), 4.70-4.89 (2 H+H$_2$O, m), 3.93-4.27 (1 H, m), 3.52-3.71 (1.3 H, m, rotamer), 3.27-3.34 (1 H+CH$_3$OH, m, 2.96-3.18 (1.3 H, m, rotamer), 2.50-2.91 (2 H, m), 1.37-1.77 (7 H, m), 0.56-0.99 (6 H, m). LCMS Method: Inj. Vol.=10 uL, Start % B=0, Final % B=100, Gradient Time=4 min, Flow Rate=4 ml/min, Wavelength=220, Solvent A=10% MeOH–90% H$_2$O–0.1% TFA, Solvent B=90% MeOH–10% H$_2$O–0.1% TFA, Column 1=Waters Sunfire C18 4.6×50 mm (4 min. grad), Retention Time=4.10 min.

Example 2

(S)—N-(4-(4-(4-Chlorophenyl)-4-hydroxy-3,3-dimethylpiperidin-1-yl)-2-methyl-4-oxobutan-2-yl)-3-(2H-tetrazol-5-yl)benzamide

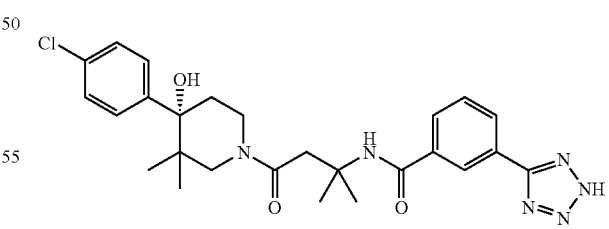

A solution of (S)-3-(2-(benzyloxymethyl)-2H-tetrazol-5-yl)-N-(4-(4-(4-chlorophenyl)-4-hydroxy-3,3-dimethylpiperidin-1-yl)-2-methyl-4-oxobutan-2-yl)benzamide (120 mg, 0.190 mmol) in MeOH (2 mL) was treated with 6 M HCl (0.634 mL, 3.80 mmol), and the mixture was heated for about 16 h at 50° C. The reaction mixture was injected directly onto a preparative HPLC for purification using the following conditions:

A=H₂O+0.05% TFA, B=acetonitrile+0.05% TFA

Column: Phenomenex Luna 5μ C18(2) 250×21.2 mm

Flow: 15 mL/min

Gradient: 0% B over 3 min, 0-100% B over 15 min, 100% B for 5 min

Fractions containing the desired product were combined and freeze-dried to yield Example 2 (40 mg, 0.078 mmol, 41.2% yield) as a colorless powder. MS (ESI⁺)=511.3 (M+H)⁺. ¹H NMR (CD₃OD, 500 MHz) (NMR shows several rotamers) δ ppm 8.47 (s, 0.5 H), 8.42 (s, 0.5 H), 8.22-8.17 (m, 1 H), 8.00 (d, J=7.70 Hz, 0.5 H), 7.97 (d, J=7.70 Hz, 0.5 H), 7.68 (t, J=7.97 Hz, 1 H), 7.46 (d, J=8.8 Hz, 1 H), 7.36 (d, J=8.8 Hz, 1 H), 7.30 (d, J=8.8 Hz, 1 H), 7.23 (d, J=8.8 Hz, 1 H), 4.59 (dd, J=11.55, 2.75 Hz, 0.5 H), 4.17-4.07 (m, 1 H), 3.63-3.55 (m, 1.5 H), 3.22 (d, J=14.85 Hz, 1 H), 3.12 (td, J=12.78, 2.47 Hz, 0.5 H), 3.07 (d, J=12.65 Hz, 0.5 H), 2.91 (d, J=14.85 Hz, 0.5 H), 2.72 (d, J=14.85 Hz, 0.5 H), 2.68-2.57 (m, 1 H), 1.64 (s, 1.8 H), 1.63 (s, 1.8 H), 1.60 (s, 1.2 H), 1.57 (s, 1.2 H), 1.50 (dd, J=14.02, 1.92 Hz, 1 H), 0.83 (s, 1.4 H), 0.82 (s, 1.4 H), 0.77 (s, 1.6 H), 0.68 (s, 1.6 H); HPLC Method: Inj. Vol.=5 uL; Start % B=10, 12 Min. 100%, 15 Min. 100%, Flow Rate=1 ml/min, Wavelength 1=220, Wavelength 2=254, Solvent A=0.05% TFA in H₂O:MeCN (95:5), Solvent B=0.05% TFA in H₂O:MeCN (5:95), Col-1: Sunfire C18 3.5 um, 4.6×150 mm; Retention Time=12.29 min., Col-2: Xbridge Phenyl 3.5 um, 4.6×150 mm; Retention Time=11.52 min.

Example 3

3-(2-(Benzyloxymethyl)-2H-tetrazol-5-yl)-N—((R)-4-((S)-4-(4-chlorophenyl)-4-hydroxy-3,3-dimethylpiperidin-1-yl)-4-oxobutan-2-yl)benzamide ol and Boc-D-beta-homoalanine using the conditions described in Example 1, Step 2. MS (ESI⁺)=425.1 (M+H)⁺.

Step 2: (R)-3-Amino-1-((S)-4-(4-chlorophenyl)-4-hydroxy-3,3-dimethylpiperidin-1-yl)butan-1-one, HCl

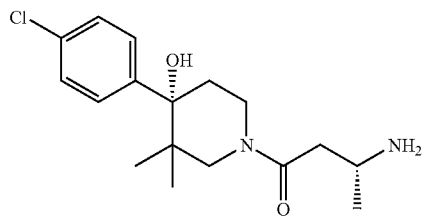

(R)-3-Amino-1-((S)-4-(4-chlorophenyl)-4-hydroxy-3,3-dimethylpiperidin-1-yl)butan-1-one, HCl was prepared from tert-butyl(R)-4-((S)-4-(4-chlorophenyl)-4-hydroxy-3,3-dimethylppiperidin-1-yl)-4-oxobutan-2-ylcarbamate using the conditions described in Example 1, Step 3. MS (ESI⁺)=325.1 (M+H)⁺.

Step 3: Example 3

Example 3 was prepared from (R)-3-amino-1-((S)-4-(4-chlorophenyl)-4-hydroxy-3,3-dimethylpiperidin-1-yl)butan1-one, HCl and 3-(2-(benzyloxymethyl)-2H-tetrazol-5-yl)benzoic acid using the conditions described in Example 1,

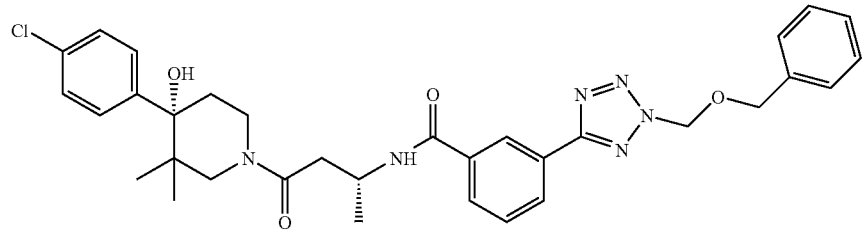 [SMILES: C[C@H](CC(=O)N1CC[C@](O)(c2ccc(Cl)cc2)C(C)(C)C1)NC(=O)c1cccc(-c2nnn(COCc3ccccc3)n2)c1]

Step 1: tert-Butyl(R)-4-((S)-4-(4-chlorophenyl)-4-hydroxy-3,3-dimethylpiperidin-1-yl)-4-oxobutan-2-ylcarbamate

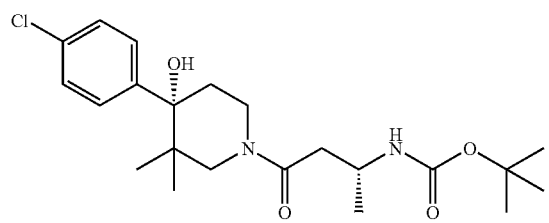 [SMILES: C[C@H](CC(=O)N1CC[C@](O)(c2ccc(Cl)cc2)C(C)(C)C1)NC(=O)OC(C)(C)C]

tert-Butyl(R)-4-((S)-4-(4-chlorophenyl)-4-hydroxy-3,3-dimethylpiperidin-1-yl)-4-oxobutan-2-ylcarbamate was prepared from (S)-4-(4-chlorophenyl)-3,3-dimethylpiperidin-4-

Step 8. MS (ESI⁺)=617.2 (M+H)⁺. ¹H NMR (CD₃OD, 500 MHz) (NMR shows several rotamers) δ ppm 8.68 (s, 0.6 H), 8.59 (s, 0.4 H), 8.37 (d, J=7.7 Hz, 0.6 H), 8.31 (d, J=8.1 Hz, 0.4 H), 8.03 (d, J=8.1 Hz, 0.6 H), 7.96 (d, J=7.7 Hz, 0.4 H), 7.74-7.59 (m, 1 H), 7.47 (d, J=8.8 Hz, 0.8 H), 7.39-7.23 (m, 7 H), 7.17 (d, J=8.4 Hz, 1.2 H), 6.08 (s, 1 H), 6.07 (s, 1 H), 4.72 (s, 1 H), 4.68 (s, 1 H), 4.62-4.47 (m, 1.4 H), 4.19-4.00 (m, 2 H), 3.70-3.55 (m, 1.4 H), 3.19-2.94 (m, 2 H), 2.68-2.48 (m, 2 H), 1.56-1.48 (m, 1 H), 1.43 (d, J=7.0 Hz, 1.8 H), 1.36 (d, J=7.0 Hz, 1.2 H), 0.85 (s., 1.2 H), 0.84 (s, 1.2 H), 0.75 (s, 1.8 H), 0.67 (s, 1.8 H); HPLC Method: Inj. Vol.=5 uL; Start % B=10, 12 Min. 100%, 15 Min. 100%, Flow Rate=1 ml/min, Wavelength 1=220, Wavelength 2=254, Solvent A=0.05% TFA in H₂O:MeCN (95:5), Solvent B=0.05% TFA in H₂O:MeCN (5:95), Col-1: Sunfire C18 3.5 um, 4.6×150 mm; Retention Time=13.96 min., Col-2: Xbridge Phenyl 3.5 um, 4.6×150 mm; Retention Time=12.92 min.

Example 4

N—((R)-4-((S)-4-(4-Chlorophenyl)-4-hydroxy-3,3-dimethylpiperidin-1-yl)-4-oxobutan-2-yl)-3-(2H-tetrazol-5-yl)benzamide

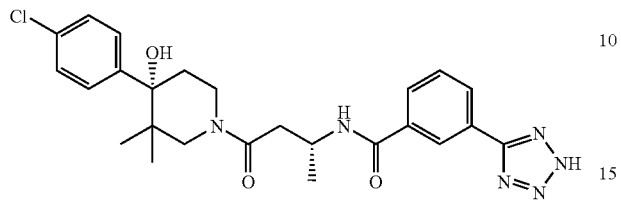

Example 4 was prepared from 3-(2-(benzyloxymethyl)-2H-tetrazol-5-yl)-N—((R)-4-((S)-4-(4-chlorophenyl)-4-hydroxy-3,3-dimethylpiperidin-1-yl)-4-oxobutan-2-yl)benzamide using the conditions described in Example 2. MS (ESI$^+$)= 497.2 (M+H)$^+$. $^1$H NMR (CD$_3$OD, 500 MHz) (NMR shows several rotamers) δ ppm 8.55 (s, 0.6 H), 8.49 (s, 0.4 H), 8.23 (d, J=7.8 Hz, 0.6 H), 8.20 (d, J=7.8 Hz, 0.4 H), 8.05 (d, J=8.2 Hz, 0.6 H), 8.00 (d, J=7.8 Hz, 0.4 H), 7.75-7.66 (m, 1 H), 7.47 (d, J=8.7 Hz, 0.9 H), 7.36-7.28 (m, 2.1 H), 7.22 (d, J=8.7 Hz, 1 H), 4.64-4.48 (m, 1.4 H), 4.11 (dt, J=13.3, 2.5 Hz, 0.6 H), 4.05 (dd, J=12.8, 1.8 Hz, 0.6 H), 3.69-3.54 (m, 1.4 H), 3.13 (td, J=12.9, 3.4 Hz, 0.6 H), 3.10-3.03 (m, 1 H), 2.98 (dd, J=15.1, 6.0 Hz, 0.4 H), 2.70-2.56 (m, 1.6 H), 2.53 (dd, J=15.1, 7.3 Hz, 0.4 H), 1.58-1.48 (m, 1 H), 1.42 (d, J=6.9 Hz, 1.8 H), 1.36 (d, J=6.4 Hz, 1.2 H), 1.35-1.26 (m, 0.6 H), 0.90 (t, J=6.9 Hz, 0.4 H), 0.84 (s, 1.2 H), 0.84 (s, 1.2 H), 0.77 (s, 1.8 H), 0.69 (s, 1.8 H); HPLC Method: Inj. Vol.=5 uL; Start % B=10, 12 Min. 100%, 15 Min. 100%, Flow Rate=1 ml/min, Wavelength 1=220, Wavelength 2=254, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=11.08 min., Col-2: Xbridge Phenyl 3.5 um, 4.6×150 mm; Retention Time=10.57 min.

Example 5

(S)-Methyl 3-(4-(4-(4-chlorophenyl)-4-hydroxy-3,3-dimethylpiperidin-1-yl)-2-methyl-4-oxobutan-2-ylcarbamoyl)benzoate

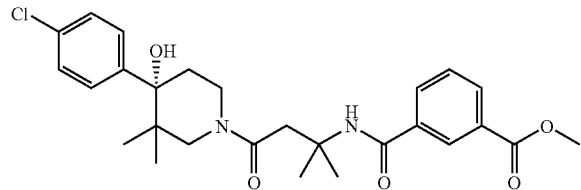 [SMILES: COC(=O)c1cccc(C(=O)NC(C)(C)CC(=O)N2CC[C@](O)(c3ccc(Cl)cc3)C(C)(C)C2)c1]

Example 5 was prepared from (S)-3-amino-1-(4-(4-chlorophenyl)-4-hydroxy-3,3-dimethylpiperidin-1-yl)-3-methylbutan-1-one, HCl and 3-(methoxycarbonyl)benzoic acid using the conditions described in Example 1, Step 8. MS (ESI$^+$)=501.1 (M+H)$^+$. $^1$H NMR (CD$_3$OD, 500 MHz) (NMR shows several rotamers) δ ppm 8.47 (s, 0.6 H), 8.42 (s, 0.4 H), 8.17 (t, J=7.9 Hz, 1 H), 8.04 (d, J=7.3 Hz, 0.6 H), 8.00 (d, J=7.7 Hz, 0.4 H), 7.65-7.56 (m, 1 H), 7.46 (d, J=8.8 Hz, 1 H), 7.38-7.22 (m, 3 H), 4.86-4.83 (m, 1 H+water), 4.18-4.05 (m, 1 H), 3.94 (s, 1.5 H), 3.92 (s, 1.5 H), 3.63-3.52 (m, 1.4 H), 3.29-3.19 (m, 1 H), 3.16-3.10 (m, 0.4 H), 3.10-3.02 (m, 0.6 H), 2.89-2.80 (m, 0.4 H), 2.72-2.54 (m, 1.6 H), 1.69-1.55 (m, 6 H), 1.55-1.44 (m, 1 H), 0.88-0.80 (m, 3 H), 0.77 (s, 1.5 H), 0.67 (s, 1.5 H); HPLC Method: Inj. Vol.=5 uL, Start % B=10, 12 Min. 100%, 15 Min. 100%, Flow Rate=1 ml/min, Wavelength 1=220, Wavelength 2=254, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=13.86 min., Col-2: Xbridge Phenyl 3.5 um, 4.6×150 mm; Retention Time=12.53 min.

Example 6

(S)-3-(4-(4-(4-Chlorophenyl)-4-hydroxy-3,3-dimethylpiperidin-1-yl)-2-methyl-4-oxobutan-2-ylcarbamoyl)benzoic acid

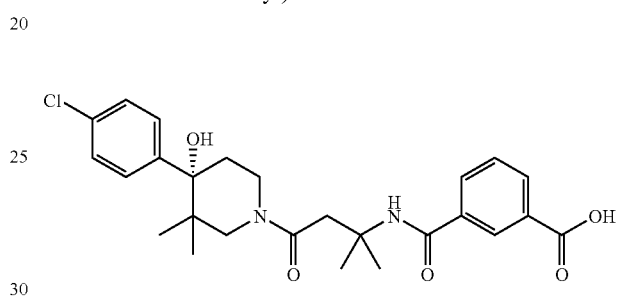

A solution of Example 5 (70 mg, 0.140 mmol) in methanol (1 mL) was treated with 1 M NaOH (0.699 mL, 0.699 mmol), and the reaction mixture was stirred for about 16 h at room temperature. After this time, the reaction mixture was treated with 1 M HCl (0.7 mL), and then injected directly onto a preparative HPLC for purification using the following conditions:

A=H$_2$O+0.05% TFA, B=acetonitrile+0.05% TFA

Column: Phenomenex Luna 5μ C18(2) 250×21.2 mm
Flow: 15 mL/min

Gradient: 0% B over 3 min, 0-100% B over 15 min, 100% B for 5 min

Fractions containing the desired product were combined and freeze-dried to yield Example 6 (48 mg, 0.099 mmol, 70.5% yield) as a colorless powder. MS (ESI$^+$)=487.2 (M+H)$^+$. $^1$H NMR (CD$_3$OD, 500 MHz) (NMR shows several rotamers) δ 8.50 (s, 0.6 H), 8.43 (s, 0.4 H), 8.21-8.13 (m, 1 H), 8.03 (d, J=7.7 Hz, 0.6 H), 7.99 (d, J=7.7 Hz, 0.4 H), 7.62-7.53 (m, 1 H), 7.46 (d, J=8.8 Hz, 0.8 H), 7.35-7.28 (m, 2 H), 7.24 (d, J=8.8 Hz, 1.2 H), 4.59 (dt, J=12.6, 2.2 Hz, 0.4 H), 4.17-4.05 (m, 1.2 H), 3.62-3.52 (m, 1.6 H), 3.27 (s, 0.4 H), 3.23 (d, J=14.8 Hz, 0.4 H), 3.11 (td, J=12.9, 3.3 Hz, 0.4 H), 3.05 (d, J=12.6 Hz, 0.6 H), 2.82 (d, J=14.3 Hz, 0.6 H), 2.67 (d, J=14.8 Hz, 0.4 H), 2.60 (tt, J=13.5, 4.4 Hz, 1 H), 1.62 (s, 1.8 H), 1.61 (s, 1.8 H), 1.58 (s, 1.2 H), 1.56 (s, 1.2 H), 1.48 (t, J=14.3 Hz, 1 H), 0.82 (s, 1.2 H), 0.81 (s, 1.2 H), 0.76 (s, 1.8 H), 0.66 (s, 1.8 H); HPLC Method: Inj. Vol.=5 uL, Start % B=10, 12 Min. 100%, 15 Min. 100%, Flow Rate=1 ml/min, Wavelength 1=220, Wavelength 2=254, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=12.12 min., Col-2: Xbridge Phenyl 3.5 um, 4.6×150 mm; Retention Time=11.35 min.

Example 7

Methyl 3-((R)-4-((S)-4-(4-chlorophenyl)-4-hydroxy-3,3-dimethylpiperidin-1-yl)-4-oxobutan-2-ylcarbamoyl)benzoate

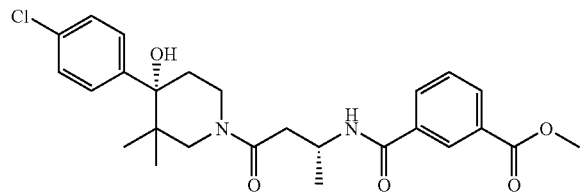 [SMILES: COC(=O)c1cccc(C(=O)N[C@H](C)CC(=O)N2CC[C@](O)(c3ccc(Cl)cc3)C(C)(C)C2)c1]

Example 7 was prepared from (R)-3-amino-1-((S)-4-(4-chlorophenyl)-4-hydroxy-3,3-dimethylpiperidin-1-yl)butan-1-one, HCl and 3-(methoxycarbonyl)benzoic acid using the conditions described in Example 1, Step 8. MS (ESI$^+$)=487.1 (M+H)$^+$. $^1$H NMR (CD$_3$OD, 500 MHz) (NMR shows several rotamers) δ ppm 8.67-8.61 (m, 0.6 H), 8.58-8.53 (m, 0.4 H), 8.36-8.24 (m, 1 H), 8.23-8.17 (m, 0.6 H), 8.17-8.10 (m, 0.4 H), 7.78-7.65 (m, 1 H), 7.60-7.54 (m, 0.8 H), 7.44-7.29 (m, 3.2 H), 4.74-4.56 (m, 1.6 H), 4.25-4.11 (m, 1.4 H), 4.06-4.01 (m, 3 H), 3.79-3.66 (m, 1.4 H), 3.27-3.12 (m, 1.6 H), 3.12-3.02 (m, 0.4 H), 2.78-2.55 (m, 2 H), 1.66-1.57 (m, 1 H), 1.50 (t, J=7.0 Hz, 1.8 H), 1.44 (t, J=6.8 Hz, 1.2 H), 1.36-1.30 (m, 0.4 H), 0.93 (br. s., 2.6 H), 0.86 (br. s., 1.7 H), 0.76 (br. s., 1.7 H); HPLC Method: Inj. Vol.=5 uL, Start % B=10, 12 Min. 100%, 15 Min. 100%, Flow Rate=1 ml/min, Wavelength 1=220, Wavelength 2=254, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=12.38 min., Col-2: Xbridge Phenyl 3.5 um, 4.6×150 mm; Retention Time=11.54 min.

Example 8

3-((R)-4-((S)-4-(4-Chlorophenyl)-4-hydroxy-3,3-dimethylpiperidin-1-yl)-4-oxobutan-2-ylcarbamoyl)benzoic acid

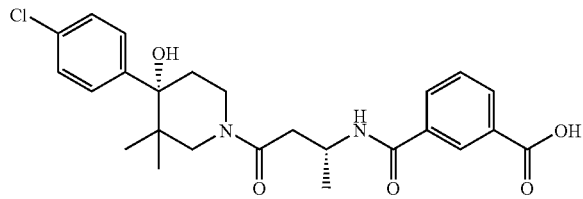 [SMILES: C[C@H](CC(=O)N1CC[C@](O)(c2ccc(Cl)cc2)C(C)(C)C1)NC(=O)c1cccc(C(=O)O)c1]

Example 8 was prepared from methyl 3-((R)-4-((S)-4-(4-chlorophenyl)-4-hydroxy-3,3-dimethylpiperidin-1-yl)-4-oxobutan-2-ylcarbamoyl)benzoate using the conditions described in Example 6. MS (ESI$^+$)=473.2 (M+H)$^+$. $^1$H NMR (CD$_3$OD, 500 MHz) (NMR shows several rotamers) δ ppm 8.54 (t, J=1.6 Hz, 0.6 H), 8.46 (t, J=1.6 Hz, 0.4 H), 8.22 (d, J=7.7 Hz, 0.6 H), 8.17 (d, J=7.7 Hz, 0.4 H), 8.08 (d, J=8.2 Hz, 0.6 H), 8.02 (d, J=7.7 Hz, 0.4 H), 7.61 (t, J=7.7 Hz, 0.6 H), 7.57 (t, J=7.7 Hz, 0.4 H), 7.47 (d, J=8.8 Hz, 0.8 H), 7.32-7.25 (m, 2 H), 7.23 (d, J=8.3 Hz, 1.2 H), 4.64-4.46 (m, 1.4 H), 4.10 (dt, J=13.2, 2.5 Hz, 0.6 H), 4.04 (dd, J=12.6, 2.2 Hz, 0.6 H), 3.67-3.53 (m, 1.4 H), 3.17-3.03 (m, 1.6 H), 2.97 (dd, J=14.9, 6.1 Hz, 0.4 H), 2.67-2.46 (m, 2 H), 1.57-1.47 (m, 1 H), 1.40 (d, J=6.6 Hz, 1.8 H), 1.34 (d, J=6.6 Hz, 1.2 H), 0.83 (s, 1.2 H), 0.82 (s, 1.2 H), 0.76 (s, 1.8 H), 0.66 (s, 1.8 H); HPLC Method: Inj. Vol.=5 uL, Start % B=10, 12 Min. 100%, 15 Min. 100%, Flow Rate=1 ml/min, Wavelength 1=220, Wavelength 2=254, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=10.92 min., Col-2: Xbridge Phenyl 3.5 um, 4.6×150 mm; Retention Time=10.45 min.

Example 9

Tert-Butyl (1R,3R)-3-(4-((S)-4-(4-chlorophenyl)-4-hydroxy-3,3-dimethylpiperidin-1-yl)-2-methyl-4-oxobutan-2-ylcarbamoyl)cyclopentylcarbamate

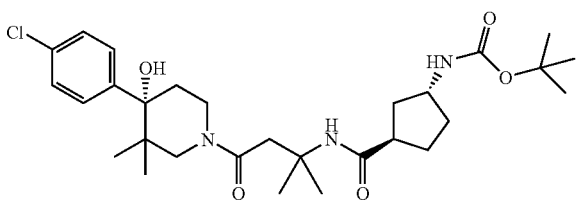 [SMILES: CC(C)(CC(=O)N1CC[C@](O)(c2ccc(Cl)cc2)C(C)(C)C1)NC(=O)[C@@H]1CC[C@@H](NC(=O)OC(C)(C)C)C1]

Example 9 was prepared from (S)-3-amino-1-(4-(4-chlorophenyl)-4-hydroxy-3,3-dimethylpiperidin-1-yl)-3-methylbutan-1-one, HCl and (1R,3R)-3-(tert-butoxycarbonylamino)cyclopentanecarboxylic acid using the conditions described in Example 1, Step 8. MS (ESI$^+$)=550.2 (M+H)$^+$. $^1$H NMR (CD$_3$OD, 500 MHz) (NMR shows several rotamers) δ ppm 7.51-7.45 (m, 2 H), 7.35-7.28 (m, 2 H), 4.63-4.51 (m, 0.5 H), 4.12-4.02 (m, 1 H), 4.02-3.92 (m, 1 H), 3.62-3.45 (m, 1.5 H), 3.22 (dd, J=13.5, 1.5 Hz, 0.5 H), 3.15-3.02 (m, 1 H), 3.01-2.89 (m, 1 H), 2.84-2.45 (m, 2.5 H), 2.09-1.84 (m, 2.5 H), 1.80-1.67 (m, 2 H), 1.63-1.36 (m, 18 H), 0.85-0.77 (m, 4 H), 0.77-0.71 (m, 2 H); HPLC Method: Inj. Vol.=5 uL, Start % B 10, 12 Min. 100%, 15 Min. 100%, Flow Rate=1 ml/min, Wavelength 1=220, Wavelength 2=254, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=13.32 min., Col-2: Xbridge Phenyl 3.5 um, 4.6×150 mm; Retention Time=12.19 min.

Example 10

(1R,3R)-3-Acetamido-N-(4-((S)-4-(4-chlorophenyl)-4-hydroxy-3,3-dimethylpiperidin-1-yl)-2-methyl-4-oxobutan-2-yl)cyclopentanecarboxamide

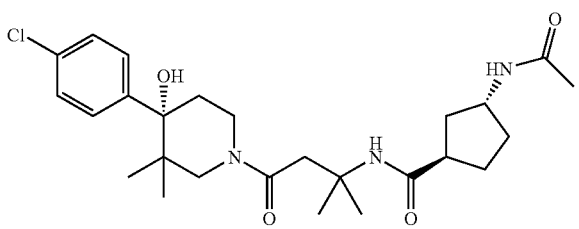 [SMILES: CC(=O)N[C@@H]1CC[C@@H](C(=O)NC(C)(C)CC(=O)N2CC[C@](O)(c3ccc(Cl)cc3)C(C)(C)C2)C1]

Step 1: (1R,3R)-3-Amino-N-(4-((S)-4-(4-chlorophenyl)-4-hydroxy-3,3-dimethylpiperidin-1-yl)-2-methyl-4-oxobutan-2-yl)cyclopentanecarboxamide, HCl

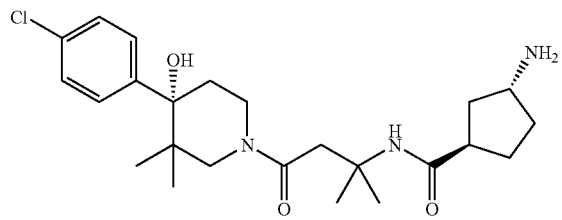 [SMILES: CC(C)(CC(=O)N1CC[C@](O)(c2ccc(Cl)cc2)C(C)(C)C1)NC(=O)[C@@H]1CC[C@@H](N)C1]

A solution of Example 9 in 4 M HCl in dioxane (2 mL, 8.00 mmol) was stirred at room temperature for 3 hours. After this time, the reaction mixture was concentrated in vacuo, and evaporated 3× from methylene chloride to remove residual HCl and dioxane, to yield the title compound (62 mg, 0.127 mmol, 100% yield) as a colorless solid. LCMS indicated the product contained a small amount of (S)-4-(4-chlorophenyl)-4-hydroxy-3,3-dimethylpiperidine. The material was used as-is in the next step. MS (ESI+)=450.2 (M+H)+.

Step 2: Example 10

A solution of (1R,3R)-3-amino-N-(4-((S)-4-(4-chlorophenyl)-4-hydroxy-3,3-dimethylpiperidin-1-yl)-2-methyl-4-oxobutan-2-yl)cyclopentanecarboxamide, HCl (51 mg, 0.105 mmol) and Hunig's Base (0.055 mL, 0.315 mmol) in methylene chloride (2 mL) was treated with acetic anhydride (9.89 μl, 0.105 mmol), and the reaction mixture was stirred for about 16 h at room temperature. The solvent was blown off with a stream of nitrogen, and the resulting residue was taken up in ethyl acetate. The mixture was washed 3× with 1 N HCl, once with water, and once with brine. The organic phase was dried over sodium sulfate and concentrated in vacuo to yield a residue. The residue was purified over a 12 g silica gel column, eluting at 30 mL/min with an ethyl acetate/hexanes gradient to yield Example 10 (24 mg, 0.049 mmol, 46.5% yield) as a colorless solid. MS (ESI+)=492.2 (M+H)+. 1H NMR (DMSO-d6, 500 MHz) (NMR shows several rotamers) δ ppm 7.77 (d, J=7.1 Hz, 1 H), 7.58 (s, 0.5 H), 7.54 (s, 0.5 H), 7.45 (d, J=8.8 Hz, 2 H), 7.39-7.33 (m, 2 H), 5.04 (d, J=3.8 Hz, 1 H), 4.47 (ddd, J=13.1, 2.1, 1.9 Hz, 0.5 H), 4.07-3.91 (m, 2 H), 3.45-3.32 (m, 1.5 H), 2.98 (d, J=14.3 Hz, 0.5 H), 2.91-2.83 (m, 1.5 H), 2.75-2.66 (m, 1.5 H), 2.59-2.51 (m, 0.5 H), 2.47-2.39 (m, 1 H), 1.90-1.77 (m, 3 H), 1.76 (s, 3 H), 1.67-1.50 (m, 2 H), 1.47-1.36 (m, 1.5 H), 1.36-1.30 (m, 6.5 H), 0.70 (s, 1.5 H), 0.68 (s, 1.5 H), 0.66 (s, 1.5 H), 0.62 (s, 1.5 H); HPLC Method: Inj. Vol.=5 uL, Start % B=10, 12 Min. 100%, 15 Min. 100%, Flow Rate=1 ml/min, Wavelength 1=220, Wavelength 2=254, Solvent A=0.05% TFA in H2O:MeCN (95:5), Solvent B=0.05% TFA in H2O:MeCN (5:95), Col-1: Sunfire C18 3.5 um, 4.6×150 mm; Retention Time=10.52 min., Col-2: Xbridge Phenyl 3.5 um, 4.6×150 mm; Retention Time=10.18 min.

Example 11

(1R,3R)-3-Acetamido-N—((R)-4-((S)-4-(4-chlorophenyl)-4-hydroxy-3,3-dimethylpiperidin-1-yl)-4-oxobutan-2-yl)cyclopentanecarboxamide

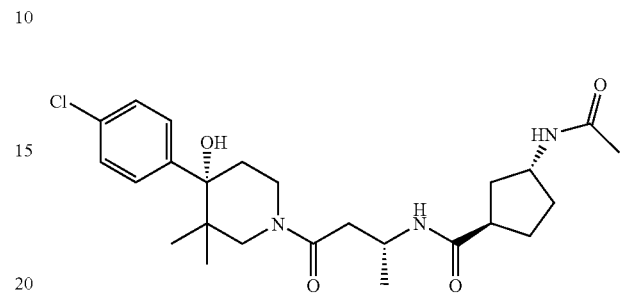

Example 11 was prepared from (R)-3-amino-1-((S)-4-(4-chlorophenyl)-4-hydroxy-3,3-dimethylpiperidin-1-yl)butan-1-one, HCl and (1R,3R)-3-(tert-butoxycarbonylamino)cyclopentanecarboxylic acid using the conditions described in Examples 9 and 10. MS (ESI+)=478.2 (M+H)+. 1H NMR (DMSO-d6, 500 MHz) (NMR shows several rotamers) δ ppm 7.71 (m, 1 H), 7.68 (d, J=8.2 Hz, 0.6 H), 7.56 (d, J=7.8 Hz, 0.4 H), 7.39 (d, J=8.7 Hz, 2 H), 7.32-7.26 (m, 2 H), 4.99 (s, 0.4 H), 4.96 (s, 0.6 H), 4.36 (ddd, J=12.6, 2.3, 2.1 Hz, 0.4 H), 4.09-3.92 (m, 2 H), 3.86 (d, J=12.4 Hz, 1 H), 3.38-3.29 (m, 1.2 H), 2.87-2.76 (m, 1 H), 2.69-2.50 (m, 3 H), 2.22-2.11 (m, 1 H), 1.85-1.72 (m, 3.4 H), 1.70 (s, 1.8 H), 1.69 (s, 1.2 H), 1.60-1.45 (m, 2 H), 1.42-1.24 (m, 2 H), 1.03 (d, J=6.9 Hz, 1.6 H), 1.00 (d, J=6.9 Hz, 1.4 H), 0.64 (s, 1.4 H), 0.62 (s, 1.4 H), 0.61 (s, 1.6 H), 0.54 (s, 1.6 H); HPLC Method: Inj. Vol.=5 uL, Start % B=10, 12 Min. 100%, 15 Min. 100%, Flow Rate=1 ml/min, Wavelength 1=220, Wavelength 2=254, Solvent A=0.05% TFA in H2O:MeCN (95:5), Solvent B=0.05% TFA in H2O:MeCN (5:95), Col-1: Sunfire C18 3.5 um, 4.6×150 mm; Retention Time=9.84 min., Col-2: Xbridge Phenyl 3.5 um, 4.6×150 mm; Retention Time=9.64 min.

Example 12

4-Chloro-N-(1-((S)-4-(4-chlorophenyl)-4-hydroxy-3,3-dimethylpiperidin-1-yl)-4-methyl-1-oxopentan-3-yl)benzamide, isomer 1

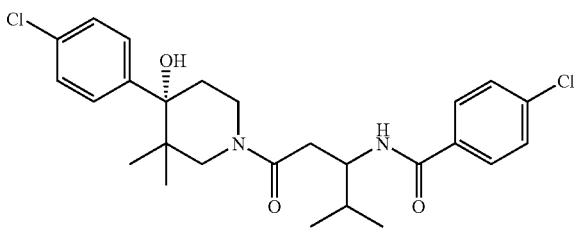 [SMILES: CC(C)C(CC(=O)N1CC[C@](O)(c2ccc(Cl)cc2)C(C)(C)C1)NC(=O)c1ccc(Cl)cc1]

Step 1: 3-Amino-1-((S)-4-(4-chlorophenyl)-4-hydroxy-3,3-dimethylpiperidin-1-yl)-4-methylpentan-1-one, HCl

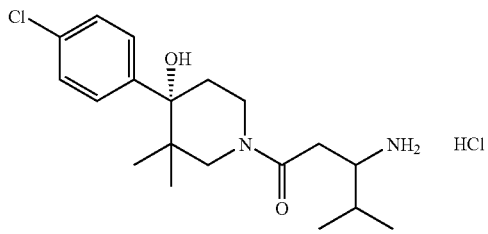 [SMILES: CC(C)C(N)CC(=O)N1CC[C@](O)(c2ccc(Cl)cc2)C(C)(C)C1 ; Cl]

The title compound was prepared from (S)-4-(4-chlorophenyl)-3,3-dimethylpiperidin-4-ol and Boc-DL-beta-leucine-OH using the procedures described in Example 1, steps 2-3. MS (ESI+)=353.5 (M+H)+.

Step 2: Example 12

A solution of 3-amino-1-((S)-4-(4-chlorophenyl)-4-hydroxy-3,3-dimethylpiperidin-1-yl)-4-methylpentan-1-one, HCl (21 mg, 0.05 mmol), 4-chlorobenzoic acid (9 mg, 0.6 mmol), HOBt (15 mg, 0.11 mmol), and triethylamine (20 mg, 0.2 mmol) in methylene chloride (1 mL) was treated with EDC (21 mg, 0.11 mmol), and the reaction mixture was stirred for about 16 hours at room temperature. After this time, the solvent was blown off with a stream of nitrogen, and the resulting residue was taken up in methanol. The resulting mixture was purified via prep HPLC using a Phenomenex Luna 5 uM C18 (2) column and eluting at 15 mL/minute with a 0-100% acetonitrile/water gradient over 30 minutes. The two diastereomers of the title compound were resolved in this HPLC purification. Fractions containing the first eluting peak were combined and freeze-dried to yield Example 12, MS (ESI+)=491.3 (M+H)+. Fractions containing the second eluting peak were combined and freeze-dried to yield isomer 2, MS (ESI+)=491.3 (M+H)+. $^1$H NMR (CD$_3$OD, 500 MHz,) (NMR shows several rotamers) δ ppm 7.80 (d, J=8.5 Hz, 1.25 H), 7.70 (d, J=8.5 Hz, 0.75 H), 7.46 (d, J=8.5 Hz, 1.25 H), 7.42-7.35 (m, 1.5 H), 7.22 (d, J=8.8 Hz, 0.75 H), 7.14 (d, J=8.8 Hz, 1.25 H), 7.05 (d, J=8.8 Hz, 1.25 H), 4.84-4.81 (m, 1 H), 4.45 (dt, J=12.7, 2.6 Hz, 0.25 H), 4.40-4.36 (m, 0.1 H), 4.27-4.18 (m, 1 H), 3.97-3.88 (m, 1.25 H), 3.79-3.75 (m, 0.1 H), 3.74-3.69 (m, 0.1 H), 3.61-3.51 (m, 0.75 H), 3.50-3.45 (m, 0.25 H), 3.41-3.35 (m, 0.25 H), 2.99 (td, J=13.0, 3.2 Hz, 0.25 H), 2.93 (d, J=12.9 Hz, 0.75 H), 2.88-2.78 (m, 0.75 H), 2.77-2.71 (m, 0.25 H), 2.63 (dd, J=14.3, 4.1 Hz, 0.75 H), 2.57-2.47 (m, 0.75 H), 2.35 (td, J=13.5, 4.8 Hz, 0.75 H), 1.99-1.88 (m, 1 H), 1.41 (dt, J=13.7, 2.7 Hz, 0.25 H), 1.36 (dt, J=13.8, 2.6 Hz, 0.75 H), 0.98 (d, J=6.9 Hz, 1.8 H), 0.96-0.87 (m, 4.2 H), 0.73 (s, 2 H), 0.65 (s, 2 H), 0.51 (s, 2 H).

Example 13

Methyl 3-(1-((S)-4-(4-chlorophenyl)-4-hydroxy-3,3-dimethylpiperidin-1-yl)-4-methyl-1-oxopentan-3-ylcarbamoyl)benzoate, isomer 2

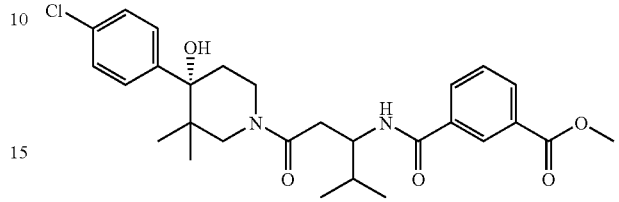

Example 13 was prepared from 3-amino-1-((S)-4-(4-chlorophenyl)-4-hydroxy-3,3-dimethylpiperidin-1-yl)-4-methylpentan-1-one, HCl and mono-methyl isophthalate using the procedure described in Example 12, Step 2. The two diastereomers of the title compound were resolved in this HPLC purification. Fractions containing the first eluting peak were combined and freeze-dried to yield isomer 1, MS (ESI+)= 515.4 (M+H)+. Fractions containing the second eluting peak were combined and freeze-dried to yield Example 13, MS (ESI+)=515.4 (M+H)+. $^1$H NMR (CD$_3$OD, 500 MHz,) (NMR shows several rotamers) δ ppm 8.38 (t, J=1.6 Hz, 0.7 H), 8.36 (t, J=1.6 Hz, 0.3 H), 8.11-8.06 (m, 1 H), 7.95 (dt, J=7.8, 1.4 Hz, 1 H), 7.54-7.47 (m, 1 H), 7.42 (d, J=8.7 Hz, 1.4 H), 7.38 (d, J=8.7 Hz, 0.6 H), 7.25-7.20 (m, 2 H), 4.44-4.34 (m, 0.7 H), 4.26 (td, J=7.8, 4.6 Hz, 0.3 H), 3.91 (dd, J=12.8, 2.3 Hz, 0.7 H), 3.87-3.80 (m, 3.3 H), 3.60-3.52 (m, 1 H), 3.30 (dd, J=13.1, 2.1 Hz, 0.3 H), 3.03-2.90 (m, 2 H), 2.87-2.76 (m, 1 H), 2.59-2.47 (m, 1.7 H), 1.96-1.85 (m, 1.2 H), 1.49 (dt, J=14.2, 2.7 Hz, 0.7 H), 1.41 (dt, J=14.2, 2.7 Hz, 0.3 H), 1.01-0.90 (m, 6.4 H), 0.75 (d, J=1.8 Hz, 2 H), 0.65 (s, 2 H), 0.48 (s, 2 H).

Example 14

3-(1-((S)-4-(4-Chlorophenyl)-4-hydroxy-3,3-dimethylpiperidin-1-yl)-4-methyl-1-oxopentan-3-ylcarbamoyl)benzoic acid

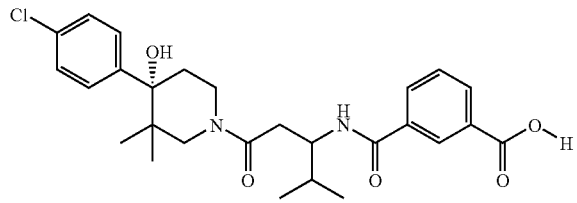 [SMILES: CC(C)C(CC(=O)N1CC[C@](O)(c2ccc(Cl)cc2)C(C)(C)C1)NC(=O)c1cccc(C(=O)O)c1]

Example 13 was hydrolyzed to Example 14 by the procedure described in Example 6. MS (ESI+)=501.3 (M+H)+. $^1$H NMR (CD$_3$OD, 500 MHz,) (NMR shows several rotamers) δ ppm 8.55 (t, J=1.8 Hz, 0.3 H), 8.46-8.39 (m, 1 H), 8.23 (dt, J=7.8, 1.4 Hz, 0.3 H), 8.18-8.11 (m, 0.6 H), 8.08 (dd, J=7.8, 1.4 Hz, 0.3 H), 8.05-8.01 (m, 0.2 H), 7.99-7.94 (m, 0.6 H), 7.67-7.59 (m, 0.5 H), 7.58-7.49 (m, 0.7 H), 7.47 (d, J=8.7 Hz, 0.7 H), 7.43 (d, J=8.7 Hz, 0.6 H), 7.31-7.24 (m, 1.2 H), 7.16 (d, J=8.7 Hz, 0.6 H), 7.10 (d, J=8.7 Hz, 0.6 H), 4.54-4.26 (m, 0.8 H), 4.03-3.94 (m, 0.9 H), 3.93-3.86 (m, 0.3 H), 3.66-3.52 (m, 1 H), 3.38-3.33 (m, 0.3 H), 3.10-2.91 (m, 1.8 H), 2.91-2.77 (m, 0.7 H), 2.69-2.52 (m, 1.4 H), 2.41 (td, J=13.6, 4.8 Hz, 0.4 H), 2.06-1.91 (m, 1 H), 1.58-1.51 (m, 0.4 H), 1.49-1.36 (m, 0.8 H), 1.07-0.95 (m, 6 H), 0.79 (s, 2 H), 0.70 (s, 1 H), 0.70 (s, 1 H), 0.55 (s, 2 H).

Example 15

(S)—N-(4-(2-(4-(4-Chlorophenyl)-4-hydroxy-3,3-dimethylpiperidin-1-yl)-2-oxoethyl)tetrahydro-2H-pyran-4-yl)benzamide

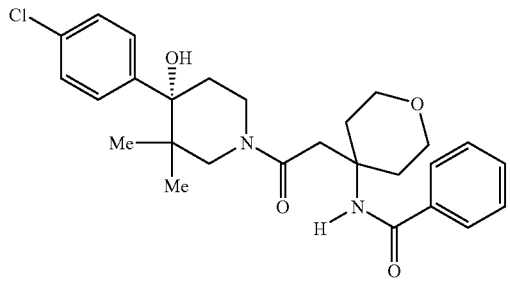 [SMILES: CC1(C)CN(C(=O)CC2(NC(=O)c3ccccc3)CCOCC2)CC[C@]1(O)c1ccc(Cl)cc1]

Step 1: Methyl 2-(4-(tert-butoxycarbonylamino)tetrahydro-2H-pyran-4-yl)acetate

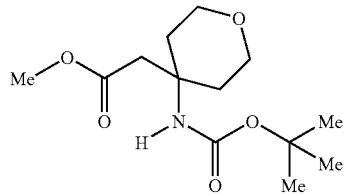 [SMILES: COC(=O)CC1(NC(=O)OC(C)(C)C)CCOCC1]

To a solution of methyl 2-(4-aminotetrahydro-2H-pyran-4-yl)acetate p-toluenesulfonic acid salt (prepared in the similar manner as described in *Bioorg. Med. Chem. Leu.* 2006, 16, 2699-2704, 1.0 g, 2.9 mmol) in anhydrous dioxane (5 mL) was sequentially added diisopropylethylamine (1 mL, 5.8 mmol) and (BOC)$_2$O (1.26 g, 5.8 mmol) at room temperature. Upon completion of addition, the reaction mixture was stirred at room temperature for 60 h, concentrated under reduced pressure and partitioned between ethyl acetate (30 mL) and 1N HCl (10 mL). The ethyl acetate layer was washed with 1N NaOH (10 mL), brine (10 mL), dried over sodium sulfate and concentrated under reduced pressure to yield the title compound (1.0 g) as an oil, which was used in the next step without further purification.

Step 2: 2-(4-(tert-Butoxycarbonylamino)tetrahydro-2H-pyran-4-yl)acetic acid

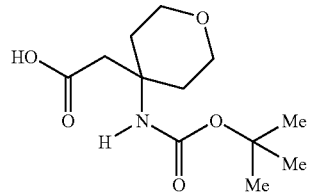 [SMILES: CC(C)(C)OC(=O)NC1(CC(=O)O)CCOCC1]

To a solution of methyl 2-(4-(tert-butoxycarbonylamino)tetrahydro-2H-pyran-4-yl)acetate (0.73 g, 2.67 mmol) in ethanol (5 mL) and water (2 mL) was added potassium hydroxide (0.3 g, 5.34 mmol) at room temperature. Upon completion of addition, the reaction mixture was heated at 60° C. for 4 hours and then partitioned between ethyl acetate (30 mL) and 1N HCl (10 mL). The ethyl acetate layer was separated, washed with brine (20 mL), dried over sodium sulfate and concentrated to yield the title compound (0.615 g) as a white solid. MS found: (M–H)$^+$=258.2.

Step 3: (S)-tert-Butyl 4-(2-(4-(4-chlorophenyl)-4-hydroxy=3,3-dimethylpiperidin-1-yl)-2-oxoethyl)tetrahydro-2H-pyran-4-ylcarbamate

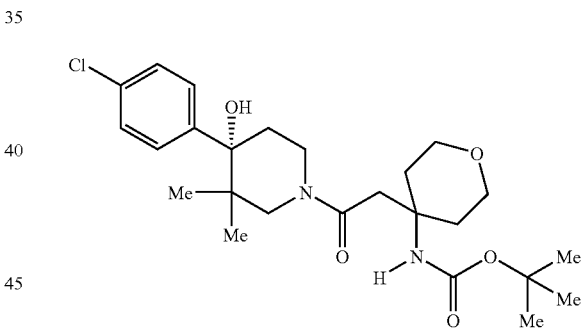

To a solution of 2-(4-(tert-butoxycarbonylamino)tetrahydro-2H-pyran-4-yl)acetic acid (step 2, 0.125 g, 0.48 mmol) in anhydrous DMF (1 mL) was sequentially added (S)-4-(4-chlorophenyl)-3,3-dimethylpiperidin-4-ol (0.182 g, 0.48 mmol), diisopropylethylamine (0.17 mL, 0.96 mmol) and (benzotriazol-1-yloxy)tris(dimethylamino)phosphonium hexafluorophosphate (0.225 g, 0.50 mmol) at room temperature. Upon completion of addition, the reaction mixture was stirred at room temperature for 20 h and then partitioned between ethyl acetate (20 mL) and 1N HCl (10 mL). The ethyl acetate layer was separated, washed sequentially with 1N NaOH (10 mL), brine (10 mL), dried over sodium sulfate and concentrated to yield a residue. The residue was purified using a pre-packed silica gel column (40 g) employing hexane and ethyl acetate. The desired fractions were collected and concentrated under reduced pressure to yield the title compound (0.175 g) as a foamy solid. MS (ESI$^+$)=481.1 (M+H)$^+$.

Step 4: (S)-2-(4-Aminotetrahydro-2H-pyran-4-yl)-1-(4-(4-chlorophenyl)-4-hydroxy-3,3-dimethylpiperidin-1-yl)ethanone

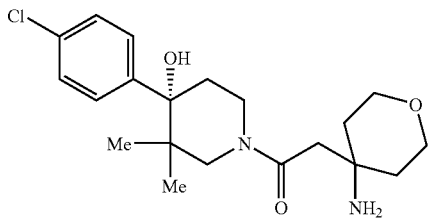 [SMILES: CC1(C)CN(C(=O)CC2(N)CCOCC2)CC[C@]1(O)c1ccc(Cl)cc1]

To (S)-tert-butyl 4-(2-(4-(4-chlorophenyl)-4-hydroxy-3,3-dimethylpiperidin-1-yl)-2-oxoethyl)tetrahydro-2H-pyran-4-ylcarbamate (from step 3, 0.17 g, 0.35 mmol) was added 4.0N HCl in dioxane (2 mL) at room temperature. Upon completion of addition, the reaction mixture was stirred at room temperature for 24 h. At the conclusion of this period, the reaction mixture was concentrated under reduced pressure and then partitioned between ethyl acetate (20 mL) and 1N NaOH (10 mL). The ethyl acetate layer was separated, washed with brine (20 mL), dried over sodium sulfate and concentrated under reduced pressure to yield the title compound (0.135 g) as a foamy solid. MS (ESI$^+$)=381.1 (M+H)$^+$.

Step 5: Example 15

To a solution of (S)-2-(4-aminotetrahydro-2H-pyran-4-yl)-1-(4-(4-chlorophenyl)-4-hydroxy-3,3-dimethylpiperidin-1-yl)ethanone (0.07 g, 0.18 mmol) in dichloromethane (2 mL) was sequentially added diisopropylethylamine (71 μl, 0.34 mmol) and benzoyl chloride (26 μl, 0.19 mmol) at room temperature, over a period of three minutes. Upon completion of addition, the reaction mixture was stirred for 30 minutes. After 30 min., the reaction mixture was concentrated to yield a residue. The residue was subjected to preparative HPLC (Phenomenex S5 30×100 mm, 10 min. gradient; Solvent A: 10% MeOH, 90% H$_2$O, 0.1% TFA; Solvent B: 90% MeOH, 10% H$_2$O, 0.1% TFA; wavelength: 254 nM). The desired fractions were collected, concentrated under reduced pressure and the residue partitioned between dichloromethane (20 mL) and sat. aq. sodium bicarbonate (10 mL). The dichloromethane layer was dried over sodium sulfate and concentrated under reduced pressure to yield Example 15 (0.05 g) as a white solid. MS (ESI$^+$)=485.09 (M+H).

Example 16

(S)-1-(4-(4-(4-Chlorophenyl)-4-hydroxy-3,3-dimethylpiperidin-1-yl)-2-methyl-4-oxobutan-2-yl)-3-phenylurea

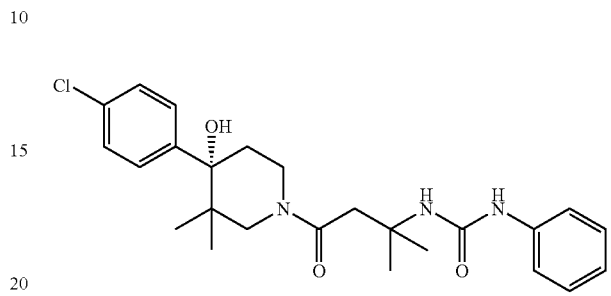

(S)-3-Amino-1-(4-(4-chlorophenyl)-4-hydroxy-3,3-dimethylpiperidin-1-yl)-3-methylbutan-1-one, HCl (25 mg, 0.067 mmol, prepared as described in Example 1, Step 3) was stirred in THF (3 ml) at 25° C. Triethylamine (9.28 μL, 0.067 mmol) was added thereto followed by phenyl isocyanate (7.93 mg, 0.067 mmol). The mixture was stirred for 20 hours. The reaction was stripped and then purified by preparatory HPLC/MS. Obtained (S)-1-(4-(4-(4-chlorophenyl)-4-hydroxy-3,3-dimethylpiperidin-1-yl)-2-methyl-4-oxobutan-2-yl)-3-phenylurea (25 mg, 0.044 mmol, 65.6% yield) as a white solid. MS found: (M+H)$^+$=458.10. $^1$H NMR (CD$_3$OD, 400 MHz) (NMR shows several rotamers) δ 7.48-7.35 (m, 2H), 7.34-7.20 (m, 4H), 7.18 (d, 1H, J=8 Hz), 7.12 (d, 1H, J=8 Hz), 7.02-6.92 (m, 1H), 4.61-4.57 (m, 0.5H), 4.23-4.17 (m, 0.5H), 4.11-4.06 (m, 0.5H), 3.63-3.37 (m, 2.5H), 3.17-2.99 (m, 1H), 2.68-2.45 (m, 2H), 1.57-1.37 (m, 7H), 0.82-0.65 (m, 6H); LCMS method: Inj. Vol.=2000 uL, Start % B=30, Final % B=100, Gradient Time=18 min, Flow Rate=20 ml/min, Wavelength=220, Solvent A=10% MeOH−90% H$_2$O−0.1% TFA, Solvent B=90% MeOH−10%−H$_2$O 0.1% TFA, Column 2=Waters Sunfire C-18 19×100 mm, Retention Time=16.14 minutes.

Examples 17 to 62

Examples 17 to 62, as described in Table 1, were prepared in a similar manner as described for the preparation of Examples 1 to 16. The data in the "MS" column represents the values observed for the (M+H)$^+$ ions in MS experiments.

TABLE 1

| Example No. | Structure | Mass Spec (M + H)$^+$ |
|---|---|---|
| 17 | ![structure] | 429 |

TABLE 1-continued

| Example No. | Structure | Mass Spec (M + H)+ |
|---|---|---|
| 18 | 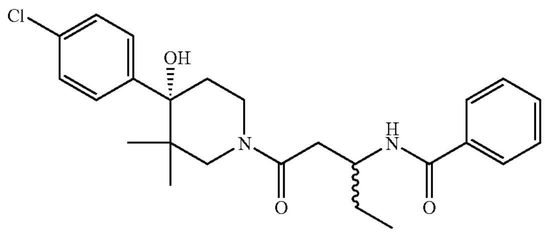 [SMILES: CCC(CC(=O)N1CC[C@](O)(c2ccc(Cl)cc2)C(C)(C)C1)NC(=O)c1ccccc1] | 443 |
| 19 | 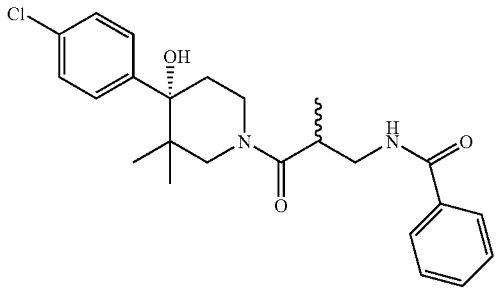 [SMILES: CC(CNC(=O)c1ccccc1)C(=O)N1CC[C@](O)(c2ccc(Cl)cc2)C(C)(C)C1] | 451 |
| 20 | 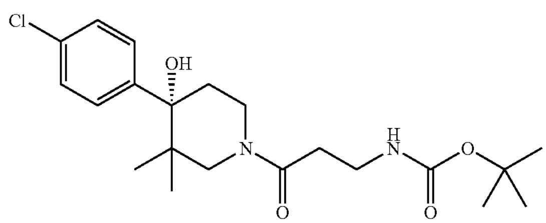 [SMILES: CC(C)(C)OC(=O)NCCC(=O)N1CC[C@](O)(c2ccc(Cl)cc2)C(C)(C)C1] | 411 |
| 21 | 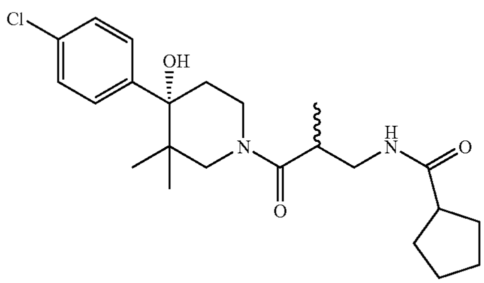 [SMILES: CC(CNC(=O)C1CCCC1)C(=O)N1CC[C@](O)(c2ccc(Cl)cc2)C(C)(C)C1] | 421 |
| 22 | 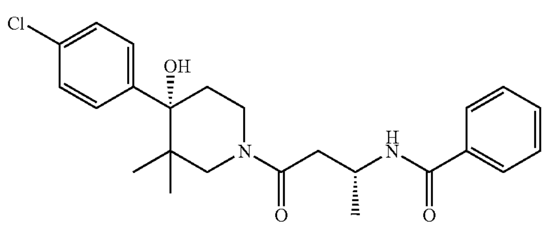 [SMILES: C[C@H](CC(=O)N1CC[C@](O)(c2ccc(Cl)cc2)C(C)(C)C1)NC(=O)c1ccccc1] | 429 |
| 23 | 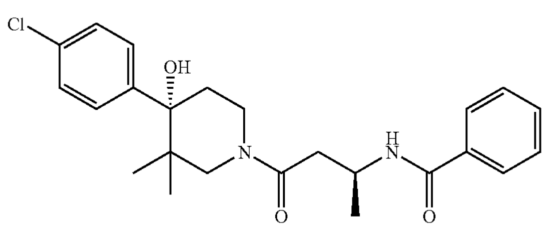 [SMILES: C[C@@H](CC(=O)N1CC[C@](O)(c2ccc(Cl)cc2)C(C)(C)C1)NC(=O)c1ccccc1] | 429 |

TABLE 1-continued

| Example No. | Structure | Mass Spec (M + H)+ |
|---|---|---|
| 24 | 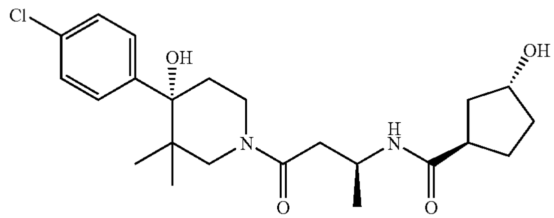 [SMILES: C[C@@H](CC(=O)N1CC[C@](O)(c2ccc(Cl)cc2)C(C)(C)C1)NC(=O)[C@@H]1CC[C@@H](O)C1] | 437 |
| 25 | 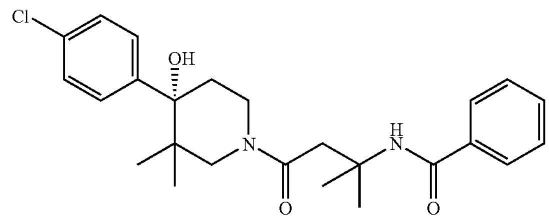 [SMILES: CC(C)(CC(=O)N1CC[C@](O)(c2ccc(Cl)cc2)C(C)(C)C1)NC(=O)c1ccccc1] | 443 |
| 26 | 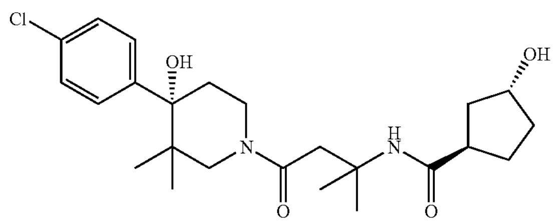 [SMILES: CC(C)(CC(=O)N1CC[C@](O)(c2ccc(Cl)cc2)C(C)(C)C1)NC(=O)[C@@H]1CC[C@@H](O)C1] | See footnote a) |
| 27 | 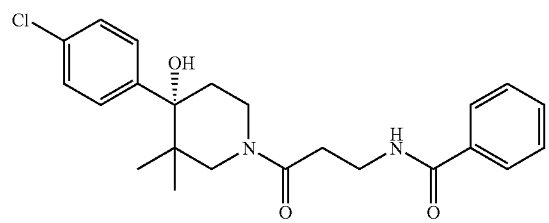 [SMILES: CC1(C)CN(C(=O)CCNC(=O)c2ccccc2)CC[C@]1(O)c1ccc(Cl)cc1] | 415 |
| 28 | 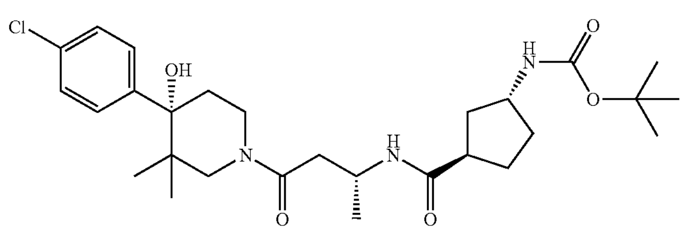 [SMILES: C[C@H](CC(=O)N1CC[C@](O)(c2ccc(Cl)cc2)C(C)(C)C1)NC(=O)[C@@H]1CC[C@@H](NC(=O)OC(C)(C)C)C1] | 536 |
| 29 | 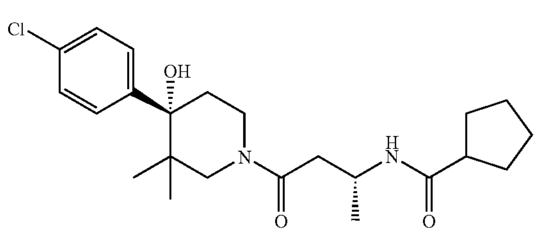 [SMILES: C[C@H](CC(=O)N1CC[C@](O)(c2ccc(Cl)cc2)C(C)(C)C1)NC(=O)C1CCCC1] | 421 |

TABLE 1-continued

| Example No. | Structure | Mass Spec (M + H)+ |
|---|---|---|
| 30 | 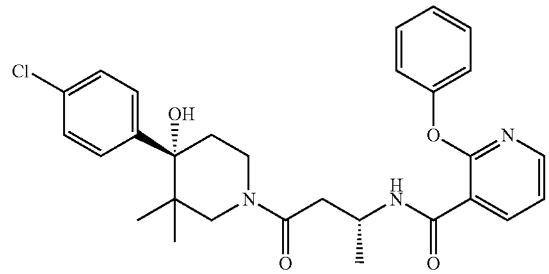 [SMILES: C[C@H](CC(=O)N1CC[C@](O)(c2ccc(Cl)cc2)C(C)(C)C1)NC(=O)c1cccnc1Oc1ccccc1] | 522 |
| 31 | 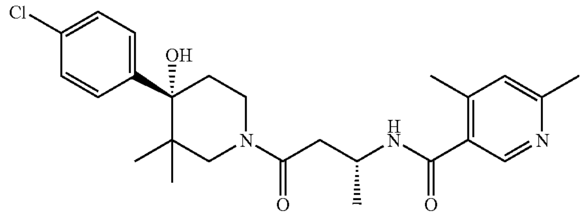 [SMILES: Cc1cc(C)c(C(=O)N[C@H](C)CC(=O)N2CC[C@](O)(c3ccc(Cl)cc3)C(C)(C)C2)cn1] | 458 (TFA salt) |
| 32 | 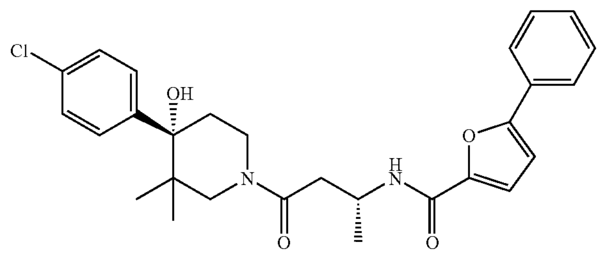 [SMILES: C[C@H](CC(=O)N1CC[C@](O)(c2ccc(Cl)cc2)C(C)(C)C1)NC(=O)c1ccc(-c2ccccc2)o1] | 495 |
| 33 | 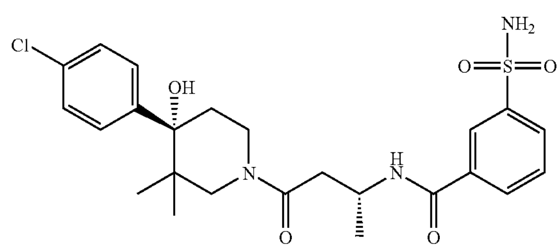 [SMILES: C[C@H](CC(=O)N1CC[C@](O)(c2ccc(Cl)cc2)C(C)(C)C1)NC(=O)c1cccc(S(N)(=O)=O)c1] | 508 |
| 34 | 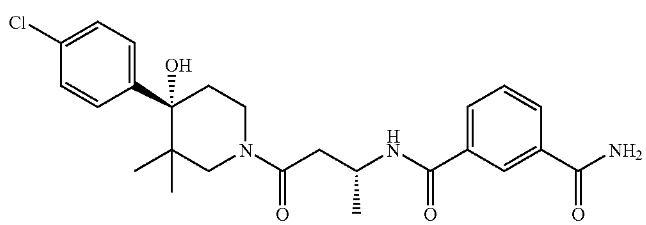 [SMILES: C[C@H](CC(=O)N1CC[C@](O)(c2ccc(Cl)cc2)C(C)(C)C1)NC(=O)c1cccc(C(N)=O)c1] | 472 |
| 35 | 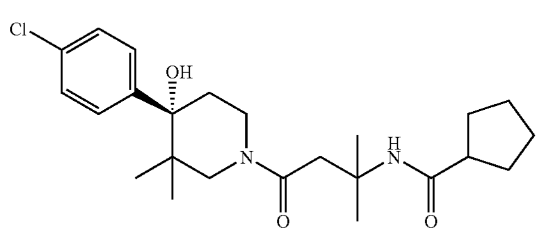 [SMILES: CC(C)(CC(=O)N1CC[C@](O)(c2ccc(Cl)cc2)C(C)(C)C1)NC(=O)C1CCCC1] | 435 |

TABLE 1-continued

| Example No. | Structure | Mass Spec (M + H)+ |
|---|---|---|
| 36 | 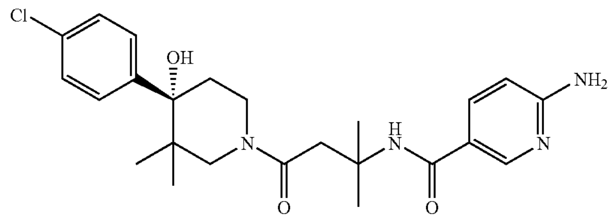 [SMILES: CC(C)(CC(=O)N1CC[C@](O)(c2ccc(Cl)cc2)C(C)(C)C1)NC(=O)c1ccc(N)nc1] | 459 (TFA salt) |
| 37 | 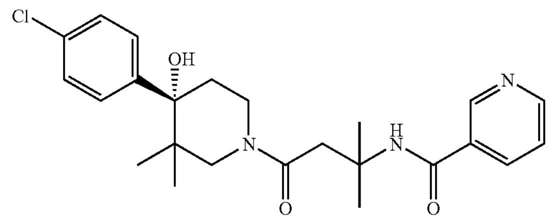 [SMILES: CC(C)(CC(=O)N1CC[C@](O)(c2ccc(Cl)cc2)C(C)(C)C1)NC(=O)c1cccnc1] | 444 (TFA salt) |
| 38 | 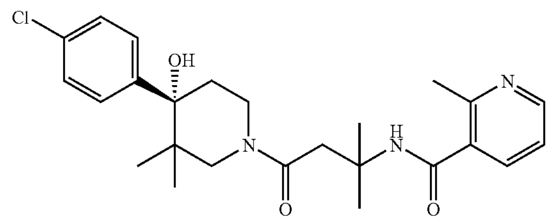 [SMILES: Cc1ncccc1C(=O)NC(C)(C)CC(=O)N1CC[C@](O)(c2ccc(Cl)cc2)C(C)(C)C1] | 458 (TFA salt) |
| 39 | 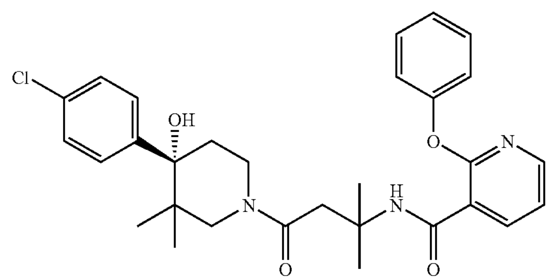 [SMILES: CC(C)(CC(=O)N1CC[C@](O)(c2ccc(Cl)cc2)C(C)(C)C1)NC(=O)c1cccnc1Oc1ccccc1] | 536 |
| 40 | 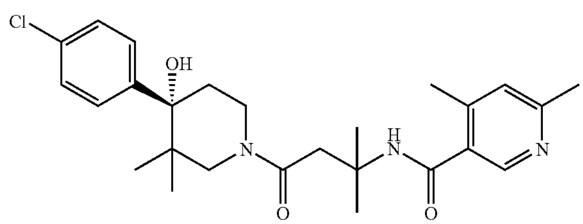 [SMILES: Cc1cc(C)c(C(=O)NC(C)(C)CC(=O)N2CC[C@](O)(c3ccc(Cl)cc3)C(C)(C)C2)cn1] | 472 (TFA salt) |
| 41 | 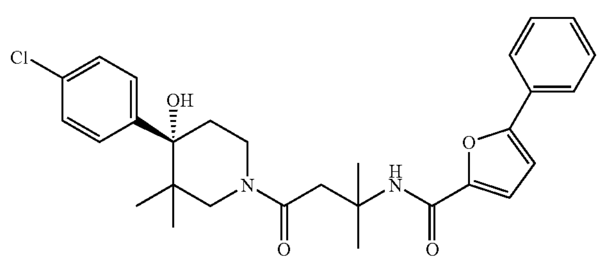 [SMILES: CC(C)(CC(=O)N1CC[C@](O)(c2ccc(Cl)cc2)C(C)(C)C1)NC(=O)c1ccc(-c2ccccc2)o1] | 509 |

TABLE 1-continued

| Example No. | Structure | Mass Spec (M + H)+ |
|---|---|---|
| 42 | 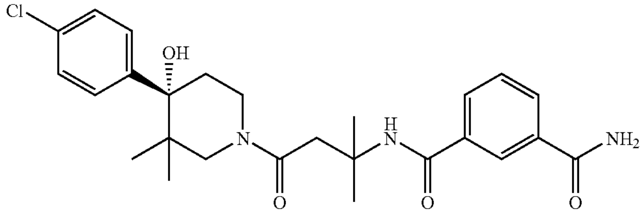 [SMILES: CC(C)(CC(=O)N1CC[C@](O)(c2ccc(Cl)cc2)C(C)(C)C1)NC(=O)c1cccc(C(N)=O)c1] | 486 |
| 43 | 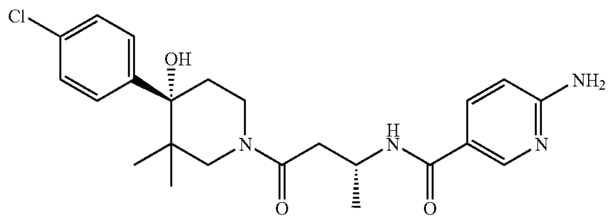 [SMILES: C[C@H](CC(=O)N1CC[C@](O)(c2ccc(Cl)cc2)C(C)(C)C1)NC(=O)c1ccc(N)nc1] | 445 |
| 44 | 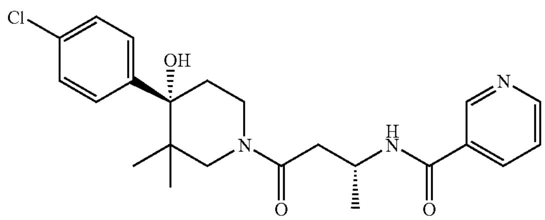 [SMILES: C[C@H](CC(=O)N1CC[C@](O)(c2ccc(Cl)cc2)C(C)(C)C1)NC(=O)c1cccnc1] | 430 |
| 45 | 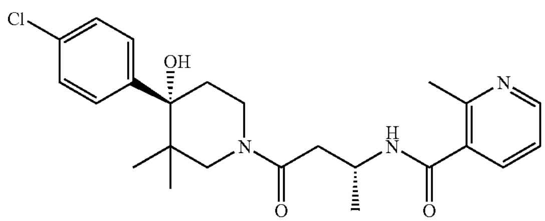 [SMILES: Cc1ncccc1C(=O)N[C@H](C)CC(=O)N1CC[C@](O)(c2ccc(Cl)cc2)C(C)(C)C1] | 444 |
| 46 | 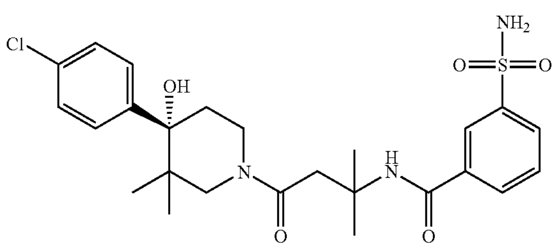 [SMILES: CC(C)(CC(=O)N1CC[C@](O)(c2ccc(Cl)cc2)C(C)(C)C1)NC(=O)c1cccc(S(N)(=O)=O)c1] | 522 |
| 47 | 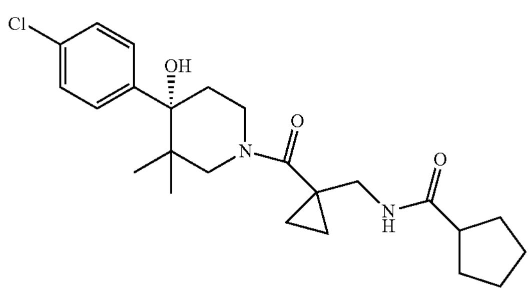 [SMILES: CC1(C)CN(C(=O)C2(CNC(=O)C3CCCC3)CC2)CC[C@]1(O)c1ccc(Cl)cc1] | 433 |

TABLE 1-continued

| Example No. | Structure | Mass Spec (M + H)+ |
|---|---|---|
| 48 | 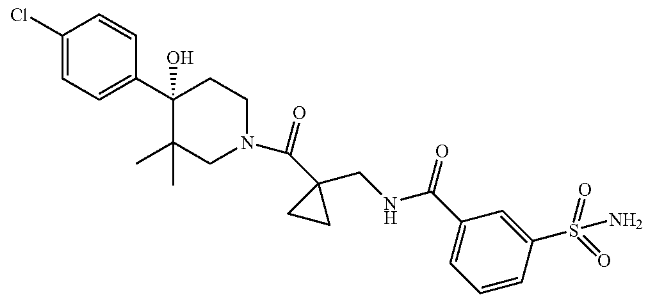 [SMILES: CC1(C)CN(C(=O)C2(CNC(=O)c3cccc(S(N)(=O)=O)c3)CC2)CC[C@]1(O)c1ccc(Cl)cc1] | 520 |
| 49 | 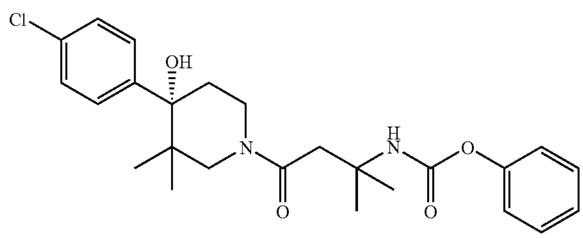 | 459 |
| 50 | 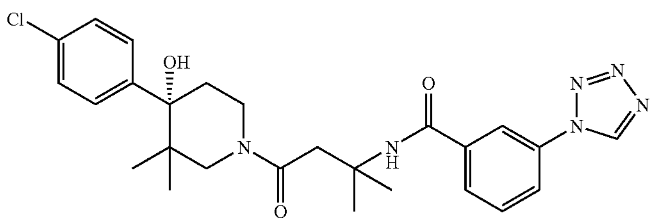 [SMILES: CC(C)(CC(=O)N1CC[C@](O)(c2ccc(Cl)cc2)C(C)(C)C1)NC(=O)c1cccc(-n2cnnn2)c1] | 511 |
| 51 | 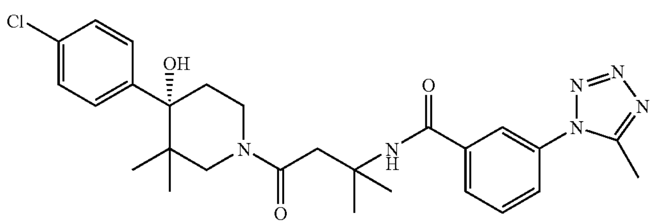 [SMILES: Cc1nnnn1-c1cccc(C(=O)NC(C)(C)CC(=O)N2CC[C@](O)(c3ccc(Cl)cc3)C(C)(C)C2)c1] | 525 |
| 52 | 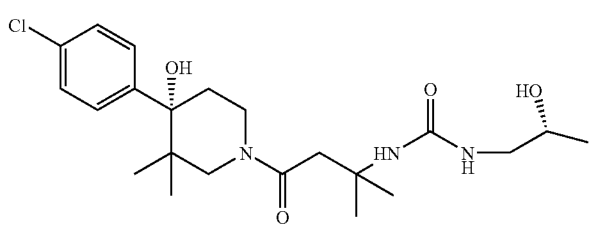 [SMILES: C[C@@H](O)CNC(=O)NC(C)(C)CC(=O)N1CC[C@](O)(c2ccc(Cl)cc2)C(C)(C)C1] | 440 |
| 53 | 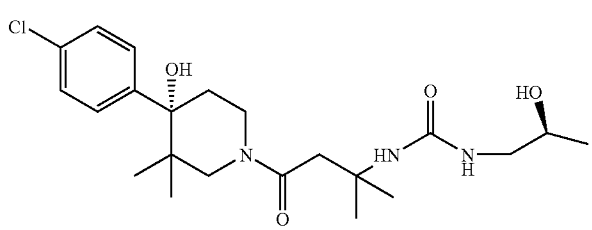 [SMILES: C[C@H](O)CNC(=O)NC(C)(C)CC(=O)N1CC[C@](O)(c2ccc(Cl)cc2)C(C)(C)C1] | 440 |

TABLE 1-continued

| Example No. | Structure | Mass Spec (M + H)+ |
|---|---|---|
| 54 | 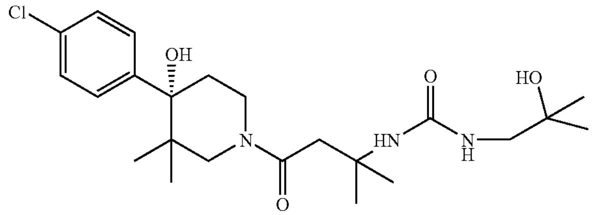 [SMILES: CC(C)(O)CNC(=O)NC(C)(C)CC(=O)N1CC[C@](O)(c2ccc(Cl)cc2)C(C)(C)C1] | 454 |
| 55 | 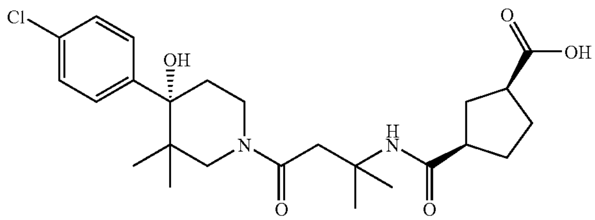 [SMILES: CC(C)(CC(=O)N1CC[C@](O)(c2ccc(Cl)cc2)C(C)(C)C1)NC(=O)[C@@H]1CC[C@H](C(=O)O)C1] | 479 |
| 56 | 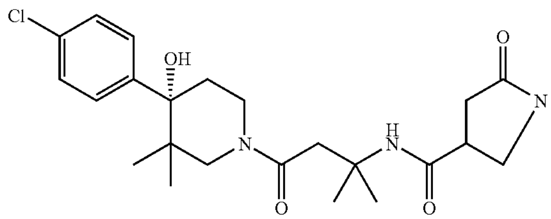 [SMILES: CC(C)(CC(=O)N1CC[C@](O)(c2ccc(Cl)cc2)C(C)(C)C1)NC(=O)C1CNC(=O)C1] | 450 |
| 57 | 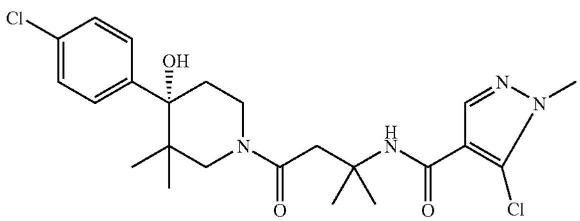 [SMILES: Cn1ncc(C(=O)NC(C)(C)CC(=O)N2CC[C@](O)(c3ccc(Cl)cc3)C(C)(C)C2)c1Cl] | 481 |
| 58 | 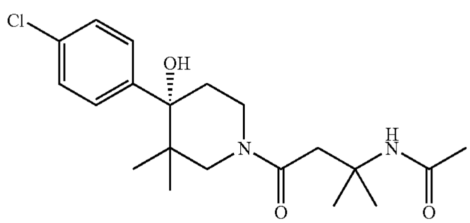 [SMILES: CC(=O)NC(C)(C)CC(=O)N1CC[C@](O)(c2ccc(Cl)cc2)C(C)(C)C1] | 381 |
| 59 | 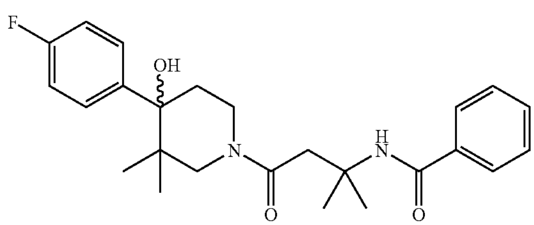 [SMILES: CC(C)(CC(=O)N1CCC(O)(c2ccc(F)cc2)C(C)(C)C1)NC(=O)c1ccccc1] | 427 |
| 60 | 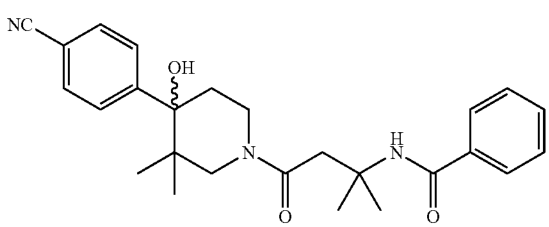 | 434 |

TABLE 1-continued

| Example No. | Structure | Mass Spec (M + H)+ |
|---|---|---|
| 61 | ![structure 61] | 429.3 |
| 62 | ![structure 62] | 459.2 | a) $^1$H NMR (400 MHz, CD$_3$OD, rotomeric) δ ppm 7.45 (2 H, m), 7.19-7.40 (2 H, m), 4.55 (0.1 H, br. d), 4.33 (0.6 H, br. s), 3.97-4.21 (1.7 H, m), 3.52 (1.3 H, m), 2.79-3.21 (3 H, m), 2.28-2.79 (1.3 H, m), 1.33-2.17 (13 H, m), 1.23 (1 H, m, +EtOAc), 0.62-0.96 (6 H, m).

Example 63

1-(4-((S)-4-(4-Chlorophenyl)-4-hydroxy-3,3-dimethylpiperidin-1-yl)-2-methyl-4-oxobutan-2-yl)-3-((S)-3-hydroxy-3-methylbutan-2-yl)urea

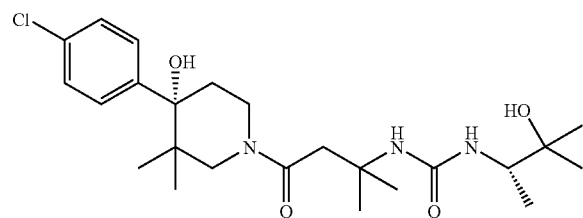 [SMILES: C[C@H](NC(=O)NC(C)(C)CC(=O)N1CC[C@](O)(c2ccc(Cl)cc2)C(C)(C)C1)C(C)(C)O]

Step 1: (S)-tert-Butyl 3-hydroxy-3-methylbutan-2-ylcarbamate

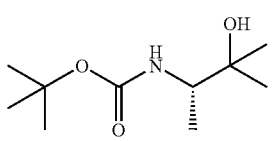

To a colorless solution of (S)-methyl 2-(tert-butoxycarbonylamino) propanoate (2.0 g, 9.84 mmol) in THF (14 mL) at 0° C. was added 3.0M CH$_3$MgBr (13.97 mL, 41.9 mmol) dropwise via an addition funnel over 10 minutes, during which time the solution turned yellow then colorless with white solids present. After the addition was complete, the reaction mixture was allowed to warm to RT and to stir overnight. Carefully, under nitrogen, the workup entailed the slow dropwise addition of saturated ammonium chloride (25 ml). Gas evolution and foaming were observed. After the addition was complete, the suspension became a solution which was extracted with methylene chloride (2x). The organic layers were combined, dried over sodium sulfate and then stripped to give (S)-tert-butyl 3-hydroxy-3-methylbutan-2-ylcarbamate (2.00 g, 9.84 mmol, 100% yield) as a colorless oil as product. MS found: (M+H–t-butyl)$^+$=148.06.

Step 2: (S)-3-Amino-2-methylbutan-2-ol HCl (S)-tert-Butyl 3-hydroxy-3-methylbutan-2-ylcarbamate (2.00 g, 9.84 mmol) was dissolved in dioxane (5 mL) at 25° C. with stirring under nitrogen and then 4N HCl in dioxane (7.38 mL, 29.5 mmol) was added, followed by 1 ml of t-butanol. The reaction was stirred for 3 hours during which time some solids precipitated and the reaction became darker in color. LC/MS showed that the reaction was essentially complete, judged by the lack of the 148 mass for starting material minus t-butyl. Et$_2$O (50 mL) was added and the mixture stirred for 10 minutes. The solids which were present were filtered and quickly placed under high vacuum. Obtained (S)-3-amino-2-methylbutan-2-ol, HCl (1.19 g, 8.52 mmol, 87% yield) as a tan solid.

Step 3: (S)-Phenyl 4-(4-(4-chlorophenyl)-4-hydroxy-3,3-dimethylpiperidin-1-yl)-2-methyl-4-oxobutan-2-ylcarbamate

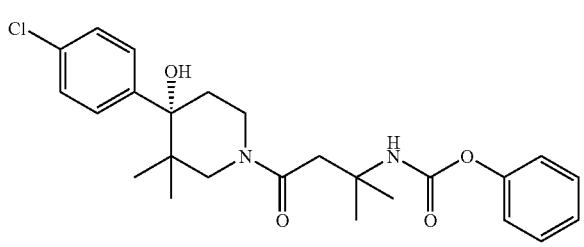 [SMILES: CC(C)(CC(=O)N1CC[C@](O)(c2ccc(Cl)cc2)C(C)(C)C1)NC(=O)Oc1ccccc1]

(S)-3-Amino-1-(4-(4-chlorophenyl)-4-hydroxy-3,3-dimethylpiperidin-1-yl)-3-methylbutan-1-one, HCl (prepared in the manner described in Example 1, Step 3, 200 mg, 0.533 mmol) and triethylamine (0.074 ml, 0.533 mmol) were mixed in methylene chloride (10 ml) with stirring at RT and then cooled to 0° C. A solution of phenyl carbonochloridate (83 mg, 0.533 mmol) in 3 ml of methylene chloride was added dropwise via an addition funnel. After 30 minutes, MS detected (M+H−t-butyl)+=459.10. The mixture was worked up by rinsing with 1N HCl (1×), followed by saturated sodium bicarbonate (1×). The organic layer was dried over sodium sulfate and stripped to give a white glass. The white glass was purified over silica gel in 3:1 to 1:1 hexanes/EtOAc to 100% EtOAc to provide the title compound (180 mg, 0.392 mmol, 73.6% yield) as a white amorphous glass. MS found: (M+H−t-butyl)+=459.13.

Step 4: Example 63

(S)-Phenyl 4-(4-(4-chlorophenyl)-4-hydroxy-3,3-dimethylpiperidin-1-yl)-2-methyl-4-oxobutan-2-ylcarbamate (30 mg, 0.065 mmol), (S)-3-amino-2-methylbutan-2-ol HCl (6.74 mg, 0.065 mmol) and Hunig's base (0.011 mL, 0.065 mmol) were mixed in acetonitrile (3 mL) at RT then microwaved at 150° C. for 30 minutes. MS detected (M+H−t-butyl)+=468.09. Some carbamate was still present, but since some cleavage product was observed, no additional heating was done. The reaction was stripped then purified by preparative HPLC/MS. The MeOH/water mixture was stripped to dryness. Methylene chloride was added and the mixture was dried with sodium sulfate, filtered, and then stripped to give Example 63 (12 mg, 0.026 mmol, 39.2% yield) as a white solid as product. MS found: (M+H)+=468.20. $^1$H NMR (CD3OD, 400 MHz) (NMR shows several rotamers) δ 7.50-7.42 (m, 2H), 7.32-7.27 (m, 2H), 4.62-4.53 (m, 0.5H), 4.18-4.04 (m, 1H), 3.65-3.49 (m, 2.5H), 3.35-3.32 (m, 1H), 3.15-3.02 (m, 1.5H), 2.80-2.52 (m, 1H), 2.46-2.37 (m, 0.5H), 1.54-1.46 (m, 1H), 1.45-1.33 (m, 6H), 1.19-1.14 (m, 6H), 1.14-1.05 (m, 3H), 0.81 (s, 0.5×3H), 0.79 (s, 0.5×3H), 0.77 (s, 0.5×3H), 0.75 (s, 0.5×3H); LCMS method: Inj. Vol.=2000 uL, Start % B=0, Final % B=100, Gradient Time=2 min, Flow Rate=5 ml/min, Wavelength=220, Solvent A=10% MeOH-90% H$_2$O−0.1% TFA, Solvent B=90% MeOH−10% H$_2$O−0.1% TFA, Column 1=Sunfire S5 C18 4.6×30 mm (2 min grad), Retention Time=1.72 minutes.

Examples 64 to 71

Examples 64 to 71, as described in Table 2, were prepared in a similar manner as described for the preparation of Examples 1 to 17 and/or Example 63. The data in the "MS" column represents the values observed for the (M+H)+ ions in MS experiments.

TABLE 2

| Example No. | Structure | Mass Spec (M + H)+ |
|---|---|---|
| 64 | 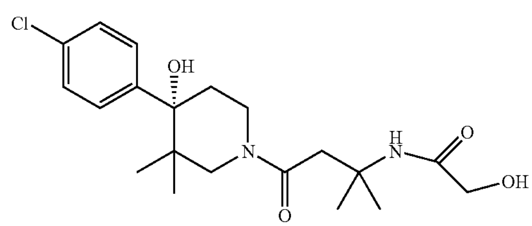 [SMILES: CC(C)(CC(=O)N1CC[C@](O)(c2ccc(Cl)cc2)C(C)(C)C1)NC(=O)CO] | 397 |
| 65 | 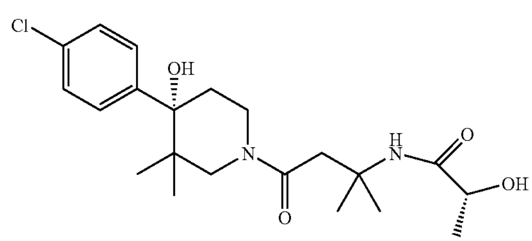 [SMILES: C[C@@H](O)C(=O)NC(C)(C)CC(=O)N1CC[C@](O)(c2ccc(Cl)cc2)C(C)(C)C1] | 411 |
| 66 | 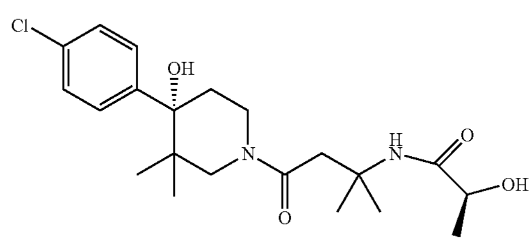 [SMILES: C[C@H](O)C(=O)NC(C)(C)CC(=O)N1CC[C@](O)(c2ccc(Cl)cc2)C(C)(C)C1] | 411 |

TABLE 2-continued

| Example No. | Structure | Mass Spec (M + H)⁺ |
|---|---|---|
| 67 | 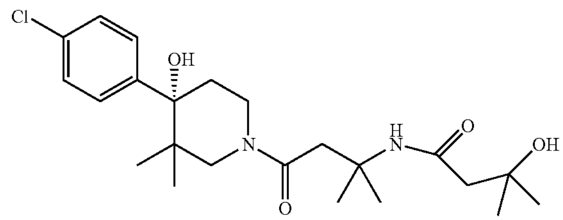 [SMILES: CC(C)(O)CC(=O)NC(C)(C)CC(=O)N1CC[C@](O)(c2ccc(Cl)cc2)C(C)(C)C1] | 439 |
| 68 | 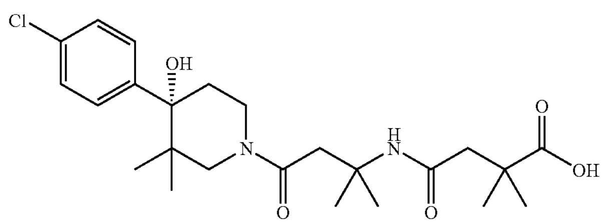 [SMILES: CC(C)(CC(=O)N1CC[C@](O)(c2ccc(Cl)cc2)C(C)(C)C1)NC(=O)CC(C)(C)C(=O)O] | 467 |
| 69 | 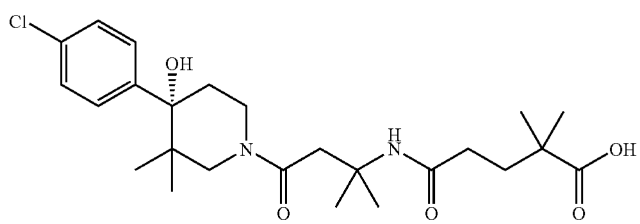 [SMILES: CC(C)(CC(=O)N1CC[C@](O)(c2ccc(Cl)cc2)C(C)(C)C1)NC(=O)CCC(C)(C)C(=O)O] | 481 |
| 70 | 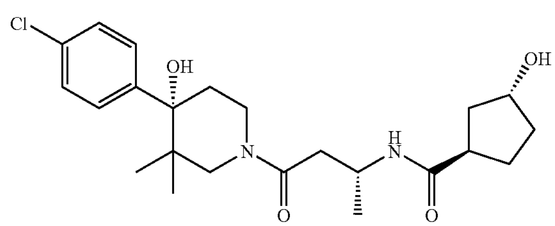 [SMILES: C[C@H](CC(=O)N1CC[C@](O)(c2ccc(Cl)cc2)C(C)(C)C1)NC(=O)[C@@H]1CC[C@@H](O)C1] | 437 |
| 71 | 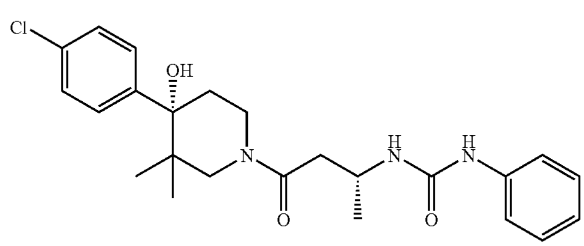 [SMILES: C[C@H](CC(=O)N1CC[C@](O)(c2ccc(Cl)cc2)C(C)(C)C1)NC(=O)Nc1ccccc1] | 444 |

Examples 72a and 72b

N-(4-((S)-4-(4-Chlorophenyl)-4-hydroxy-3,3-dimethylpiperidin-1-yl)-3-methyl-4-oxobutan-2-yl)benzamide (homochiral 72a, 72b)

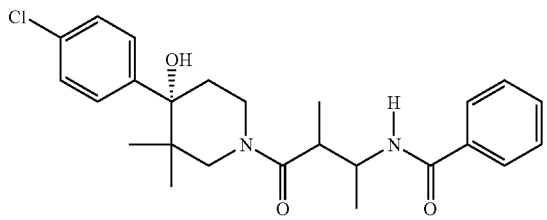 [SMILES: CC(NC(=O)c1ccccc1)C(C)C(=O)N1CC[C@](O)(c2ccc(Cl)cc2)C(C)(C)C1]

Step 1: Preparation of ethyl 3-amino-2-methylbutanoate

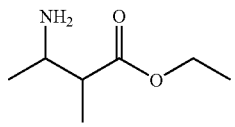

To (Z)-ethyl 3-amino-2-methylbut-2-enoate (*Org. Lett.* 2003, 5(25) 4779-4782, 1.1 g, 7.68 mmol) in acetonitrile (15 mL) was added sodium triacetoxyborohydride (4.88 g, 23.05 mmol) in one lot at RT. After the addition of acetic acid (2.0 mL, 34.9 mmol) (pH of reaction mixture ~6.0), the contents were stirred at RT for 2.5 h. The reaction mixture was concentrated and partitioned between dichloromethane (60 mL) and 20% NaOH (10 mL). The dichloromethane layer is dried over sodium sulfate and concentrated to yield the title compound (1.05 g, 7.23 mmol, 94% yield) as an oil, which was used as such for the subsequent step without further purification. MS found: (M+H)$^+$=146.1.

Step 2: Preparation of ethyl 3-benzamido-2-methylbutanoate

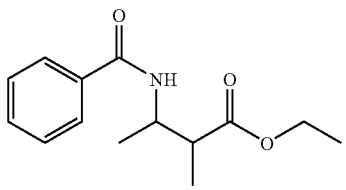 [SMILES: CCOC(=O)C(C)C(C)NC(=O)c1ccccc1]

To ethyl 3-amino-2-methylbutanoate (0.15 g, 1.033 mmol) in dichloromethane (3 mL) was added triethylamine (0.288 mL, 2.066 mmol) followed by the dropwise addition of benzoyl chloride (0.120 mL, 1.033 mmol) at RT. The reaction mixture was stirred at RT for 1 h, partitioned between dichloromethane (20 mL) and 1N HCL (10 mL). The dichloromethane layer was washed with 1N NaOH (10 mL), brine (10 mL), dried over sodium sulfate and concentrated to yield an oil. The oil was subjected to silica gel chromatography using an ISCO setup (12 g silica gel RediSep cartridge, hexane/EtOAc as eluent). The desired fractions are collected and concentrated to yield the title compound (0.066 g, 0.265 mmol, 25.6% yield) as an oil.

Step 3: Preparation of 3-benzamido-2-methylbutanoic acid

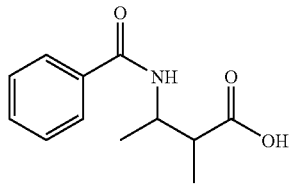 [SMILES: CC(NC(=O)c1ccccc1)C(C)C(=O)O]

To ethyl 3-benzamido-2-methylbutanoate (0.08 g, 0.321 mmol) in MeOH (2 mL) and water (1.000 mL) was added lithium hydroxide (0.015 g, 0.642 mmol) at RT. Contents heated at 60° C. for 1.5 h. The reaction mixture was concentrated and partitioned between dichloromethane (10 mL) and 1N HCl (5 mL). The dichloromethane layer is washed with brine (10 mL), dried overt sodium sulfate and concentrated to yield the title compound (0.055 g, 0.249 mmol, 77% yield) as a foamy solid, which was used as such for the subsequent step without further purification. MS (ESI) m/z 222.16 (M+H)$^+$.

Step 4: Preparation of N-(4-((S)-4-(4-chlorophenyl)-4-hydroxy-3,3-dimethylpiperidin-1-yl)-3-methyl-4-oxobutan-2-yl)benzamide (diastereomeric mixture)

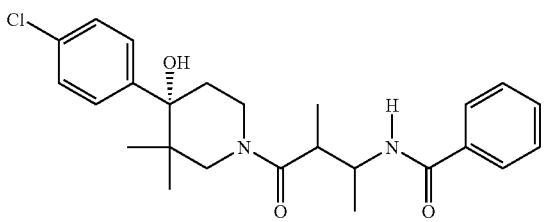 [SMILES: CC(NC(=O)c1ccccc1)C(C)C(=O)N1CC[C@](O)(c2ccc(Cl)cc2)C(C)(C)C1]

To 3-benzamido-2-methylbutanoic acid (0.055 g, 0.249 mmol) in THF (2 mL) are sequentially added (S)-4-(4-chlorophenyl)-3,3-dimethylpiperidin-4-ol (WO 04/043965, 0.060 g, 0.249 mmol), N,N-diisopropylethylamine (0.087 mL, 0.497 mmol) and BOP (0.110 g, 0.249 mmol) at RT. The reaction mixture was stirred at RT for 70 h, and concentrated. The oily residue was dissolved in MeOH (2.0 mL) and subjected to preparative HPLC (Phenomex S10 30×100 mm; 10 min. gradient; solvent A=10% MeOH, 90% H$_2$O, 0.1% TFA, solvent B=90% MeOH, 10% H$_2$O, 0.1% TFA). Two fractions (diastereomer A and B) are collected and individually processed by concentrating and partitioning between dichloromethane (10 mL) and sat. aq. NaHCO$_3$ (10 mL). The dichloromethane layer was dried over sodium sulfate and concentrated to yield: Diastereomer A: (0.042 g, 0.089 mmol, 35.9% yield) as a foamy solid. Retention time=3.23 min (YMC S5 Combi ODS 4.6×50 mm; 4 min. gradient; solvent A=10% MeOH, 90% H$_2$O, 0.2% H$_3$PO$_4$, solvent B=90% MeOH, 10% H$_2$O, 0.2% H$_3$PO$_4$. MS (ESI) m/z 443.11 (M+H)$^+$; and Diastereomer B: (0.03 g, 0.064 mmol, 25.9% yield) as a foamy solid. Retention time=3.42 min (YMC S5 Combi ODS 4.6×50 mm; 4 min. gradient; solvent A=10%

MeOH, 90% H₂O, 0.2% H₃PO₄, solvent B=90% MeOH, 10% H₂O, 0.2% H₃PO₄. MS (ESI) m/z 443.12 (M+H)⁺.

Step 5: Examples 72a and 72b

Diastereomer A (30 mg) from step D above was subjected to preparative chiral HPLC employing a Chiracel OJ-H column and using CO₂/MeOH as eluent. Two fractions were isolated and individually processed by concentrating under reduced pressure to give: Example 72a: 0.010 g, white solid. ee>99%. Retention time=3.28 min (YMC S5 Combi ODS 4.6×50 mm; 4 min. gradient; solvent A=10% MeOH, 90% H₂O, 0.2% H₃PO₄, solvent B=90% MeOH, 10% H₂O, 0.2% H₃PO₄. MS (ESI) m/z 443.18 (M+H)⁺; ¹H NMR (600 MHz, DMSO, ~1:1 mixture of rotamers) δ ppm 8.20 (1 H, ddd, J=14.37, 8.75, 5.60.5 Hz), 7.89 (1 H, dd, J=8.42, 2.15 Hz), 7.85 (1 H, dd, J=6.61, 1.65 Hz), 7.53 (1 H, q, J=7.49 Hz), 7.48 (3 H, dd, J=7.93, 4.61 Hz), 7.39-7.44 (1 H, m), 7.36 (2 H, d, J=8.23 Hz), 5.12 (0.5 H, s), 5.09 (0.5 H, d, J=1.31 Hz), 4.53 (0.5 H, d, J=12.21 Hz), 4.21-4.32 (0.5 H, m), 4.10-4.20 (0.5 H, m), 4.02 (0.5 H, d, J=12.55 Hz), 3.90 (0.5 H, d, J=11.53 Hz), 3.49-3.52 (0.5 H, m), 3.47 (1 H, br. s.), 3.18 (1 H, t, J=9.25 Hz), 2.97 (0.5 H, tt, J=12.92, 3.23 Hz), 2.92 (0.5 H, d, J=11.53 Hz), 2.51 (1 H, qd, J=13.43, 13.20.5 Hz), 1.47 (1 H, td, J=13.29, 1.81 Hz), 1.20 (1.5 H, dd, J=6.61, 3.30 Hz), 1.07 (1.5 H, dd, J=6.61, 2.30.5 Hz), 1.03 (3 H, dd, J=5.28, 1.65 Hz), 0.72 (1.5 H, s), 0.70 (3 H, s), 0.63 (1.5 H, s); and Example 72b: 0.011 g, white solid. ee>99%. Retention time=3.27 min (YMC S5 Combi ODS 4.6×50 mm; 4 min. gradient; solvent A=10% MeOH, 90% H₂O, 0.2% H₃PO₄, solvent B=90% MeOH, 10% H₂O, 0.2% H₃PO₄. MS (ESI) m/z 443.18 (M+H)⁺; ¹H NMR (400 MHz, CHLOROFORM-d, ~1:1 mixture of rotamers) δ ppm 7.74 (2 H, dd, J=6.90, 1.38 Hz), 7.46-7.54 (1 H, m), 7.39-7.46 (2 H, m), 7.33-7.39 (2 H, m), 7.27-7.33 (2 H, m), 6.64 (0.5 H, d, J=8.01.5 Hz), 6.55 (0.5 H, d, J=7.78 Hz), 4.65 (0.5 H, ddd, J=12.99, 2.51, 2.31 Hz), 4.24-4.43 (1 H, m), 4.18 (0.5 H, dd, J=12.92, 1.61.5 Hz), 3.90 (0.5 H, ddd, J=13.55, 2.51, 2.00.5 Hz), 3.56-3.62 (0.5 H, m), 3.55 (0.5 H, d, J=13.30 Hz), 3.32-3.40 (0.5 H, m), 3.29 (0.5 H, dd, J=13.30, 1.25 Hz), 3.21 (0.5 H, quin, J=7.01.5 Hz), 3.05 (0.5 H, td, J=13.05, 3.00.5 Hz), 2.97 (0.5 H, d, J=12.80 Hz), 2.64 (0.5 H, td, J=13.49, 4.89 Hz), 2.49 (0.5 H, td, J=13.55, 5.01 Hz), 1.59-1.74 (1 H, m), 1.46 (1.5 H, d, J=6.78 Hz), 1.41 (1.5 H, d, J=6.78 Hz), 1.29 (1.5 H, d, J=7.01.5 Hz), 1.19 (1.5 H, d, J=7.28 Hz), 0.81 (3 H, s), 0.75 (1.5 H, s), 0.68 (1.5 H, s).

Example 73

N-(4-(4-(3,4-Chlorophenyl)-4-hydroxy-3,3-dimethylpiperidin-1-yl)-2-methyl-4-oxobtutan-2-yl)benzamide

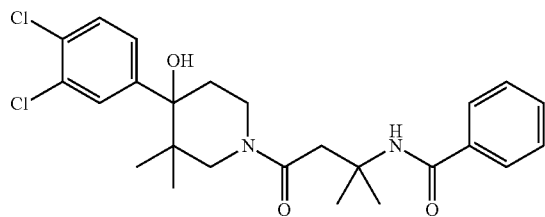 [SMILES: CC(C)(CC(=O)N1CCC(O)(c2ccc(Cl)c(Cl)c2)C(C)(C)C1)NC(=O)c1ccccc1]

Step 1: N-(4-(3,3-Dimethyl-4-oxopiperidin-1-yl)-2-methyl-4-oxobtutan-2-yl)benzamide

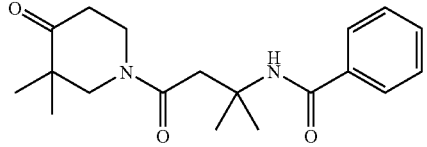 [SMILES: CC(C)(CC(=O)N1CCC(=O)C(C)(C)C1)NC(=O)c1ccccc1]

3,3-Dimethyl-4-oxopiperidium chloride (0.53 g, 3.26 mmol), 3-benzamido-3-methylbutanoic acid (0.66 g, 2.96 mmol), 1H-benzo[d]-[1,2,3]triazol-1-ol (0.48 g, 3.56 mmol), N1-((ethylimino)methylene)-N3,N3-dimethylpropane-1,3-diamine hydrochloride (1.25 g, 6.52 mmol) and N-ethyl-N-isopropyl-2-amine (1.53 g, 11.86 mmol) was stirred in DMF (2 ml) overnight at rt. The DMF was removed by evaporation and the residue was partitioned between DCM (50 ml) and sat'd brine (2×50 ml), dried over sodium sulfate, filtered, evaporated to yield a yellowish resin. Flash chromatography (silica gel, 2:1 ETOAc:heptane) yielded the title compound as a yellow resin (0.82 g, 84% yield). ¹H NMR (400 MHZ, CDCl₃) δ 7.41-7.52 (m, 5 H), 7.68-7.80 (m, 4 H), 3.79-3.99 (2 t, J=4 Hz, 2 H), 3.66 (s,1 H), 3.56 (s, 1 H), 2.95 (s, 1 H), 2.89 (s, 1 H), 2.52-2.60 (2 t, J=8 Hz, 2 H), 1.65 (s,3 H), 1.63 (s, 3 H), 1.16 (s,3 H), 1.08 (s, 3 H); M+H=331.35. LCMS Method; HPLC Method: Inj. Vol.=10 uL, Flow Rate=4 ml/min; Wavelength 1=220, Solvent A=0.1% TFA in H₂O:MeOH (90:10)), Solvent B=0.1% TFA in H₂O:MeOH (10:90) Start=0% solvent B, finish=100% solvent B; Col-YMC ODS-A S5 4.6×33 mm (4 min gradient); Retention time=2.190; HPLC Method: Inj. Vol.=5 uL, Start % B=10, 12 Min. 100%, 15 Min. 100%, Flow Rate=1 ml/min; Wavelength 1=220, Wavelength 2=254, Solvent A=0.05% TFA in H₂O:MeCN (95:5), Solvent B=0.05% TFA in H₂O:MeCN (5:95), Col-1: Sunfire C18 3.5 um, 4.6×150 mm; Retention Time=7.88 min., Col-2: Xbridge Phenyl 3.5 um, 4.6×150 mm; Retention Time=7.21 min.

Step 2: Example 73

N-(4-(3,3-dimethyl-4-oxopiperidin-1-yl)-2-methyl-4-oxobtan-2-yl)benzamide (45.3 mg, 0.137 mmol), 4-bromo-1,2-dichlorobenzene (71.2 mg, 0.315 mmol) and dry THF (3 mL) was cooled to −78° C. and n-butyllithium (2 M in THF, 0.22 mL, 0.439 mmol) was added. The reaction was stirred 6 hrs at −78° C., and then sat'd ammonium chloride (5 mL) was added. Upon completion of addition, the reaction was allowed to come to rt overnight. Ethylacetate (20 mL) then water (20 mL) was added, the layers were separated, and the organics were dried over sodium sulfate, filtered, and evaporated. The desired product was isolated using Preparative HPLC, redissolved into DCM (5 mL) and passed through a filter plug of basic alumina powder, then evaporated to yield Example 73 as a white solid (19.4 mg, 30% yield). ¹H NMR (rotamers) (400 mHz, CDCl₃).8.23 (s, 0.5 H), 7.87 (s, 0.5 H), 7.79-7.83 (m, 2 H), 7.55 (d, J=4 Hz, 0.5 H), 7.51 (d, J=4 Hz, 0.5 H), 7.36-7.47 (m, 4 H), 7.16-7.25 (4 d, J=4 Hz, 1 H), 4.69-4.75 (2 m, 0.5 H), 4.23 (dm, J=4 Hz, 0.5 H), 4.08 (t, J=4 Hz, 1 H), 3.59-3.65 (m, 1 H), 3.37-3.42 (dm, J=20 Hz, 0.5 H), 2.92-3.12 (m, 1 H), 2.78-2.83 (m, 1 H), 2.53-2.70 (m, 2 H), 1.89 (d, J=20 Hz, 1 H), 1.65, 1.63, 1.56 (3 s, 6 H), 0.89, 0.83, 0.72 (3 s, 6 H), M+H=477.31, LCMS Method; HPLC Method: Inj. Vol.=10 ul Flow Rate=4 ml/min, Wavelength 1=220, Solvent A=0.1% TFA in H₂O:MeOH (90:10)), Solvent B=0.1% TFA in H₂O:MeOH (10:90) Start:=0%, finish=100% solvent B; Col-YMC ODS-A S5 4.6×33 mm (4 min gradient) retention time=3.51 min; HPLC Method: Inj. Vol.=5 uL, Start %B=10, 12 Min. 100%, 15 Min. 100%, Flow Rate=1 ml/min; Wavelength 1=220, Wavelength 2=254, Solvent A=0.05% TFA in H₂O:MeCN (95:5), Solvent B=0.05% TFA in H₂O:MeCN (5:95), Col-1: Sunfire C18 3.5 um, 4.6×150 mm; Retention Time=11.77 min, Col-2: Xbridge Phenyl 3.5 um, 4.6×150 mm; Retention Time=10.26 min.

Examples 74 to 86

Examples 74 to 86, as described in Table 3, were prepared in a similar manner as described for the preparation of Example 73. The data in the "MS" column represents the values observed for the (M+H)$^+$ ions in MS experiments.

TABLE 3

| Example No. | Structure | Mass Spec (M + H)$^+$ |
|---|---|---|
| 74 | 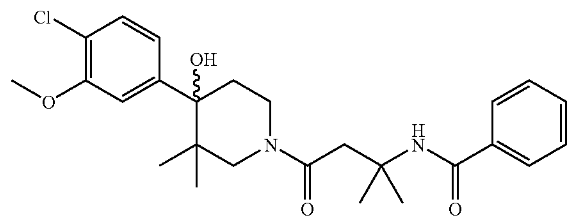 [SMILES: COc1cc(C2(O)CCN(C(=O)CC(C)(C)NC(=O)c3ccccc3)CC2(C)C)ccc1Cl] | 473.31 |
| 75 | 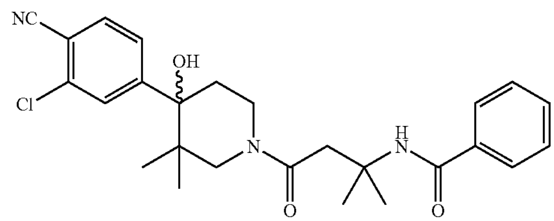 | 468.37 |
| 76 | 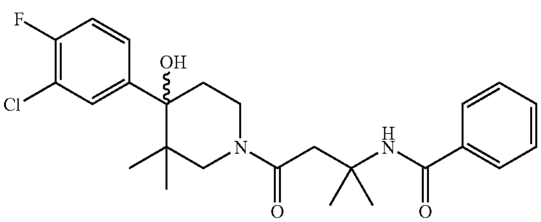 [SMILES: CC(C)(CC(=O)N1CCC(O)(c2ccc(F)c(Cl)c2)C(C)(C)C1)NC(=O)c1ccccc1] | 461.33 |
| 77 | 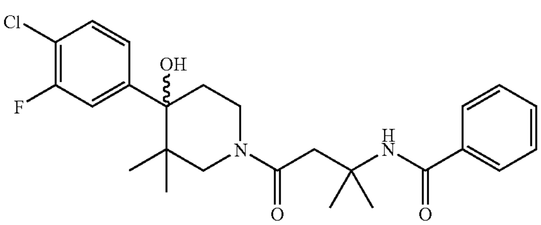 | 461.27 |
| 78 | 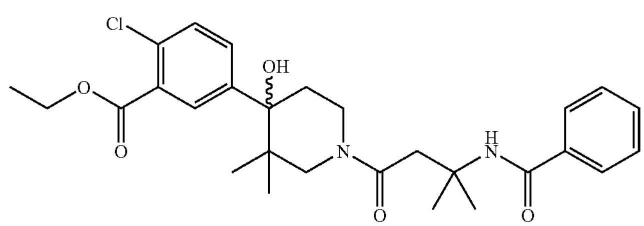 [SMILES: CCOC(=O)c1cc(C2(O)CCN(C(=O)CC(C)(C)NC(=O)c3ccccc3)CC2(C)C)ccc1Cl] | 515.44 |
| 79 | 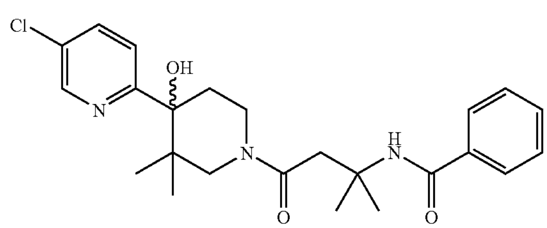 [SMILES: CC(C)(CC(=O)N1CCC(O)(c2ccc(Cl)cn2)C(C)(C)C1)NC(=O)c1ccccc1] | 444.33 |

TABLE 3-continued

| Example No. | Structure | Mass Spec (M + H)+ |
|---|---|---|
| 80 | 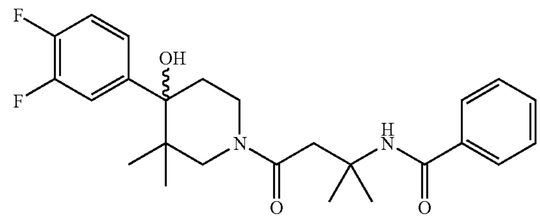 [SMILES: CC(C)(CC(=O)N1CCC(O)(c2ccc(F)c(F)c2)C(C)(C)C1)NC(=O)c1ccccc1] | 445.34 |
| 81 | 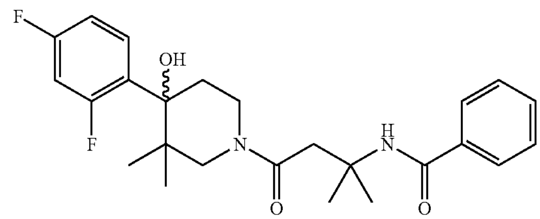 [SMILES: CC(C)(CC(=O)N1CCC(O)(c2ccc(F)cc2F)C(C)(C)C1)NC(=O)c1ccccc1] | 445.36 |
| 82 | 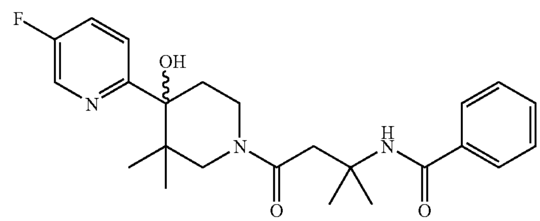 | 428.36 |
| 83 | 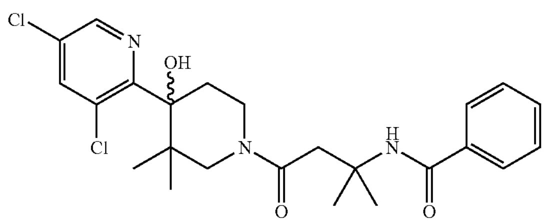 [SMILES: CC(C)(CC(=O)N1CCC(O)(c2ncc(Cl)cc2Cl)C(C)(C)C1)NC(=O)c1ccccc1] | 478.27 |
| 84 | 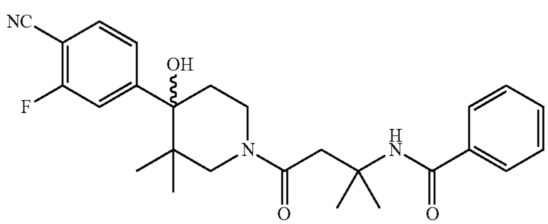 [SMILES: CC(C)(CC(=O)N1CCC(O)(c2ccc(C#N)c(F)c2)C(C)(C)C1)NC(=O)c1ccccc1] | 452.33 |
| 85 | 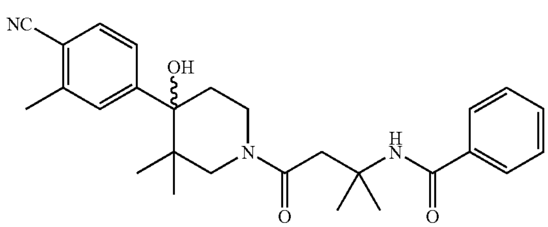 | 448.33 |
| 86 | 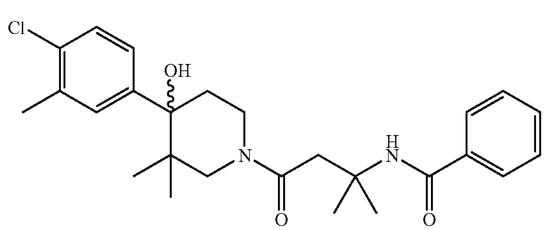 [SMILES: Cc1cc(C2(O)CCN(C(=O)CC(C)(C)NC(=O)c3ccccc3)CC2(C)C)ccc1Cl] | 457.37 |

Example 87

N-((S)-2-((S)-4-(4-Chlorophenyl)-4-hydroxy-3,3-dimethylpiperidine-1-carbonyl)-3-methylbutyl)benzamide

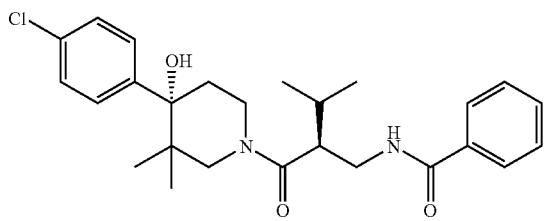 [SMILES: CC(C)[C@@H](CNC(=O)c1ccccc1)C(=O)N1CC[C@](O)(c2ccc(Cl)cc2)C(C)(C)C1]

Step 1: Preparation of (S)-methyl 3-methyl-2-(((2-(trimethylsilyl)ethoxy)carbonylamino)methyl)butanoate

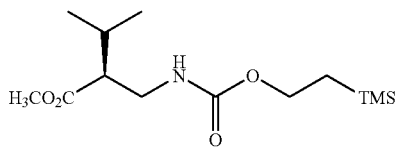 [SMILES: COC(=O)[C@H](CNC(=O)OCC[Si](C)(C)C)C(C)C]

A dry 250 ml 3-neck flask, equipped with a reflux condenser and a thermometer, was charged with (R)-3-(methoxycarbonyl)-4-methylpentanoic acid (1.6 g, 9.19 mmol, which was prepared according to the procedure described in Robert J. Cregge et al., *J. Med. Chem.* 1998, 41, 2461-2480) and anhydrous acetonitrile (60 mL) under Argon. To the mixture was added N-methylmorpholine (2.020 mL, 18.37 mmol) followed by diphenylphosphoryl azide (1.979 mL, 9.19 mmol), and the mixture was stirred at rt for 1.5 hrs. After this time, 2-(trimethylsilyl)ethanol (6.58 mL, 45.9 mmol) was added to the mixture and the mixture was heated at 85° C. with stirring for 1 hr and 40 minutes. After cooling to rt, the solvent was evaporated off and the resulting residue was dissolved in EtOAc (~100 ml). The resulting solution was washed with water, sat'd NaHCO$_3$ (2×), 1N HCl and brine; dried over Na$_2$SO$_4$ and evaporated to give an oily residue. The oily residue was purified by Combiflash chromatography (220 g silica gel) eluting with 2:8 EtOAc-hexane to give 1.22 g of title compound. $^1$H NMR (CDCl$_3$, 400 MHz) δ ppm 4.95 (1 H, br. s.), 4.03-4.22 (2 H, m), 3.70 (3 H, s), 3.40-3.54 (1 H, m), 3.23-3.34 (1 H, m), 2.38-2.53 (1 H, m), 1.97 (1 H, dq, J=13.62, 6.81 Hz), 1.26 (6 H, t, J=7.14 Hz), 0.97 (3 H, d, J=7.03 Hz), 0.94 (3 H, d, J=6.81 Hz), 0.00 (9 H, s).

Step 2: Preparation of (S)-3-methyl-2-(((2-(trimethylsilyl)ethoxy)carbonylamino)methyl)butanoic acid

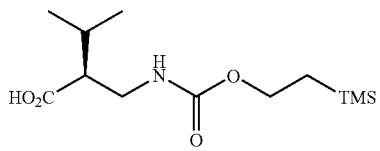 [SMILES: CC(C)[C@@H](CNC(=O)OCC[Si](C)(C)C)C(=O)O]

To a solution of (S)-methyl 3-methyl-2-(((2-(trimethylsilyl)ethoxy)carbonylamino)methyl)butanoate (459 mg, 1.586 mmol) in THF (4 mL) was added 2 M LiOH (4.0 mL, 8.00 mmol). Upon completion of addition, the mixture was stirred at rt for 20 hrs. After this time, the reaction mixture was quenched with sat'd NH$_4$Cl (about 4 ml) and then 1 N HCl (8 ml) was added. The crude product was extracted with EtOAc and the extract was washed with brine. The combined aqueous layers were back extracted with EtOAc. The EtOAc extracts were combined, dried over Na$_2$SO$_4$ and evaporated to give the title compound as an oily residue, which was used in the next step without further purification.

Step 3: Preparation of 2-(trimethylsilyl)ethyl(S)-2-((S)-4-(4-chlorophenyl)-4-hydroxy-3,3-dimethylpiperidine-1-carbonyl)-3-methylbutylcarbamate

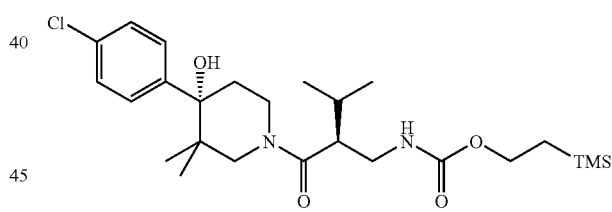

To a solution of (S)-4-(4-chlorophenyl)-3,3-dimethylpiperidin-4-ol (91 mg, 0.38 mmol), (S)-3-methyl-2-(((2-(trimethylsilyl)ethoxy)carbonylamino)methyl)butanoic acid (105 mg, 0.380 mmol), EDC (146 mg, 0.760 mmol) and HOBT (11.64 mg, 0.076 mmol) in CH$_2$Cl$_2$ (2 mL) was added Hunig's Base (0.199 mL, 1.140 mmol). Upon completion of addition, the reaction mixture was stirred at room temperature for 16 hrs. After this time, the reaction mixture was quenched with sat'd NaHCO$_3$ and the crude product was extracted with EtOAc and the extract was washed with brine. The combined aqueous layers were back extracted with EtOAc. The EtOAc extracts were combined, dried over Na$_2$SO$_4$ and evaporated to give a solid residue. The solid residue was purified by Combiflash chromatography (40 g silica gel) eluting with 1:1 and 8:2 EtOAc-hexane to give 110.5 mg of the title compound as a white foamy solid. MS (ESI$^+$)=497.15 (M+H)$^+$

Step 4: Preparation of (S)-2-(aminomethyl)-1-((S)-4-(4-chlorophenyl)-4-hydroxy-3,3-dimethylpiperidin-1-yl)-3-methylbutan-1-one

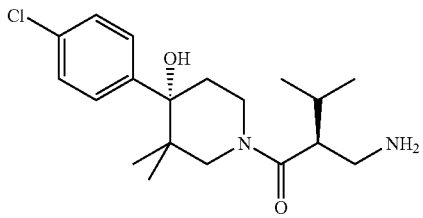 [SMILES: CC(C)[C@@H](CN)C(=O)N1CC[C@](O)(c2ccc(Cl)cc2)C(C)(C)C1]

To a solution of 2-(trimethylsilyl)ethyl(S)-2-((S)-4-(4-chlorophenyl)-4-hydroxy-3,3-dimethylpiperidine-1-carbonyl)-3-methylbutylcarbamate (110 mg, 0.221 mmol) in THF (1 mL) was added 1 equivalent of 1 M-tetra-N-butylammonium fluoride (0.221 mL, 0.221 mmol). The resulting mixture was stirred at room temperature for 1.5 hrs. After this time, the reaction was analyzed by LC/MS, which showed that the reaction was very slow. An additional 4 equiv. of TBAF (0.88 ml) was added and the mixture was stirred at room temperature for an additional 24 hour. After this time, the reaction mixture was added to EtOAc, washed with water and brine, dried over Na$_2$SO$_4$ and evaporated to give an oily residue. The oily residue was purified by Combiflash chromatography (24 g silica gel) with elution by 6:4 EtOAc-hexane to give the title compound (85.3 mg). MS (ESI$^+$)=353.13 (M+H)$^+$

Step 5: Example 87

To a solution of (S)-2-(aminomethyl)-1-((S)-4-(4-chlorophenyl)-4-hydroxy-3,3-dimethylpiperidin-1-yl)-3-methylbutan-1-one (0.036 g, 0.102 mmol) in acetonitrile (1 mL) was added benzoic acid (0.012 g, 0.102 mmol), o-benzotriazol-1-yl-N,N,N',N'-tetramethyluronium tetrafluoroborate (0.039 g, 0.122 mmol) and Hunig's Base (0.036 mL, 0.204 mmol). Upon completion of addition, the reaction mixture was stirred at room temperature overnight. After this time, the reaction mixture was purified by prep HPLC to give Example 87 (18.9 mg). MS (ESI$^+$)=457.14 (M+H)$^+$. $^1$H NMR (CDCl$_3$, 400 MHz) (NMR shows several rotamers) δ ppm 7.77 (1 H, s), 7.76 (1 H, s), 7.52 (0.5 H, s), 7.51 (0.5 H, s), 7.44 (2 H, t, J=7.47 Hz), 7.29-7.39 (2 H, m), 7.25 (1 H, br. s), 7.24 (1 H, br. s), 4.68-4.76 (0.53 H, m), 4.22 (0.37 H, d, J=11.42 Hz), 4.01 (0.35 H, d, J=13.18 Hz), 3.67-3.81 (1.49 H, m), 3.57 (1 H, d, J=13.18 Hz), 3.47-3.53 (0.31 H, m), 3.41 (0.59 H, d, J=13.18 Hz), 3.00-3.22 (2.18 H, m), 2.86 (0.40 H, d, J=4.83 Hz), 2.64 (0.30 H, td, J=13.84, 4.39 Hz), 2.50 (0.46 H, td, J=13.84, 4.83 Hz), 2.06-2.16 (0.31 H, m), 1.95-2.05 (0.52 H, m), 1.35-1.56 (1 H, m), 1.26 (0.34 H, s), 1.1 (1.37 H, d, J=7.03 Hz), 1.09 (1.49 H, d, J=7.03 Hz), 1.04 (1.90 H, d, J=7.03 Hz), 1.01 (1.84 H, d, J=7.03 Hz), 0.85 (1.45 H, s), 0.82 (1.85 H, s), 0.79 (1.35 H, s), 0.58 (1.72 H, s); HPLC Method: Inj. Vol.=5 uL, Start % B=10, 12 Min. 100%, 15 Min. 100%, Flow Rate=2 mL/min (1 mL/min on each column), Wavelength 1=220, Wavelength 2=254, Solvent Pair=TFA–ACN/H$_2$O, Solvent A=0.05% TFA in H$_2$O:MeCN (95:5), Solvent B=0.05% TFA in H$_2$O: MeCN (5:95), Col-1: Sunfire C18 3.5 um, 4.6×150 mm; Retention Time=10.67 minutes, Col-2: Xbridge Phenyl 3.5 um, 4.6×150 mm; Retention Time=9.23 minutes.

Examples 88 to 92

Examples 88 to 92, as described in Table 4, were prepared in a similar manner as described for the preparation of Example 87. The data in the "MS" column represents the values observed for the (M+H)$^+$ ions in MS experiments.

TABLE 4

| Example No. | Structure | Mass Spec (M + H)$^+$ |
|---|---|---|
| 88 | ![structure] | 449.2 |
| 89 | ![structure] | 471.2 |

TABLE 4-continued

| Example No. | Structure | Mass Spec (M + H)+ |
|---|---|---|
| 90 | ![structure 90] | 463.2 |
| 91 | ![structure 91] | 449.1 |
| 92 | ![structure 92] | 463.2 |

Example 93

N-(4-((±)-(trans)-4-(4-Chlorophenyl)-3,4-dihydroxy-3-methylpiperidin-1-yl)-2-methyl-4-oxobutan-2-yl)cyclopentanecarboxamide

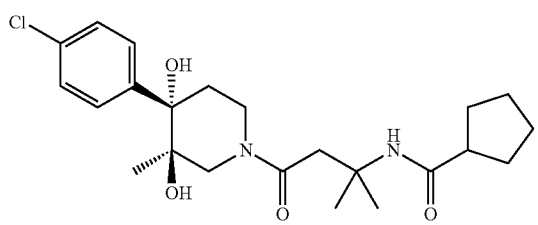 [SMILES: CC(C)(CC(=O)N1CC[C@](O)(c2ccc(Cl)cc2)[C@](C)(O)C1)NC(=O)C1CCCC1]

Step 1: tert-Butyl 3-methyl-4-oxopiperidine-1-carboxylate

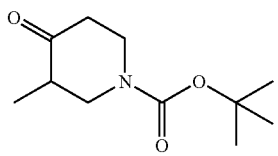

A mixture of 1-benzyl-3-methylpiperidin-4-one (5.25 g, 25.8 mmol), BOC-anhydride (6.60 mL, 28.4 mmol), and 10% palladium on carbon (0.275 g, 2.58 mmol) in ethanol (100 mL) was degassed under vacuum and nitrogen, then hydrogenated at 50 psi for 4 hours. The catalyst was removed by filtration, rinsed with methanol, and the combined filtrate and rinsings were concentrated in vacuo. The residue was purified over a 330 g silica gel column, eluting at 100 mL/min with a 10% to 30% ethyl acetate/hexanes gradient followed by 30% ethyl acetate/hexanes to yield the title compound (5.07 g, 23.77 mmol, 92% yield) as a colorless oil, which solidified upon standing. MS (ESI+)=158.1 (M−tert-Bu)+.

Step 2: tert-Butyl 4-(4-chlorophenyl)-4-hydroxy-3-methylpiperidine-1-carboxylate

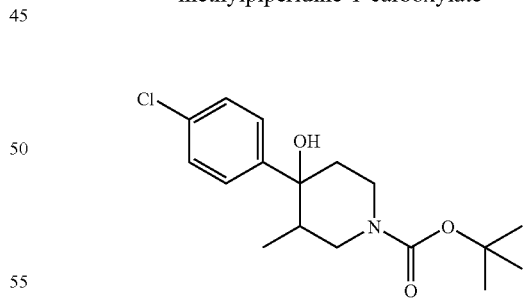

A solution of 1-bromo-4-chlorobenzene (9.24 g, 48.2 mmol) in anhydrous THF (100 mL) was cooled to −78° C. and treated dropwise with 1.6 M n-butyllithium in hexanes (28.7 mL, 46.0 mmol). The mixture was stirred at −78° C. for 45 minutes, during which time a precipitate was observed, then the slurry was treated dropwise with a solution of tert-butyl 3-methyl-4-oxopiperidine-1-carboxylate (4.9 g, 22.98 mmol) in anhydrous THF (50 mL). The reaction was stirred at −78° C. for 2 hours, then allowed to slowly warm to −20° C. and quenched with saturated ammonium chloride. The layers were separated, and the organic phase was concentrated in vacuo. The aqueous phase was extracted once with ethyl acetate (300 mL), and the organic phase was combined with the residue from the original organic phase. The mixture was washed 3× with water, and once with brine, then dried over sodium sulfate and concentrated in vacuo. The residue was digested in boiling hexanes (100 mL) for 1 hour, then the mixture was cooled to room temperature. The solids were collected by filtration, rinsed with a small amount of hot hexanes, and dried under vacuum to yield the title compound (6.25 g, 19.18 mmol, 83% yield) as a white powder. MS (ESI$^+$)=252.2 (M–tert-BuO)$^+$.

Step 3: tert-Butyl 4-(4-chlorophenyl)-3-methyl-5,6-dihydropyridine-1(2H)-carboxylate

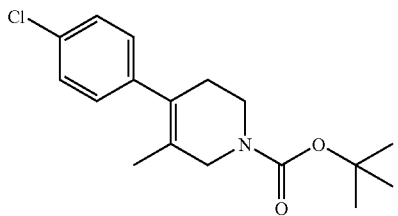 [SMILES: CC1=C(c2ccc(Cl)cc2)CCN(C(=O)OC(C)(C)C)C1]

A suspension of tert-butyl 4-(4-chlorophenyl)-4-hydroxy-3-methylpiperidine-1-carboxylate (5.5 g, 16.88 mmol) in concentrated HCl (15 mL, 180 mmol) was stirred until a homogeneous solution was observed. The reaction was then heated to reflux and stirred overnight. The mixture was cooled to 0° C. and treated with the careful, portion-wise addition of solid sodium hydroxide until a pH of ~13 was achieved. The biphasic mixture was extracted 5× with ethyl acetate, and the combined organic phases were washed with a small amount of brine, dried over sodium sulfate, and concentrated in-vacuo to 3.3 g of a colorless oil. The oil was dissolved in THF (50 mL), and the resulting solution was treated with BOC-anhydride (4.67 mL, 20.13 mmol). The reaction was stirred for two days at room temperature. After this time, the mixture was concentrated in vacuo, and the resulting residue was purified over a 330 g silica gel column, eluting at 100 mL/min with a 0% to 15% ethyl acetate/hexanes gradient followed by 15% ethyl acetate/hexanes to yield the title compound (4.93 g, 16.02 mmol, 88% yield) as a colorless solid. The product isolated contained 15% of tert-butyl 4-(4-chlorophenyl)-5-methyl-5,6-dihydropyridine-1(2H)-carboxylate, resulting from a byproduct in the previous step. The material was used as-is. MS (ESI$^+$)=252.2 (M+tert-Bu)$^+$.

Step 4: tert-Butyl 6-(4-chlorophenyl)-1-methyl-7-oxa-3-azabicyclo[4.1.0]heptane-3-carboxylate

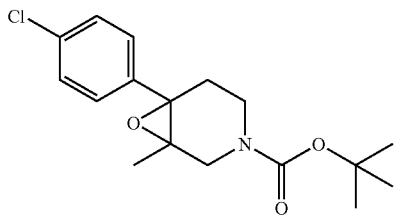 [SMILES: CC(C)(C)OC(=O)N1CCC2(c3ccc(Cl)cc3)OC2(C)C1]

A solution of tert-butyl 4-(4-chlorophenyl)-3-methyl-5,6-dihydropyridine-1(2H)-carboxylate (1.09 g, 3.54 mmol) in methylene chloride (15 mL) was cooled to 0° C. and treated dropwise with a solution of m-CPBA (1.111 g, 4.96 mmol) in methylene chloride (15 mL). The reaction was stirred at 0° C. for 1 hour, then allowed to slowly warm to room temperature and stirred overnight. The mixture was cooled to 0° C., treated with saturated aqueous sodium sulfite (20 mL), and stirred for 1 hour. The layers were separated, and the organic phase was washed once with water, 3× with saturated sodium carbonate, once with water, and once with brine, dried over sodium sulfate, and concentrated in vacuo. The residue was purified over a 120 g silica gel column, eluting at 85 mL/min with a 0% to 17% ethyl acetate/hexanes gradient followed by 17% ethyl acetate/hexanes to yield the title compound as a colorless oil. MS (ESI$^+$)=268.2 (M–tert-Bu)$^+$, 250.1 (M–tert-BuO)$^+$.

Step 5: (±)-(trans)-4-(4-Chlorophenyl)-3-methylpiperidine-3,4-diol

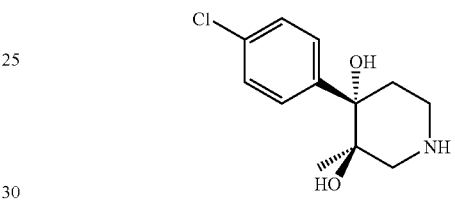

A solution of tert-butyl 6-(4-chlorophenyl)-1-methyl-7-oxa-3-azabicyclo[4.1.0]heptane-3-carboxylate (120 mg, 0.371 mmol) in 2:1 water/dioxane (3 mL) was treated with sulfuric acid (0.049 mL, 0.926 mmol), and the mixture was refluxed for 6 hours. The mixture was cooled to 0° C. and treated carefully with solid sodium hydroxide until a pH of ~13 was achieved. The mixture was extracted 4× with ethyl acetate, and the combined organic phases were washed with a small amount of brine, dried over sodium sulfate, and concentrated in-vacuo to yield the title compound (83 mg, 0.343 mmol, 93% yield) as a colorless glass. MS (ESI$^+$)=242.2 (M+H)$^+$.

Step 6: Example 93

A mixture of (±)-(trans)-4-(4-chlorophenyl)-3-methylpiperidine-3,4-diol (40 mg, 0.165 mmol), 3-(cyclopentanecarboxamido)-3-methylbutanoic acid (35.3 mg, 0.165 mmol), and triethylamine (0.081 mL, 0.579 mmol) in DMF (1 mL) was treated with BOP (73.2 mg, 0.165 mmol), and the mixture was stirred overnight at room temperature. The solvent was evaporated with a stream of nitrogen, and the residue was taken up in ethyl acetate. The mixture was washed 3× with saturated sodium carbonate, and 3× with 1 N HCl, then the organic phase was concentrated in vacuo. The residue was purified via prep HPLC using the following conditions: A=H$_2$O+0.05% TFA, B=acetonitrile+0.05% TFA; Column: Phenomenex Luna 5µ C18(2) 250×21.2 mm, Flow: 15 mL/min, Gradient: 0% B over 5 min, 0-100% B over 30 min, 100% B for 5 min. Fractions containing the desired product were combined and freeze-dried to yield a colorless powder which appeared to be impure by NMR. The powder was purified over a 12 g silica gel column, eluting at 30 mL/min with a 0-5% methanol/methylene chloride gradient to yield Example 93 (27 mg, 0.062 mmol, 37.3% yield) as a colorless glass. MS (ESI$^+$)=437.3 (M+H)$^+$. $^1$H NMR (CD$_3$OD, 500

MHz) (NMR shows several rotamers) δ ppm 7.58-7.52 (m, 2 H), 7.28 (d, J=8.5 Hz, 2 H), 4.49 (ddd, J=12.8, 4.6, 2.3 Hz, 0.6 H), 4.29 (d, J=13.3 Hz, 0.4 H), 4.03 (ddd, J=13.5, 4.6, 2.1 Hz, 0.4 H), 3.68 (d, J=13.3 Hz, 0.6 H), 3.59-3.54 (m, 0.6 H), 3.54-3.48 (m, 0.4 H), 3.10 (d, J=13.3 Hz, 0.6 H), 3.06-3.02 (m, 0.6 H), 2.98 (d, J=14.2 Hz, 0.4 H), 2.83 (d, J=14.2 Hz, 0.4 H), 2.75-2.67 (m, 0.4 H), 2.64-2.54 (m, 1.8 H), 2.45 (d, J=14.2 Hz, 0.6 H), 1.88-1.77 (m, 2.2 H), 1.75-1.62 (m, 4.6 H), 1.63-1.52 (m, 2.4 H), 1.48-1.38 (m, 7.4 H), 0.93 (s, 3 H); HPLC Method: Inj. Vol.=5 uL, Start % B=10, 12 Min. 100%, 15 Min. 100%, Flow Rate=2 mL/min (1 mL/min on each column), Wavelength 1=220, Wavelength 2=254, Solvent Pair=TFA–ACN/H$_2$O, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=8.57 minutes, Col-2: Xbridge Phenyl 3.5 um, 4.6×150 mm;etention Time=7.97 minutes.

Example 94

N-(4-((3R,4S)-4-(4-Chlorophenyl)-3,4-dihydroxy-3-methylpiperidin-1-yl)-2-methyl-4-oxobutan-2-yl)benzamide

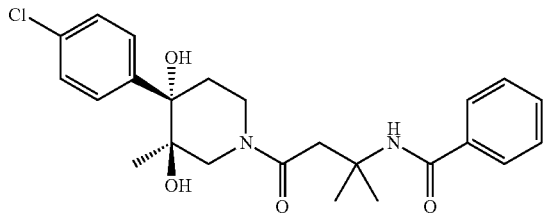 [SMILES: CC(C)(CC(=O)N1CC[C@](O)(c2ccc(Cl)cc2)[C@](C)(O)C1)NC(=O)c1ccccc1]

Example 94 was prepared from (±)-(trans)-4-(4-chlorophenyl)-3-methylpiperidine-3,4-diol and 3-benzamido-3-methylbutanoic acid using the procedure described in Example 93, step 6. MS (ESI$^+$)=445.3 (M+H)$^+$. $^1$H NMR (CD$_3$OD, 500 MHz) (NMR shows several rotamers) δ ppm 7.82-7.75 (m, 2 H), 7.57-7.49 (m, 2 H), 7.47-7.42 (m, 3 H), 7.28 (d, J=8.7 Hz, 1 H), 7.24 (d, J=8.2 Hz, 1 H), 4.51 (ddd, J=12.9, 2.5, 2.4 Hz, 0.6 H), 4.31 (d, J=13.3 Hz, 0.4 H), 4.12-4.03 (m, 0.4 H), 3.72 (d, J=13.8 Hz, 0.6 H), 3.60 (d, J=13.8 Hz, 0.6 H), 3.54 (td, J=12.7, 2.1 Hz, 0.4 H), 3.23 (d, J=15.1 Hz, 0.6 H), 3.11 (d, J=13.3 Hz, 0.6 H), 3.09-3.02 (m, 1 H), 2.87 (d, J=14.7 Hz, 0.4 H), 2.68-2.56 (m, 1.6 H), 1.63 (s, 1.4 H), 1.61-1.57 (m, 3.1H), 1.55 (s, 1.8 H), 1.43 (dd, J=13.7, 6.9 Hz, 1 H), 0.94 (s, 1.7 H), 0.92 (s, 1.3 H); HPLC Method: Inj. Vol.=5 uL, Start % B=10, 12 Min. 100%, 15 Min. 100%, Flow Rate=2 mL/min (1 mL/min on each column), Wavelength 1=220, Wavelength 2=254, Solvent Pair=TFA–ACN/H$_2$O, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=8.78 minutes, Col-2: Xbridge Phenyl 3.5 um, 4.6×150 mm; Retention Time=8.23 minutes.

Example 95

N-(4-((3S,4S)-4-(4-Chlorophenyl)-3,4-dihydroxy-3-methylpiperidin-1-yl)-2-methyl-4-oxobutan-2-yl)benzamide

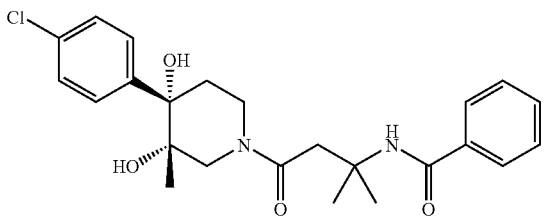 [SMILES: CC(C)(CC(=O)N1CC[C@](O)(c2ccc(Cl)cc2)[C@@](C)(O)C1)NC(=O)c1ccccc1]

Step 1: (3S,4S)-tert-Butyl 4-(4-chlorophenyl)-3,4-dihydroxy-3-methylpiperidine-1-carboxylate

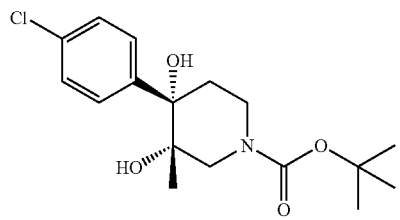 [SMILES: CC(C)(C)OC(=O)N1CC[C@](O)(c2ccc(Cl)cc2)[C@@](C)(O)C1]

A mixture of AD-Mix-alpha (2.5 g) and methanesulfonamide (0.309 g, 3.25 mmol) in tert-butanol/water (1:1) (15 mL) was cooled to 0° C., treated with tert-butyl 4-(4-chlorophenyl)-3-methyl-5,6-dihydropyridine-1(2H)-carboxylate (0.5 g, 1.624 mmol), and the reaction was stirred at 0° C. for 7 hours. Analysis by LCMS indicated only a trace of conversion to the desired product, so the mixture was allowed to warm to room temperature and stirred overnight. Analysis by LCMS indicated complete conversion of the starting material, so the mixture was cooled to 0° C., treated with sodium sulfite, and stirred at room temperature for 1 hour. The mixture was extracted 3× with ethyl acetate, and the combined organic phases were washed 3× with water, once with brine, dried over sodium sulfate, and concentrated in-vacuo. The residue was purified over an 80 g silica gel column, eluting at 60 mL/min with a 0% to 40% ethyl acetate/hexanes gradient followed by 40% ethyl acetate/hexanes to yield the title compound (395 mg, 1.156 mmol, 71.1% yield) as a colorless solid. MS (ESI$^+$)=268.2 (M–tert-BuO)$^+$, 250.2 (M–tert-BuO–H$_2$O)$^+$.

115

Step 2: (3S,4S)-4-(4-Chlorophenyl)-3-methylpiperidine-3,4-diol hydrochloride

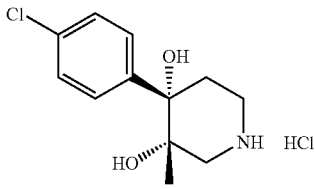 [SMILES: C[C@]1(O)CNCC[C@]1(O)c1ccc(Cl)cc1 ; Cl]

A solution of (3S,4S)-tert-butyl 4-(4-chlorophenyl)-3,4-dihydroxy-3-methylpiperidine-1-carboxylate (388 mg, 1.135 mmol) in 4 M HCl in dioxane (10 mL, 40.0 mmol) was stirred at room temperature for 2 hours. The mixture was concentrated in-vacuo, then concentrated 3× from methylene chloride to remove residual HCl and dioxane, to yield the title compound. MS (ESI$^+$)=242.2 (M+H)$^+$, 224.2 (M+H−H$_2$O)$^+$.

Step 3: Example 95

A mixture of (3S,4S)-4-(4-chlorophenyl)-3-methylpiperidine-3,4-diol, HCl (25 mg, 0.090 mmol), 3-benzamido-3-methylbutanoic acid (19.88 mg, 0.090 mmol), and triethylamine (0.044 mL, 0.315 mmol) in methylene chloride (1 mL) was treated with BOP (39.7 mg, 0.09 mmol), and the mixture was stirred overnight at room temperature. The solvent was evaporated with a stream of nitrogen, and the residue was taken up in ethyl acetate. The mixture was washed 3× with saturated sodium carbonate, and 3× with 1 N HCl, then the organic phase was concentrated in-vacuo. The residue was purified via prep HPLC using the following conditions: A=H$_2$O+0.05% TFA, B=acetonitrile+0.05% TFA, Column. Phenomenex Luna 5μ C18(2) 250×21.2 mm, Flow: 15 mL/min, Gradient: 0% B over 5 min, 0-100% B over 30 min, 100% B for 5 min. Fractions containing the desired product were combined and freeze-dried to yield Example 95 (25 mg, 0.056 mmol, 62.5% yield) as a colorless powder. MS (ESI$^+$)= 445.3 (M+H)$^+$. $^1$H NMR (CD$_3$OD, 500 MHz) (NMR shows several rotamers) δ ppm 7.82 (d, J=7.1 Hz, 1.2 H), 7.77 (d, J=7.2 Hz, 0.8 H), 7.56-7.49 (m, 1.8 H), 7.48-7.42 (m, 2 H), 7.38 (d, J=8.8 Hz, 1.2 H), 7.31 (d, J=8.8 Hz, 0.8 H), 7.25 (d, J=8.5 Hz, 1.2 H), 4.55 (dt, J=12.9, 2.5 Hz, 0.4 H), 4.29 (dd, J=12.4, 2.2 Hz, 0.6 H), 4.10 (dt, J=13.5, 2.5 Hz, 0.6 H), 3.74 (dd, J=12.9, 2.2 Hz, 0.4 H), 3.63-3.51 (m, 1.2 H), 3.23-3.16 (m, 1 H), 3.09 (d, J=12.4 Hz, 0.8 H), 2.84 (d, J=14.3 Hz, 0.6 H), 2.70 (d, J=14.8 Hz, 0.4 H), 2.49-2.39 (m, 1 H), 1.74-1.65 (m, 1.4 H), 1.60 (s, 1.8 H), 1.59 (s, 1.8 H), 1.58 (s, 1.1 H), 1.55 (s, 1.0 H), 0.96 (s, 0.9 H), 0.92-0.87 (m, 0.6 H), 0.81 (s, 1.5 H); HPLC Method: Inj. Vol.=5 uL, Start % B=10, 2 Min. 100%, 15 Min. 100%, Flow Rate=2 mL/min (1 mL/min on each column), Wavelength 1=220, Wavelength 2=254, Solvent Pair=TFA−ACN/H$_2$O, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=8.48 minutes, Col-2: Xbridge Phenyl 3.5 um, 4.6×150 mm; Retention Time=8.00 minutes.

116

Example 96

N-(4-((3S,4S)-4-(4-Chlorophenyl)-3,4-dihydroxy-3-methylpiperidin-1-yl)-2-methyl-4-oxobutan-2-yl)cyclopentanecarboxamide

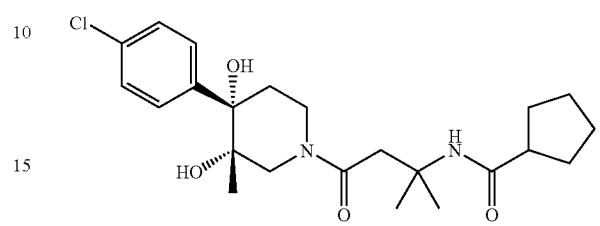

Example 96 was prepared from (3S,4S)-4-(4-chlorophenyl)-3-methylpiperidine-3,4-diol hydrochloride and 3-(cyclopentanecarboxamido)-3-methylbutanoic acid using the procedure described in Example 93, step 6. MS (ESI$^+$)=437.3 (M+H)$^+$. $^1$H NMR (CD$_3$OD, 500 MHz) (NMR shows several rotamers) δ ppm 7.55-7.50 (m, 2 H), 7.31 (d, J=8.5 Hz, 2 H), 4.53 (dd, J=10.7, 1.9 Hz, 0.4 H), 4.28 (dt, J=12.4, 0.8 Hz, 0.6 H), 4.04 (dd, J=13.2, 2.7 Hz, 0.6 H), 3.69 (dd, J=13.1, 2.3 Hz, 0.4 H), 3.59-3.52 (m, 1 H), 3.24 (d, J=14.6 Hz, 0.4 H), 3.09 (d, J=12.1 Hz, 1 H), 2.65-2.49 (m, 2 H), 2.42 (td, J=13.3, 4.7 Hz, 0.4 H), 1.89-1.53 (m, 10 H), 1.47-1.40 (m, 6 H), 0.93 (s, 1.1 H), 0.92-0.86 (m, 2.4 H); HPLC Method: Inj. Vol.=5 uL, Start % B=10, 12 Min. 100%, 15 Min. 100%, Flow Rate=2 mL/min (1 mL/min on each column), Wavelength 1=220 nm, Wavelength 2=254 nm, Solvent Pair=TFA−ACN/H$_2$O, Solvent A=0.05% TFA in H$_2$O:MeCN (95:5), Solvent B=0.05% TFA in H$_2$O:MeCN (5:95), Col-1: Sunfire C18 3.5 um, 4.6×150 mm; Retention Time=8.27 minutes, Col-2: Xbridge Phenyl 3.5 um, 4.6×150 mm; Retention Time=7.76 minutes.

Utility

In general, compounds of the present invention, such as particular compounds disclosed in the preceding examples, have been shown to be modulators of chemokine receptor activity. By displaying activity as modulators of chemokine receptor activity, compounds of the present invention are expected to be useful in the treatment of human diseases associated with chemokines and their cognate receptors.

Antagonism of MIP-1α Binding to Human THP-1 Cells

CCR1 ligand binding scintillation proximity assay (SPA) description:

For radioligand competition studies, a final concentration of 1×10$^5$ THP-1 monocytic leukemia cells are combined with 100 μg of LS WGA PS beads (Amersham, Cat.#: RPNQ 0260) in 40 μl of assay buffer (RPMI 1640 without phenol red, 50 mM HEPES, 5 mM MgCl$_2$, 1 mM CaCl$_2$, 0.1% BSA). The THP-1 cell/bead mixture is added to each well of a 384-well assay plate (PerkinElmer, Cat. #:6007899) containing test compound in 3-fold serial dilution, with final concentrations ranging from 8 μM to 140 μM. A final concentration of 0.1 nM [$^{125}$I]-MIP-1α (PerkinElmer, Cat. #NEX298) in 20 μl assay buffer is added to the reaction. Sealed assay plates are incubated at room temperature for 12 h then analyzed by LEADseeker™.

The competition data of the test compound over a range of concentrations is plotted as percentage inhibition of radioligand specific bound in the absence of test compound (percent of total signal). After correcting for non-specific binding, $IC_{50}$ values are determined. The $IC_{50}$ value is defined as the concentration of test compound needed to reduce $[^{125}I]$-MIP-1α specific binding by 50% and is calculated using the four parameter logistic equation to fit the normalized data. The Ki values are determined by application of the Cheng-Prusoff equation to the $IC_{50}$ values, where $K_i=IC_{50}/(1+\text{ligand concentration}/K_d)$ The Kd of $[^{125}I]$-MIP-1α in THP-1 cells is 0.1 nM. Each experiment is run in duplicate.

Compounds of the present invention were tested in the assay described immediately above and the results shown in Table 5 below were obtained.

TABLE 5

| Example No. | CCR1 $IC_{50}$ (nM) | Replicates* |
|---|---|---|
| 11 | 43.9 | 1 |
| 15 | 1181.0 | 1 |
| 21 | 42.0 | 1 |
| 27 | 41.6 | 1 |
| 28 | 46.7 | 1 |
| 35 | 1.7 | 1 |
| 40 | 1.5 | 1 |
| 42 | 1.8 | 1 |
| 50 | 2.2 | 2 |
| 60 | 45.3 | 1 |
| 63 | 1.9 | 2 |
| 72a | 1188.0 | 1 |
| 78 | 991.4 | 1 |
| 83 | 787.8 | 1 |
| 89 | 808.9 | 1 |

*number of individual assay determinations

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjögren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes)

(Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (1) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:
1. A compound of Formula (I):

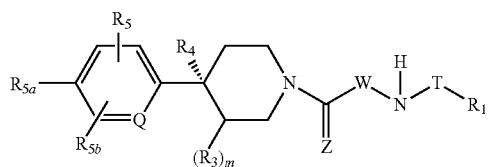

or a stereoisomer or pharmaceutically acceptable salt from thereof, wherein:

Q is CH or N;
Z is O or S;
W is —$CR_{3a}R_{3a}CR_{3b}R_{3b}$—;
T is a bond,

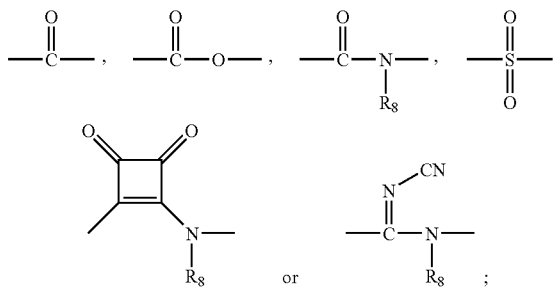

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O$(CR_8R_8)_r R_{10}$, —O$(CF_2)_r CF_3$, —O$(CR_8R_8)_r R_{10}$, —OH, —SH, —S$(CR_8R_8)_r R_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)$(CR_8R_8)_r R_{10}$, —NR$_9$C(=O)H, —NR$_9$C(=O)$(CR_8R_8)_r R_{10}$, —OC(=O)$(CR_8R_8)_r R_{10}$, —C(=NR$_{14}$)NR$_9$R$_9$, —NHC(=NR$_{14}$)NR$_{14}$R$_{14}$, —S(=O)$(CR_8R_8)_r R_{10}$, —S(O)$_2$$(CR_8R_8)_r R_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O$(CR_8R_8)_r R_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)$(CR_8R_8)_r R_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O$(CR_8R_8)_r R_{10}$, —O$(CF_2)_r CF_3$, —O$(CR_8R_8)_r R_{10}$, —OH, —SH, —S$(CR_8R_8)_r R_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)$(CR_8R_8)_r R_{10}$, —NR$_9$C(=O)H, —NR$_9$C(=O)$(CR_8R_8)_r R_{10}$, —OC(=O)$(CR_8R_8)_r R_{10}$, —C(=NR$_{14}$)NR$_9$R$_9$, —NHC(=NR$_{14}$)NR$_{14}$R$_{14}$, —S(=O)$(CR_8R_8)_r R_{10}$, —S(O)$_2$$(CR_8R_8)_r R_{10}$, —NR$_9$C(=O)OR$_6$, —NR$_9$S(O$_2$)R$_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —$(CR_8R_8)_r$OH, —$(CR_8R_8)_r$CN, —$(CR_8R_8)_r$OR$_6$, —$(CR_8R_8)_r$C(=O)R$_6$, —$(CR_8R_8)_r$OC(=O)NH$_2$, —$(CR_8R_8)_r$OC(=O)NHR$_6$, —$(CR_8R_8)_r$OC(=O)NR$_6$R$_6$, —$(CR_8R_8)_r$NH$_2$, —$(CR_8R_8)_r$NHR$_6$, —$(CR_8R_8)_r$NR$_6$R$_6$, —$(CR_8R_8)_r$NHC(=O)R$_6$, —$(CR_8R_8)_r$NHC(=O)NH$_2$, —$(CR_8R_8)_r$NHC(=O)NHR$_6$, —$(CR_8R_8)_r$NHC(=O)NR$_6$R$_6$, —$(CR_8R_8)_r$NHC(=O)OR$_6$, —$(CR_8R_8)_r$C(=O)NH$_2$, —$(CR_8R_8)_r$C(=O)NHR$_6$, —$(CR_8R_8)_r$C(=O)NR$_6$R$_6$ or —NHS(=O)$_2$R$_6$, wherein the alkyl may be optionally substituted with 0-3 fluorine atoms per carbon atom; provided that both $R_{3a}$'s can not be simultaneously attached via a heteroatom;

$R_{3b}$, at each occurrence, is independently hydrogen, alkyl, cycloalkyl, alkenyl, alkynyl, cycloalkylalkyl, silylalkyl, aryl, heteroaryl, arylalkyl or heteroarylalkyl, wherein the alkyl, cycloalkyl, alkenyl, alkynyl, cycloalkylalkyl, silylalkyl, aryl, heteroaryl, arylalkyl or heteroarylalkyl may be optionally substituted with 0-3 fluorine atoms per carbon atom, —OH, —CN, —OR$_6$, —OC(=O)R$_6$, —OC(=O)NH$_2$, —OC(=O)NHR$_6$, —OC(=O)NR$_6$R$_6$, —NH$_2$, —NHR$_6$, —NR$_6$R$_6$, —NHC(=O)R$_6$, —NHC(=O)NH$_2$, —NHC(=O)NHR$_6$, —NHC(=O)NR$_6$R$_6$, or —NHS(=O)$_2$R$_6$;

or the two $R_{3a}$'s or $R_{3b}$'s may be taken together with the carbon atom to which they are attached to form a 3- to 6-membered ring, wherein the carbon atoms of said ring may be optionally replaced with a heteroatom selected from N(R$_7$), O, and S;

$R_4$ is hydrogen, F, OH, CN or —NH$_2$;
$R_5$ is hydrogen, halo, alkyl, —CN or —Oalkyl;
$R_{5a}$ is halo, —CN or alkynyl;
$R_{5b}$ is hydrogen, halo, —CN, —Oalkyl or —C(=O)O$(CR_8R_8)_r R_{10}$;
$R_6$, at each occurrence, is independently alkyl, cycloalkyl, cycloalkylalkyl, aryl, arylalkyl, heteroaryl or heteroarylalkyl;
$R_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O$(CR_8R_8)_r R_{10}$, —OH, —SH, —C(=O)NR$_9$R$_9$, —S(O)$_2$NR$_9$R$_9$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$ $(CF_2)_rCF_3$, $-C(=O)(CR_8R_8)_rR_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-CN$, $-NO_2$, $-C(=O)OH$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-S(O)_3H$, $-P(O)_3H_2$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-C(=NR_{14})NR_9R_9$, $-NHC(=NR_{14})NR_{14}R_{14}$, $-S(=O)(CR_8R_8)_rR_{10}$, $-S(O)_2(CR_8R_8)_rR_{10}$, $-NR_9C(=O)OR_6$, $-NR_9S(O_2)R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, $-C(=O)O(CR_8R_8)_rR_{10}$, $-OH$, $-SH$, $-C(=O)NR_{14}R_{14}$, $-S(O)_2NR_{14}R_{14}$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-CN$, $-NO_2$, $-C(=O)OH$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-C(=NR_{14})NR_{14}R_{14}$, $-NHC(=NR_{14})NR_{14}R_{14}$, $-S(=O)(CR_8R_8)_rR_{14}$, $-S(O)_2(CR_8R_8)_rR_{14}$, $-NR_{14}C(=O)OR_6$, $-NR_{14}S(O_2)R_6$, $-OC(=O)NR_{14}R_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-CN$, $-NO_2$, $-C(=O)OH$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-C(=NR_{14})NR_{14}R_{14}$, $-NHC(=NR_{14})NR_{14}R_{14}$, $-S(=O)(CR_8R_8)_rR_{14}$, $-S(O)_2(CR_8R_8)_rR_{14}$, $-NR_{14}C(=O)OR_6$, $-NR_{14}S(O_2)R_6$, $-OC(=O)NR_{14}R_{14}$, aryloxy or arylalkyl;

$R_{14}$, at each occurrence, is independently selected from hydrogen, alkyl, cycloalkyl or phenyl;

m is 0-2; and r is 0-5;

provided that:

1) m is not 0 or 1 when $R_1$ is not a nitrogenated aromatic monocyclic group or nitrogenated aromatic fused-ring group which has at least one hydroxyl and/or amino.

2. The compound of claim 1, or a stereoisomer or pharmaceutically acceptable salt thereof, wherein Q is CH.

3. The compound of claim 1, or a stereoisomer or pharmaceutically acceptable salt thereof, wherein the compound is a compound of formula (Ia):

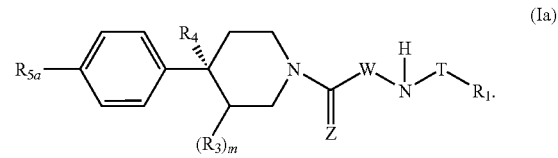

(Ia)

4. The compound of claim 1, or a stereoisomer or pharmaceutically acceptable salt thereof, wherein:

Z is O or S;

W is $-CR_{3a}R_{3a}CR_{3b}R_{3b}-$;

T is a bond,

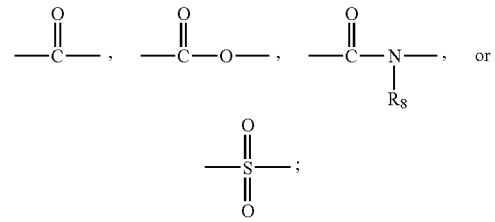

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-CN$, $-NO_2$, $-C(=O)OH$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-S(O)_3H$, $-P(O)_3H_2$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-NHC(=NR_{14})NR_{14}R_{14}$, $-S(=O)(CR_8R_8)_rR_{10}$, $-S(O)_2$ $(CR_8R_8)_rR_{10}$, —$NR_9C(=O)OR_6$, —$NR_9S(O_2)R_6$, =O, —$OC(=O)NR_9R_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —$C(=O)O(CR_8R_8)_rR_{10}$, —OH, —SH, —$C(=O)NR_{14}R_{14}$, —$S(O)_2NR_{14}R_{14}$, —$C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —$C(=O)(CR_8R_8)_rR_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —$C(=O)OH$, —$C(=O)O(CR_8R_8)_rR_{10}$, —$O(CF_2)_rCF_3$, —$O(CR_8R_8)_rR_{10}$, —OH, —SH, —$S(CR_8R_8)_rR_{10}$, —$S(O)_3H$, —$P(O)_3H_2$, —$C(=O)NR_9R_9$, —$NR_9R_9$, —$S(O)_2NR_9R_9$, —$NR_9S(O)_2(CF_2)_rCF_3$, —$C(=O)NR_9S(O)_2R_6$, —$S(O)_2NR_9C(=O)OR_6$, —$S(O)_2NR_9C(=O)NR_9R_9$, —$C(=O)NR_9S(O)_2(CF_2)_rCF_3$, —$C(=O)(CR_8R_8)_rR_{10}$, —$NR_9C(=O)H$, —$NR_9C(=O)(CR_8R_8)_rR_{10}$, —$OC(=O)(CR_8R_8)_rR_{10}$, —$NHC(=NR_{14})NR_{14}R_{14}$, —$S(=O)(CR_8R_8)_rR_{10}$, —$S(O)_2(CR_8R_8)_rR_{10}$, —$NR_9C(=O)OR_6$, —$NR_9S(O_2)R_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —$(CR_8R_8)_rOH$, —$(CR_8R_8)_rCN$, —$(CR_8R_8)_rOR_6$, —$(CR_8R_8)_rC(=O)R_6$, —$(CR_8R_8)_rOC(=O)NH_2$, —$(CR_8R_8)_rOC(=O)NHR_6$, —$(CR_8R_8)_rOC(=O)NR_6R_6$, —$(CR_8R_8)_rNH_2$, —$(CR_8R_8)_rNHR_6$, —$(CR_8R_8)_rNR_6R_6$, —$(CR_8R_8)_rNHC(=O)R_6$, —$(CR_8R_8)_rNHC(=O)NH_2$, —$(CR_8R_8)_rNHC(=O)NHR_6$, —$(CR_8R_8)_rNHC(=O)NR_6R_6$, —$(CR_8R_8)_rNHC(=O)OR_6$, —$(CR_8R_8)_rC(=O)NH_2$, —$(CR_8R_8)_rC(=O)NHR_6$, or —$(CR_8R_8)_rC(=O)NR_6R_6$, wherein the alkyl may be optionally substituted with 0-3 fluorine atoms per carbon atom; provided that both $R_{3a}$'s can not be simultaneously attached via a heteroatom;

or the two $R_{3a}$'s or $R_{3b}$'s may be taken together with the carbon atom to which they are attached to form a 3- to 6-membered ring, wherein the carbon atoms of said ring may be optionally replaced with a heteroatom selected from $N(R_7)$, O, and S;

$R_4$ is F, OH, CN or —$NH_2$;

$R_5$ is hydrogen, alkyl, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —$C(=O)O(CR_8R_8)_rR_{10}$, —OH, —SH, —$C(=O)NR_9R_9$, —$S(O)_2NR_9R_9$, —$C(=O)NR_9S(O)_2R_6$, —$S(O)_2NR_9C(=O)OR_6$, —$S(O)_2NR_9C(=O)NR_9R_9$, —$C(=O)NR_9S(O)_2(CF_2)_rCF_3$, —$C(=O)(CR_8R_8)_rR_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —$C(=O)OH$, —$C(=O)O(CR_8R_8)_rR_{10}$, —$O(CF_2)_rCF_3$, —$O(CR_8R_8)_rR_{10}$, —OH, —SH, —$S(CR_8R_8)_rR_{10}$, —$S(O)_3H$, —$P(O)_3H_2$, —$C(=O)NR_9R_9$, —$NR_9R_9$, —$S(O)_2NR_9R_9$, —$NR_9S(O)_2(CF_2)_rCF_3$, —$C(=O)NR_9S(O)_2R_6$, —$S(O)_2NR_9C(=O)OR_6$, —$S(O)_2NR_9C(=O)NR_9R_9$, —$C(=O)NR_9S(O)_2(CF_2)_rCF_3$, —$C(=O)(CR_8R_8)_rR_{10}$, —$NR_9C(=O)H$, —$NR_9C(=O)(CR_8R_8)_rR_{10}$, —$OC(=O)(CR_8R_8)_rR_{10}$, —$NHC(=NR_{14})NR_{14}R_{14}$, —$S(=O)(CR_8R_8)_rR_{10}$, —$S(O)_2(CR_8R_8)_rR_{10}$, —$NR_9C(=O)OR_6$, —$NR_9S(O_2)R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —$C(=O)O(CR_8R_8)_rR_{10}$, —OH, —SH, —$C(=O)NR_{14}R_{14}$, —$S(O)_2NR_{14}R_{14}$, —$C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —$C(=O)(CR_8R_8)_rR_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —$C(=O)OH$, —$C(=O)O(CR_8R_8)_rR_{14}$, —$O(CF_2)_rCF_3$, —$O(CR_8R_8)_rR_{14}$, —OH, —SH, —$S(CR_8R_8)_rR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2(CF_2)_rCF_3$, —$C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —$C(=O)(CR_8R_8)_rR_{14}$, —$NR_{14}C(=O)H$, —$NR_{14}C(=O)(CR_8R_8)_rR_{14}$, —$OC(=O)(CR_8R_8)_rR_{14}$, —$NHC(=NR_{14})NR_{14}R_{14}$, —$S(=O)(CR_8R_8)_rR_{14}$, —$S(O)_2(CR_8R_8)_rR_{14}$, —$NR_{14}C(=O)OR_6$, —$NR_{14}S(O_2)R_6$, —$OC(=O)NR_{14}R_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-4.

5. The compound of claim 1, or a stereoisomer or pharmaceutically acceptable salt thereof, wherein:

Z is O or S;

W is —CR$_{3a}$R$_{3a}$CR$_{3b}$R$_{3b}$—;

T is a bond,

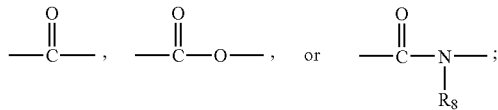

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —(CR$_8$R$_8$)$_r$OH, —(CR$_8$R$_8$)$_r$CN, —(CR$_8$R$_8$)$_r$OR$_6$, —(CR$_8$R$_8$)$_r$OC(=O)R$_6$, —(CR$_8$R$_8$)$_r$OC(=O)NH$_2$, —(CR$_8$R$_8$)$_r$OC(=O)NHR$_6$, —(CR$_8$R$_8$)$_r$OC(=O)NR$_6$R$_6$, —(CR$_8$R$_8$)$_r$NH$_2$, —(CR$_8$R$_8$)$_r$NHR$_6$, —(CR$_8$R$_8$)$_r$NR$_6$R$_6$, —(CR$_8$R$_8$)$_r$NHC(=O)R$_6$, —(CR$_8$R$_8$)$_r$NHC(=O)NH$_2$, —(CR$_8$R$_8$)$_r$NHC(=O)NHR$_6$, —(CR$_8$R$_8$)$_r$C(=O)NH$_2$ or —(CR$_8$R$_8$)$_r$C(=O)NHR$_6$, wherein the alkyl may be optionally substituted with 0-3 fluorine atoms per carbon atom; provided that both R$_{3a}$'s can not be simultaneously attached via a heteroatom;

or the two R$_{3a}$'s or R$_{3b}$'s may be taken together with the carbon atom to which they are attached to form a 3- to 6-membered ring, wherein the carbon atoms of said ring may be optionally replaced with a heteroatom selected from N(R$_7$), O, and S;

R$_4$ is F, OH or —NH$_2$;

R$_5$ is hydrogen, halo or —CN;

R$_{5a}$ is halo, —CN or alkynyl;

R$_{5b}$ is hydrogen, halo or —CN;

R$_6$, at each occurrence, is independently alkyl, cycloalkyl, cycloalkylalkyl, aryl, arylalkyl, heteroaryl or heteroarylalkyl;

R$_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_9$R$_9$, —S(O)$_2$NR$_9$R$_9$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-3.

6. The compound of claim 1, or a stereoisomer or pharmaceutically acceptable salt thereof, wherein:

Z is O;

W is —CR$_{3a}$R$_{3a}$CR$_{3b}$R$_{3b}$—,

T is

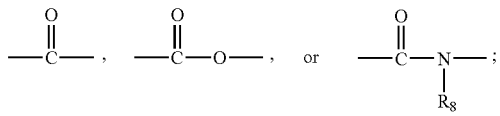

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —(CR$_8$R$_8$)$_r$OH, —(CR$_8$R$_8$)$_r$CN, —(CR$_8$R$_8$)$_r$OR$_6$, —(CR$_8$R$_8$)$_r$OC(=O)R$_6$, —(CR$_8$R$_8$)$_r$OC(=O)NH$_2$, —(CR$_8$R$_8$)$_r$OC(=O)NHR$_6$, —(CR$_8$R$_8$)$_r$OC(=O)NR$_6$R$_6$, —(CR$_8$R$_8$)$_r$NH$_2$, —(CR$_8$R$_8$)$_r$NHR$_6$, —(CR$_8$R$_8$)$_r$NR$_6$R$_6$, —(CR$_8$R$_8$)$_r$NHC(=O)R$_6$, —(CR$_8$R$_8$)$_r$NHC(=O)NH$_2$ or —(CR$_8$R$_8$)$_r$C(=O)NH$_2$, wherein the alkyl may be optionally substituted with 0-3 fluorine atoms per carbon atom; provided that both $R_{3a}$'s can not be simultaneously attached via a heteroatom;

or the two $R_{3a}$'s or $R_{3b}$'s may be taken together with the carbon atom to which they are attached to form a 3- to 6-membered ring, wherein the carbon atoms of said ring may be optionally replaced with a heteroatom selected from $N(R_7)$, O, and S;

$R_4$ is F, OH, or —$NH_2$;

$R_5$ is hydrogen, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O($CR_8R_8$)$_r$$R_{10}$, —OH, —SH, —C(=O)$NR_9R_9$, —S(O)$_2NR_9R_9$, —C(=O)$NR_9S(O)_2R_6$, —S(O)$_2NR_9C$(=O)$OR_6$, —S(O)$_2NR_9C$(=O)$NR_9R_9$, —C(=O)$NR_9S(O)_2$($CF_2$)$_r$$CF_3$, —C(=O)($CR_8R_8$)$_r$$R_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —C(=O)$NR_9R_9$, —$NR_9R_9$, —S(O)$_2NR_9R_9$, —$NR_9S(O)_2$($CF_2$)$_r$$CF_3$, —C(=O)$NR_9S(O)_2R_6$, —S(O)$_2NR_9C$(=O)$OR_6$, —S(O)$_2NR_9C$(=O)$NR_9R_9$, —C(=O)$NR_9S(O)_2$($CF_2$)$_r$$CF_3$, —C(=O)($CR_8R_8$)$_r$$R_{10}$, —$NR_9C$(=O)H, —$NR_9C$(=O)($CR_8R_8$)$_r$$R_{10}$, —OC(=O)($CR_8R_8$)$_r$$R_{10}$, —S(=O)($CR_8R_8$)$_r$$R_{10}$, —S(O)$_2$($CR_8R_8$)$_r$$R_{10}$, —$NR_9C$(=O)$OR_6$, —$NR_9S(O)_2R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O($CR_8R_8$)$_r$$R_{10}$, —OH, —SH, —C(=O)$NR_{14}R_{14}$, —S(O)$_2NR_{14}R_{14}$, —C(=O)$NR_{14}S(O)_2R_6$, —S(O)$_2NR_{14}C$(=O)$OR_6$, —S(O)$_2NR_{14}C$(=O)$NR_{14}R_{14}$, —C(=O)$NR_{14}S(O)_2$($CF_2$)$_r$$CF_3$, —C(=O)($CR_8R_8$)$_r$$R_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —C(=O)$NR_{14}R_{14}$, —$NR_{14}R_{14}$, —S(O)$_2NR_{14}R_{14}$, —$NR_{14}S(O)_2$($CF_2$)$_r$$CF_3$, —C(=O)$NR_{14}S(O)_2R_6$, —S(O)$_2NR_{14}C$(=O)$OR_6$, —S(O)$_2$$NR_{14}C$(=O)$NR_{14}R_{14}$, —C(=O)$NR_{14}S(O)_2$($CF_2$)$_r$$CF_3$, —C(=O)($CR_8R_8$)$_r$$R_{14}$, —$NR_{14}C$(=O)H, —$NR_{14}C$(=O)($CR_8R_8$)$_r$$R_{14}$, —OC(=O)($CR_8R_8$)$_r$$R_{14}$, —S(=O)($CR_8R_8$)$_r$$R_{14}$, —S(O)$_2$($CR_8R_8$)$_r$$R_{14}$, —$NR_{14}C$(=O)$OR_6$, —$NR_{14}S(O)_2R_6$, —OC(=O)$NR_{14}R_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —C(=O)$NR_{14}R_{14}$, —$NR_{14}R_{14}$, —S(O)$_2NR_{14}R_{14}$, —$NR_{14}S(O)_2$($CF_2$)$_r$$CF_3$, —C(=O)$NR_{14}S(O)_2R_6$, —S(O)$_2NR_{14}C$(=O)$OR_6$, —S(O)$_2NR_{14}C$(=O)$NR_{14}R_{14}$, —C(=O)$NR_{14}S(O)_2$($CF_2$)$_r$$CF_3$, —C(=O)($CR_8R_8$)$_r$$R_{14}$, —$NR_{14}C$(=O)H, —$NR_{14}C$(=O)($CR_8R_8$)$_r$$R_{14}$, —OC(=O)($CR_8R_8$)$_r$$R_{14}$, —S(=O)($CR_8R_8$)$_r$$R_{14}$, —S(O)$_2$($CR_8R_8$)$_r$$R_{14}$, —$NR_{14}C$(=O)$OR_6$, —$NR_{14}S(O)_2R_6$, —OC(=O)$NR_{14}R_{14}$, aryloxy or arylalkyl;

$R_{14}$, at each occurrence, is independently selected from hydrogen, alkyl, cycloalkyl or phenyl;

m is 0-2; and r is 0-2.

7. The compound of claim 1, or a stereoisomer or pharmaceutically acceptable salt thereof, wherein:

Z is O;

W is —$CR_{3a}R_{3a}CR_{3b}R_{3b}$—;

T is $$-\overset{\overset{O}{\|}}{C}-, \quad -\overset{\overset{O}{\|}}{C}-O-, \quad \text{or} \quad -\overset{\overset{O}{\|}}{C}-\underset{\underset{R_8}{|}}{N}-;$$

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —C(=O)$NR_9R_9$, —$NR_9R_9$, —S(O)$_2NR_9R_9$, —$NR_9S(O)_2$($CF_2$)$_r$$CF_3$, —C(=O)$NR_9S(O)_2R_6$, —S(O)$_2NR_9C$(=O)$OR_6$, —S(O)$_2NR_9C$(=O)$NR_9R_9$, —C(=O)$NR_9S(O)_2$($CF_2$)$_r$$CF_3$, —C(=O)($CR_8R_8$)$_r$$R_{10}$, —$NR_9C$(=O)H, —$NR_9C$(=O)($CR_8R_8$)$_r$$R_{10}$, —OC(=O)($CR_8R_8$)$_r$$R_{10}$, —S(=O)($CR_8R_8$)$_r$$R_{10}$, —S(O)$_2$($CR_8R_8$)$_r$$R_{10}$, —$NR_9C$(=O)$OR_6$, —$NR_9S(O)_2R_6$, =O, —OC(=O)$NR_9R_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(═O)O($CR_8R_8$)$_r$$R_{10}$, —OH, —SH, —C(═O)$NR_{14}R_{14}$, —S(O)$_2$$NR_{14}R_{14}$, —C(═O)$NR_{14}$S(O)$_2$$R_6$, —S(O)$_2$$NR_{14}$C(═O)$OR_6$, —S(O)$_2$$NR_{14}$C(═O)$NR_{14}R_{14}$, —C(═O)$NR_{14}$S(O)$_2$($CF_2$)$_r$$CF_3$, —C(═O)($CR_8R_8$)$_r$$R_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(═O)OH, —C(═O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —C(═O)$NR_9R_9$, —$NR_9R_9$, —S(O)$_2$$NR_9R_9$, —$NR_9$S(O)$_2$($CF_2$)$_r$$CF_3$, —C(═O)$NR_9$S(O)$_2$$R_6$, —S(O)$_2$$NR_9$C(═O)$OR_6$, —S(O)$_2$$NR_9$C(═O)$NR_9R_9$, —C(═O)$NR_9$S(O)$_2$($CF_2$)$_r$$CF_3$, —C(═O)($CR_8R_8$)$_r$$R_{10}$, —$NR_9$C(═O)H, —$NR_9$C(═O)($CR_8R_8$)$_r$$R_{10}$, —OC(═O)($CR_8R_8$)$_r$$R_{10}$, —S(═O)($CR_8R_8$)$_r$$R_{10}$, —S(O)$_2$($CR_8R_8$)$_r$$R_{10}$, —$NR_9$C(═O)$OR_6$, —$NR_9$S($O_2$)$R_6$, aryloxy, arylalkyl or arylalkyloxyalkyl;

$R_3$, at each occurrence, is independently OH or alkyl;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —($CR_8R_8$)$_r$OH, —($CR_8R_8$)$_r$CN, —($CR_8R_8$)$_r$$OR_6$, —($CR_8R_8$)$_r$C(═O)$R_6$, —($CR_8R_8$)$_r$OC(═O)$NH_2$, —($CR_8R_8$)$_r$OC(═O)$NHR_6$, —($CR_8R_8$)$_r$OC(═O)$NR_6R_6$, —($CR_8R_8$)$_r$$NH_2$, —($CR_8R_8$)$_r$$NHR_6$, —($CR_8R_8$)$_r$$NR_6R_6$ or —($CR_8R_8$)$_r$C(═O)$NH_2$, wherein the alkyl may be optionally substituted with 0-3 fluorine atoms per carbon atom; provided that both $R_{3a}$'s can not be simultaneously attached via heteroatom;

or the two $R_{3a}$'s or $R_{3b}$'s may be taken together with the carbon atom to which they are attached to form a 3- to 6-membered ring, wherein the carbon atoms of said ring may be optionally replaced with a heteroatom selected from N($R_7$), O, and S;

$R_4$ is F, OH or —$NH_2$;

$R_5$ is hydrogen, halo or —CN;

$R_{5a}$ is halo or —CN;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(═O)O($CR_8R_8$)$_r$$R_{10}$, —OH, —SH, —C(═O)$NR_9R_9$, —S(O)$_2$$NR_9R_9$, —C(═O)$NR_9$S(O)$_2$$R_6$, —S(O)$_2$$NR_9$C(═O)$OR_6$, —S(O)$_2$$NR_9$C(═O)$NR_9R_9$, —C(═O)$NR_9$S(O)$_2$($CF_2$)$_r$$CF_3$, —C(═O)($CR_8R_8$)$_r$$R_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(═O)OH, —C(═O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —C(═O)$NR_9R_9$, —$NR_9R_9$, —S(O)$_2$$NR_9R_9$, —$NR_9$S(O)$_2$($CF_2$)$_r$$CF_3$, —C(═O)$NR_9$S(O)$_2$$R_6$, —S(O)$_2$$NR_9$C(═O)$OR_6$, —S(O)$_2$$NR_9$C(═O)$NR_9R_9$, —C(═O)$NR_9$S(O)$_2$($CF_2$)$_r$$CF_3$, —C(═O)($CR_8R_8$)$_r$$R_{10}$, —$NR_9$C(═O)H, —$NR_9$C(═O)($CR_8R_8$)$_r$$R_{10}$, —OC(═O)($CR_8R_8$)$_r$$R_{10}$, —S(═O)($CR_8R_8$)$_r$$R_{10}$, —S(O)$_2$($CR_8R_8$)$_r$$R_{10}$, —$NR_9$C(═O)$OR_6$, —$NR_9$S($O_2$)$R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(═O)O($CR_8R_8$)$_r$$R_{10}$, —OH, —SH, —C(═O)$NR_{14}R_{14}$, —S(O)$_2$$NR_{14}R_{14}$, —C(═O)$NR_{14}$S(O)$_2$$R_6$, —S(O)$_2$$NR_{14}$C(═O)$OR_6$, —S(O)$_2$$NR_{14}$C(═O)$NR_{14}R_{14}$, —C(═O)$NR_{14}$S(O)$_2$($CF_2$)$_r$$CF_3$, —C(═O)($CR_8R_8$)$_r$$R_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(═O)OH, —C(═O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —C(═O)$NR_{14}R_{14}$, —$NR_{14}R_{14}$, —S(O)$_2$$NR_{14}R_{14}$, —$NR_{14}$S(O)$_2$($CF_2$)$_r$$CF_3$, —C(═O)$NR_{14}$S(O)$_2$$R_6$, —S(O)$_2$$NR_{14}$C(═O)$OR_6$, —S(O)$_2$$NR_{14}$C(═O)$NR_{14}R_{14}$, —C(═O)$NR_{14}$S(O)$_2$($CF_2$)$_r$$CF_3$, —C(═O)($CR_8R_8$)$_r$$R_{14}$, —$NR_{14}$C(═O)H, —$NR_{14}$C(═O)($CR_8R_8$)$_r$$R_{14}$, —OC(═O)($CR_8R_8$)$_r$$R_{14}$, —S(═O)($CR_8R_8$)$_r$$R_{14}$, —S(O)$_2$($CR_8R_8$)$_r$$R_{14}$, —$NR_{14}$C(═O)$OR_6$, —$NR_{14}$S($O_2$)$R_6$, —OC(═O)$NR_{14}R_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(═O)OH, —C(═O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —C(═O)$NR_{14}R_{14}$, —$NR_{14}R_{14}$, —S(O)$_2$$NR_{14}R_{14}$, —$NR_{14}$S(O)$_2$($CF_2$)$_r$$CF_3$, —C(═O)$NR_{14}$S(O)$_2$$R_6$, —S(O)$_2$$NR_{14}$C(═O)$OR_6$, —S(O)$_2$$NR_{14}$C(═O)$NR_{14}R_{14}$, —C(═O)$NR_{14}$S(O)$_2$($CF_2$)$_r$$CF_3$, —C(═O)($CR_8R_8$)$_r$$R_{14}$, —$NR_{14}$C(═O)H, —$NR_{14}$C(═O)($CR_8R_8$)$_r$$R_{14}$, —OC(═O)($CR_8R_8$)$_r$$R_{14}$, —S(═O)($CR_8R_8$)$_r$$R_{14}$, —S(O)$_2$($CR_8R_8$)$_r$$R_{14}$, —$NR_{14}$C(═O)$OR_6$, —$NR_{14}$S($O_2$)$R_6$, —OC(═O)$NR_{14}R_{14}$, aryloxy or arylalkyl;

$R_{14}$, at each occurrence, is independently selected from hydrogen, alkyl, cycloalkyl or phenyl;

m is 0-2; and r is 0-2.

8. The compound of claim 1, or a stereoisomer or pharmaceutically acceptable salt thereof, wherein:

Z is O;

W is —$CR_{3a}R_{3a}CR_{3b}R_{3b}$—;

T is

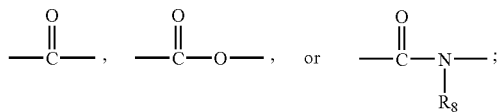

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —C(=O)$NR_9R_9$, —$NR_9R_9$, —S$(O)_2NR_9R_9$, —$NR_9S(O)_2(CF_2)_rCF_3$, —C(=O)$NR_9S(O)_2R_6$, —S$(O)_2NR_9C$(=O)$OR_6$, —S$(O)_2NR_9C$(=O)$NR_9R_9$, —C(=O)$NR_9S(O)_2(CF_2)_r$ $CF_3$, —C(=O)$(CR_8R_8)_rR_{10}$, —$NR_9C$(=O)H, —$NR_9C$(=O)$(CR_8R_8)_rR_{10}$, —OC(=O)$(CR_8R_8)_rR_{10}$, —S(=O)$(CR_8R_8)_rR_{10}$, —S$(O)_2(CR_8R_8)_rR_{10}$, —$NR_9C$(=O)$OR_6$, —$NR_9S(O)_2R_6$, =O, —OC(=O)$NR_9R_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O$(CR_8R_8)_r$ $R_{10}$, —OH, —SH, —C(=O)$NR_{14}R_{14}$, —S$(O)_2$$NR_{14}R_{14}$, —C(=O)$NR_{14}S(O)_2R_6$, —S$(O)_2NR_{14}C$(=O)$OR_6$, —S$(O)_2NR_{14}C$(=O)$NR_{14}R_{14}$, —C(=O) $NR_{14}S(O)_2(CF_2)_rCF_3$, —C(=O)$(CR_8R_8)_rR_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —C(=O)$NR_9R_9$, —$NR_9R_9$, —S$(O)_2NR_9R_9$, —$NR_9S(O)_2(CF_2)_rCF_3$, —C(=O)$NR_9S(O)_2R_6$, —S$(O)_2NR_9C$(=O)$OR_6$, —S$(O)_2NR_9C$(=O)$NR_9R_9$, —C(=O)$NR_9S(O)_2$ $(CF_2)_r$ $CF_3$, —C(=O)$(CR_8R_8)_rR_{10}$, —$NR_9C$(=O)H, —$NR_9C$(=O)$(CR_8R_8)_rR_{10}$, —OC(=O)$(CR_8R_8)_rR_{10}$, —S(=O)$(CR_8R_8)_rR_{10}$, —S$(O)_2(CR_8R_8)_rR_{10}$, —$NR_9C$(=O)$OR_6$, —$NR_9S(O)_2R_6$, aryloxy, arylalkyl or arylalkyloxyalkyl;

$R_3$, at each occurrence, is independently OH or alkyl;

$R_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —$(CR_8R_8)_r$ OH, —$(CR_8R_8)_rCN$, —$(CR_8R_8)_rOR_6$, —$(CR_8R_8)_rC$(=O)$R_6$, —$(CR_8R_8)_rOC$(=O)$NH_2$, —$(CR_8R_8)_rOC$(=O)$NHR_6$, —$(CR_8R_8)_rOC$(=O)$NR_6R_6$ or —$(CR_8R_8)_rNH_2$, wherein the alkyl may be optionally substituted with 0-3 fluorine atoms per carbon atom; provided that both $R_{3a}$'s can not be simultaneously attached via a heteroatom;

or the two $R_{3a}$'s or $R_{3b}$'s may be taken together with the carbon atom to which they are attached to form a 3- to 6-membered ring, wherein the carbon atoms of said ring may be optionally replaced with a heteroatom selected from N($R_7$), O, and S;

$R_4$ is F or OH;

$R_5$ is hydrogen, halo or —CN;

$R_{5a}$ is halo or —CN;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$ is hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O$(CR_8R_8)_r$ $R_{10}$, —OH, —SH, —C(=O)$NR_9R_9$, —S$(O)_2NR_9R_9$, —C(=O)$NR_9S(O)_2R_6$, —S$(O)_2NR_9C$(=O)$OR_6$, —S$(O)_2NR_9C$(=O)$NR_9R_9$, —C(=O)$NR_9S(O)_2$ $(CF_2)_r$ $CF_3$, —C(=O)$(CR_8R_8)_rR_{10}$ or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —C(=O)$NR_9R_9$, —$NR_9R_9$, —S$(O)_2NR_9R_9$, —$NR_9S(O)_2(CF_2)_rCF_3$, —C(=O)$NR_9S(O)_2R_6$, —S$(O)_2NR_9C$(=O)$OR_6$, —S$(O)_2NR_9C$(=O)$NR_9R_9$, —C(=O)$NR_9S(O)_2$ $(CF_2)_r$ $CF_3$, —C(=O)$(CR_8R_8)_rR_{10}$, —$NR_9C$(=O)H, —$NR_9C$(=O)$(CR_8R_8)_rR_{10}$, —OC(=O)$(CR_8R_8)_rR_{10}$, —S(=O)$(CR_8R_8)_rR_{10}$, —S$(O)_2(CR_8R_8)_rR_{10}$, —$NR_9C$(=O)$OR_6$, —$NR_9S(O)_2R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O$(CR_8R_8)_rR_{10}$, —OH, —SH, —C(=O)$NR_{14}R_{14}$, —S$(O)_2NR_{14}R_{14}$, —C(=O)$NR_{14}S(O)_2R_6$, —S$(O)_2$$NR_{14}C$(=O)$OR_6$, —S$(O)_2NR_{14}C$(=O)$NR_{14}R_{14}$, —C(=O)$NR_{14}S(O)_2(CF_2)_rCF_3$, —C(=O)$(CR_8R_8)_r$ $R_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)

O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-2.

9. The compound of claim 1, or a stereoisomer or pharmaceutically acceptable salt thereof, wherein:

Z is O;

W is —CR$_{3a}$R$_{3a}$CR$_{3b}$R$_{3b}$—;

T is

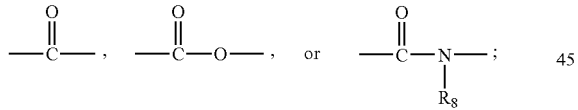

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

R$_3$, at each occurrence, is independently OH or alkyl;

R$_{3a}$, at each occurrence, is independently hydrogen, alkyl, cycloalkyl, alkenyl, alkynyl, cycloalkylalkyl, silylalkyl, aryl, arylalkyl, heteroaryl, heteroarylalkyl, —(CR$_8$R$_8$)$_r$OH, —(CR$_8$R$_8$)$_r$CN, —(CR$_8$R$_8$)$_r$OR$_6$, —(CR$_8$R$_8$)$_r$OC(=O)R$_6$, —(CR$_8$R$_8$)$_r$OC(=O)NH$_2$, or —(CR$_8$R$_8$)$_r$C(=O)NHR$_6$, wherein the alkyl may be optionally substituted with 0-3 fluorine atoms per carbon atom; provided that both R$_{3a}$'s can not be simultaneously attached via a heteroatom;

R$_4$ is F or OH;

R$_5$ is hydrogen, halo or —CN;

R$_{5a}$ is halo or —CN;

R$_{5b}$ is hydrogen, halo or —CN;

R$_6$, at each occurrence, is independently alkyl, cycloalkyl, cycloalkylalkyl, aryl, arylalkyl, heteroaryl or heteroarylalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$ (CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-2.

10. The compound of claim 1, or a stereoisomer or pharmaceutically acceptable salt thereof, wherein:

Z is O;

W is —CR$_{3a}$R$_{3a}$CR$_{3b}$R$_{3b}$—;

T is

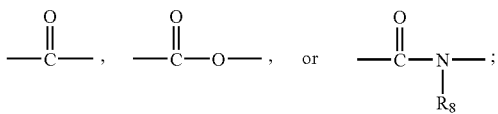

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$;

R$_{1b}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl;

R$_{3a}$, at each occurrence, is independently hydrogen, alkyl, cycloalkyl, alkenyl, cycloalkylalkyl, silylalkyl, aryl, arylalkyl, heteroaryl, heteroarylalkyl, OH, —OR$_6$ or —OC(=O)R$_6$, wherein the alkyl may be optionally substituted with 0-3 fluorine atoms per carbon atom;

R$_4$ is OH;

R$_5$ is hydrogen or halo;

R$_{5a}$ is halo or —CN;

R$_{5b}$ is hydrogen or halo;

R$_6$, at each occurrence, is independently alkyl, cycloalkyl, aryl or heteroaryl;

R$_8$, at each occurrence, is independently hydrogen or alkyl;

R$_9$, at each occurrence, is independently hydrogen, alkyl, cycloalkyl, aryl, heteroaryl or heterocyclyl, wherein the aryl, heteroaryl or heterocyclyl may be optionally substituted with 0-5 R$_{9a}$, and the heteroaryl or heterocyclyl contain 1-4 heteroatoms selected from N, O, and S;

R$_{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{10}$, at each occurrence, is independently selected from alkyl, aryl or heterocyclyl, wherein the aryl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-2.

11. A pharmaceutical composition comprised of a pharmaceutically acceptable carrier and a therapeutically effective amount of a compound of claim 1.

* * * * *

UNITED STATES PATENT AND TRADEMARK OFFICE
CERTIFICATE OF CORRECTION

Page 1 of 1

PATENT NO. : 8,501,782 B2
APPLICATION NO. : 12/670016
DATED : August 6, 2013
INVENTOR(S) : Daniel S. Gardner et al.

It is certified that error appears in the above-identified patent and that said Letters Patent is hereby corrected as shown below:

<u>In the Claims:</u>

Claim 1:

Column 125, line 17, after "salt", delete "from".

Column 125, lines 55 and 56, change "heterocyclyl" to -- heterocyclyl, --.

Column 126, line 26, change "—$(CR_8R_8)_rC$" to -- —$(CR_8R_8)_rOC$ --.

Claim 4:

Column 129, line 40, change "—$(CR_8R_8)_rC$" to -- —$(CR_8R_8)_rOC$ --.

Claim 7:

Column 137, line 31, change "—$(CR_8R_8)_rC$" to -- —$(CR_8R_8)_rOC$ --.

Claim 8:

Column 139, line 66, change "—$(CR_8R_8)_rC$" to -- —$(CR_8R_8)_rOC$ --.

Signed and Sealed this
First Day of April, 2014

Michelle K. Lee
*Deputy Director of the United States Patent and Trademark Office*